United States Patent
Schammel et al.

(10) Patent No.: US 9,556,086 B2
(45) Date of Patent: Jan. 31, 2017

(54) OXIDATIVE COUPLING OF METHANE SYSTEMS AND METHODS

(71) Applicant: Siluria Technologies, Inc., San Francisco, CA (US)

(72) Inventors: Wayne P. Schammel, San Francisco, CA (US); Julian Wolfenbarger, Landenberg, PA (US); Milind Ajinkya, Oakton, VA (US); Jon McCarty, Menlo Park, CA (US); Joel M. Cizeron, Redwood City, CA (US); Sam Weinberger, San Francisco, CA (US); Justin Dwight Edwards, League City, TX (US); David Sheridan, Menlo Park, CA (US); Erik C. Scher, San Francisco, CA (US); Jarod McCormick, San Carlos, CA (US); Fabio R. Zurcher, Brisbane, CA (US); Alex Tkachenko, San Francisco, CA (US); Joel Gamoras, Vallejo, CA (US); Dmitry Karshtedt, Washington, DC (US); Greg Nyce, Pleasanton, CA (US)

(73) Assignee: SILURIA TECHNOLOGIES, INC., San Francisco, CA (US)

( * ) Notice: Subject to any disclaimer, the term of this patent is extended or adjusted under 35 U.S.C. 154(b) by 0 days.

(21) Appl. No.: 14/789,901

(22) Filed: Jul. 1, 2015

(65) Prior Publication Data

US 2015/0321974 A1 Nov. 12, 2015

Related U.S. Application Data

(63) Continuation of application No. 13/900,898, filed on May 23, 2013, now Pat. No. 9,469,577.

(Continued)

(51) Int. Cl.
 *C07C 2/00* (2006.01)
 *C07C 2/84* (2006.01)
 (Continued)

(52) U.S. Cl.
 CPC .................. *C07C 2/84* (2013.01); *B01J 8/001* (2013.01); *B01J 8/0257* (2013.01); *B01J 8/0453* (2013.01);
 (Continued)

(58) Field of Classification Search
 CPC ....................................... C07C 2/00
 (Continued)

(56) References Cited

U.S. PATENT DOCUMENTS 2,486,980 A 11/1949 Robinson
2,579,601 A 12/1951 Nelson et al.
(Continued)

FOREIGN PATENT DOCUMENTS

CA 2765769 A1 1/2011
CN 1403375 A 3/2003
(Continued)

OTHER PUBLICATIONS

"Water Electrolysis & Renewable Energy Systems" FuelCellToday (May 2013).
(Continued)

*Primary Examiner* — Thuan D Dang
(74) *Attorney, Agent, or Firm* — Wilson Sonsini Goodrich & Rosati

(57) ABSTRACT

Systems and methods conducive to the formation of one or more alkene hydrocarbons using a methane source and an oxidant in an oxidative coupling of methane (OCM) reaction are provided. One or more vessels each containing one or more catalyst beds containing one or more catalysts each having similar or differing chemical composition or physical (Continued)

form may be used. The one or more catalyst beds may be operated under a variety of conditions. At least a portion of the catalyst beds may be operated under substantially adiabatic conditions. At least a portion of the catalyst beds may be operated under substantially isothermal conditions.

20 Claims, 9 Drawing Sheets

Related U.S. Application Data

(60) Provisional application No. 61/651,485, filed on May 24, 2012, provisional application No. 61/791,312, filed on Mar. 15, 2013.

(51) Int. Cl.
*B01J 8/04* (2006.01)
*B01J 8/06* (2006.01)
*B01J 8/02* (2006.01)
*B01J 8/00* (2006.01)
*C10G 50/00* (2006.01)

(52) U.S. Cl.
CPC .............. *B01J 8/0457* (2013.01); *B01J 8/0496* (2013.01); *B01J 8/067* (2013.01); *C10G 50/00* (2013.01); *B01J 2208/00044* (2013.01); *B01J 2208/0053* (2013.01); *B01J 2208/00061* (2013.01); *B01J 2208/00176* (2013.01); *B01J 2208/00256* (2013.01); *B01J 2208/00539* (2013.01); *B01J 2208/00548* (2013.01); *B01J 2208/00557* (2013.01); *B01J 2208/00628* (2013.01); *B01J 2208/025* (2013.01); *B01J 2208/027* (2013.01); *B01J 2219/002* (2013.01); *B01J 2219/00198* (2013.01); *B01J 2219/00202* (2013.01); *B01J 2219/00213* (2013.01); *B01J 2219/00231* (2013.01); *B01J 2219/00238* (2013.01); *C10G 2300/1025* (2013.01); *C10G 2300/1092* (2013.01); *C10G 2400/02* (2013.01); *C10G 2400/20* (2013.01); *Y02P 30/40* (2015.11)

(58) Field of Classification Search
USPC .......................................... 585/501, 648, 943
See application file for complete search history.

(56) References Cited

U.S. PATENT DOCUMENTS

| | | |
|---|---|---|
| 2,673,221 A | 3/1954 | Berntsen et al. |
| 2,880,592 A | 4/1959 | Davison et al. |
| 2,943,125 A | 6/1960 | Martin et al. |
| 3,128,317 A | 4/1964 | Arkell et al. |
| 3,413,817 A | 12/1968 | Kniel |
| 3,459,678 A | 8/1969 | Hagemeyer et al. |
| 3,584,071 A | 6/1971 | Mcnulty et al. |
| 3,596,473 A | 8/1971 | Streich |
| 3,660,519 A | 5/1972 | Takaaki et al. |
| 3,686,334 A | 8/1972 | Britton |
| 3,686,350 A | 8/1972 | Ono et al. |
| 3,702,886 A | 11/1972 | Argauer et al. |
| 3,862,257 A | 1/1975 | Buben et al. |
| 3,900,526 A | 8/1975 | Johnson et al. |
| 3,931,349 A | 1/1976 | Kuo |
| 4,012,452 A | 3/1977 | Frampton |
| 4,101,600 A | 7/1978 | Zhukov et al. |
| 4,107,224 A | 8/1978 | Dwyer |
| 4,126,645 A | 11/1978 | Collins |
| 4,132,745 A | 1/1979 | Amigues et al. |
| 4,140,504 A | 2/1979 | Campbell et al. |
| 4,314,090 A | 2/1982 | Shewbart et al. |
| 4,329,530 A | 5/1982 | Irvine et al. |
| 4,367,353 A | 1/1983 | Inglis |
| 4,370,156 A | 1/1983 | Goddin, Jr. et al. |
| 4,375,566 A | 3/1983 | Kawamata et al. |
| 4,433,185 A | 2/1984 | Tabak |
| 4,440,956 A | 4/1984 | Couvillion |
| 4,465,887 A | 8/1984 | Schammel |
| 4,481,305 A | 11/1984 | Jorn et al. |
| 4,489,215 A | 12/1984 | Withers |
| 4,554,395 A | 11/1985 | Jones et al. |
| 4,567,307 A | 1/1986 | Jones et al. |
| 4,629,718 A | 12/1986 | Jones et al. |
| 4,751,336 A | 6/1988 | Jezl et al. |
| 4,754,091 A | 6/1988 | Jezl et al. |
| 4,754,093 A | 6/1988 | Jezl et al. |
| 4,777,313 A | 10/1988 | Sofranko et al. |
| 4,814,539 A | 3/1989 | Jezl et al. |
| 4,822,944 A | 4/1989 | Brazdil et al. |
| 4,849,571 A | 7/1989 | Gaffney |
| 4,882,400 A | 11/1989 | Dumain et al. |
| 4,895,823 A | 1/1990 | Kolts et al. |
| 4,900,347 A | 2/1990 | McCue et al. |
| 4,939,311 A | 7/1990 | Washecheck et al. |
| 4,939,312 A | 7/1990 | Baerns et al. |
| 4,962,261 A * | 10/1990 | Abrevaya ................. C07C 2/84 585/500 |
| 4,966,874 A | 10/1990 | Young et al. |
| 5,012,028 A | 4/1991 | Gupta et al. |
| 5,015,799 A | 5/1991 | Walker et al. |
| 5,024,984 A | 6/1991 | Kaminsky et al. |
| 5,025,108 A | 6/1991 | Cameron et al. |
| 5,041,405 A | 8/1991 | Lunsford et al. |
| 5,057,638 A | 10/1991 | Sweeney |
| 5,066,629 A | 11/1991 | Lukey et al. |
| 5,080,872 A | 1/1992 | Jezl et al. |
| 5,118,898 A | 6/1992 | Tyler et al. |
| 5,132,472 A | 7/1992 | Durante et al. |
| 5,137,862 A | 8/1992 | Mackrodt et al. |
| 5,179,056 A | 1/1993 | Bartley |
| 5,196,634 A | 3/1993 | Washecheck et al. |
| 5,198,596 A | 3/1993 | Kaminsky et al. |
| 5,263,998 A | 11/1993 | Mackrodt et al. |
| 5,288,935 A | 2/1994 | Alario et al. |
| 5,292,979 A | 3/1994 | Chauvin et al. |
| 5,306,854 A | 4/1994 | Choudhary et al. |
| 5,312,795 A | 5/1994 | Kaminsky et al. |
| 5,316,995 A | 5/1994 | Kaminsky et al. |
| 5,328,883 A | 7/1994 | Washecheck et al. |
| 5,336,825 A | 8/1994 | Choudhary et al. |
| 5,336,826 A | 8/1994 | Brophy et al. |
| 5,345,023 A | 9/1994 | Chauvin et al. |
| 5,371,306 A | 12/1994 | Woo et al. |
| 5,414,157 A | 5/1995 | Durante et al. |
| 5,414,170 A | 5/1995 | McCue et al. |
| 5,430,219 A | 7/1995 | Sanfilippo et al. |
| 5,449,850 A | 9/1995 | Young et al. |
| 5,462,583 A | 10/1995 | Wood et al. |
| 5,473,027 A | 12/1995 | Batchelor et al. |
| 5,500,149 A | 3/1996 | Green et al. |
| 5,523,493 A | 6/1996 | Cameron et al. |
| 5,568,737 A | 10/1996 | Campbell et al. |
| 5,599,510 A | 2/1997 | Kaminsky et al. |
| 5,659,090 A | 8/1997 | Cameron et al. |
| 5,670,442 A | 9/1997 | Fornasari et al. |
| RE35,632 E | 10/1997 | Leyshon |
| RE35,633 E | 10/1997 | Leyshon |
| 5,679,241 A | 10/1997 | Stanley et al. |
| 5,712,217 A | 1/1998 | Choudhary et al. |
| 5,714,657 A | 2/1998 | DeVries |
| 5,736,107 A | 4/1998 | Inomata et al. |
| 5,744,015 A | 4/1998 | Mazanec et al. |
| 5,749,937 A | 5/1998 | Detering et al. |
| 5,750,821 A | 5/1998 | Inomata et al. |
| 5,763,722 A | 6/1998 | Vic et al. |
| 5,792,895 A | 8/1998 | Commereuc et al. |
| 5,811,618 A | 9/1998 | Wu |
| 5,811,619 A | 9/1998 | Commereuc et al. |
| 5,817,904 A | 10/1998 | Vic et al. |
| 5,817,905 A | 10/1998 | Commereuc et al. |

(56) References Cited

U.S. PATENT DOCUMENTS

| | | |
|---|---|---|
| 5,830,822 A | 11/1998 | Euzen |
| 5,849,973 A | 12/1998 | Van der Vaart |
| 5,856,257 A | 1/1999 | Freeman et al. |
| 5,866,737 A | 2/1999 | Hagemeyer et al. |
| 5,877,363 A | 3/1999 | Gildert et al. |
| 5,897,945 A | 4/1999 | Lieber et al. |
| 5,917,136 A | 6/1999 | Gaffney et al. |
| 5,935,293 A | 8/1999 | Detering et al. |
| 5,935,897 A | 8/1999 | Trubenbach et al. |
| 5,935,898 A | 8/1999 | Trubenbach et al. |
| 5,936,135 A | 8/1999 | Choudhary et al. |
| 5,959,170 A | 9/1999 | Withers |
| 6,020,533 A | 2/2000 | Lewis et al. |
| 6,031,145 A | 2/2000 | Commereuc et al. |
| 6,087,545 A | 7/2000 | Choudhary et al. |
| 6,096,934 A | 8/2000 | Rekoske |
| 6,103,654 A | 8/2000 | Commereuc et al. |
| 6,110,979 A | 8/2000 | Nataraj et al. |
| 6,114,400 A | 9/2000 | Nataraj et al. |
| 6,146,549 A | 11/2000 | Mackay et al. |
| 6,153,149 A | 11/2000 | Rabitz et al. |
| 6,221,986 B1 | 4/2001 | Commereuc et al. |
| 6,355,093 B1 | 3/2002 | Schwartz et al. |
| 6,380,451 B1 | 4/2002 | Kreischer et al. |
| 6,403,523 B1 | 6/2002 | Cantrell et al. |
| RE37,853 E | 9/2002 | Detering et al. |
| 6,447,745 B1 | 9/2002 | Feeley et al. |
| 6,509,292 B1 | 1/2003 | Blankenship et al. |
| 6,518,476 B1 | 2/2003 | Culp et al. |
| 6,576,803 B2 | 6/2003 | Cantrell et al. |
| 6,596,912 B1 | 7/2003 | Lunsford et al. |
| 6,610,124 B1 | 8/2003 | Dolan et al. |
| 6,683,019 B2 | 1/2004 | Gartside et al. |
| 6,726,850 B1 | 4/2004 | Reyes et al. |
| 6,730,808 B2 | 5/2004 | Bitterlich et al. |
| 6,747,066 B2 | 6/2004 | Wang et al. |
| 6,759,562 B2 | 7/2004 | Gartside et al. |
| 6,761,838 B2 | 7/2004 | Zeng et al. |
| 6,764,602 B2 | 7/2004 | Shutt et al. |
| 6,821,500 B2 | 11/2004 | Fincke et al. |
| 6,841,708 B1 | 1/2005 | Benje |
| 6,891,001 B2 | 5/2005 | Kuhlburger |
| 7,093,445 B2 | 8/2006 | Corr, II et al. |
| 7,157,612 B2 | 1/2007 | Ewert et al. |
| 7,176,342 B2 | 2/2007 | Bellussi et al. |
| 7,183,451 B2 | 2/2007 | Gattis et al. |
| 7,199,273 B2 | 4/2007 | Molinier et al. |
| 7,208,647 B2 | 4/2007 | Peterson et al. |
| 7,214,841 B2 | 5/2007 | Gartside et al. |
| 7,250,543 B2 | 7/2007 | Bagherzadeh et al. |
| 7,291,321 B2 | 11/2007 | Bagherzadeh et al. |
| 7,316,804 B2 | 1/2008 | Taheri et al. |
| 7,361,622 B2 | 4/2008 | Benderly et al. |
| 7,473,814 B2 | 1/2009 | Basset et al. |
| 7,576,296 B2 | 8/2009 | Fincke et al. |
| 7,579,509 B2 | 8/2009 | Benje et al. |
| 7,589,246 B2 | 9/2009 | Iaccino et al. |
| 7,659,437 B2 | 2/2010 | Iaccino et al. |
| 7,667,085 B2 | 2/2010 | Gattis et al. |
| 7,671,244 B2 | 3/2010 | Hafenscher et al. |
| 7,683,227 B2 | 3/2010 | Iaccino et al. |
| 7,687,041 B2 | 3/2010 | Singh |
| 7,728,186 B2 | 6/2010 | Iaccino et al. |
| 7,781,636 B2 | 8/2010 | Iaccino et al. |
| 7,795,490 B2 | 9/2010 | Iaccino et al. |
| 7,838,710 B2 | 11/2010 | Ryu |
| 7,868,216 B2 | 1/2011 | Chodorge et al. |
| 7,879,119 B2 | 2/2011 | Abughazaleh et al. |
| 7,888,541 B2 | 2/2011 | Gartside et al. |
| 7,888,543 B2 | 2/2011 | Iaccino et al. |
| 7,902,113 B2 | 3/2011 | Zarrinpashne et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,968,020 B2 | 6/2011 | Behelfer et al. |
| 7,968,759 B2 | 6/2011 | Iaccino et al. |
| 7,977,519 B2 | 7/2011 | Iaccino et al. |
| 8,071,836 B2 | 12/2011 | Butler |
| 8,080,215 B2 | 12/2011 | Taheri et al. |
| 8,129,305 B2 | 3/2012 | Bagherzadeh et al. |
| 8,153,851 B2 | 4/2012 | Gartside et al. |
| 8,227,650 B2 | 7/2012 | Putman et al. |
| 8,232,415 B2 | 7/2012 | Taheri et al. |
| 8,258,358 B2 | 9/2012 | Gartside et al. |
| 8,269,055 B2 | 9/2012 | Fritz et al. |
| 8,277,525 B2 | 10/2012 | Dalton |
| 8,293,805 B2 | 10/2012 | Khan et al. |
| 8,399,527 B1 | 3/2013 | Brown et al. |
| 8,399,726 B2 | 3/2013 | Chinta et al. |
| 8,435,920 B2 | 5/2013 | White et al. |
| 8,450,546 B2 | 5/2013 | Chinta et al. |
| 8,552,236 B2 | 10/2013 | Iaccino |
| 8,624,042 B2 | 1/2014 | Grasset et al. |
| 8,658,750 B2 | 2/2014 | Lattner et al. |
| 8,669,171 B2 | 3/2014 | Perraud et al. |
| 8,710,286 B2 | 4/2014 | Butler |
| 8,729,328 B2 | 5/2014 | Chinta et al. |
| 8,759,598 B2 | 6/2014 | Hayashi et al. |
| 8,796,497 B2 | 8/2014 | Chinta et al. |
| 8,912,381 B2 | 12/2014 | Chinta et al. |
| 8,921,256 B2 | 12/2014 | Cizeron et al. |
| 8,962,517 B2 | 2/2015 | Zurcher et al. |
| 9,133,079 B2 | 9/2015 | Weinberger et al. |
| 9,334,204 B1 | 5/2016 | Radaelli et al. |
| 9,352,295 B2 | 5/2016 | Rafique et al. |
| 9,469,577 B2 | 10/2016 | Schammel et al. |
| 2002/0015670 A1 | 2/2002 | Shah et al. |
| 2003/0072700 A1 | 4/2003 | Goebel et al. |
| 2003/0189202 A1 | 10/2003 | Li et al. |
| 2003/0233019 A1 | 12/2003 | Sherwood |
| 2004/0220053 A1 | 11/2004 | Bagherzadeh et al. |
| 2005/0065391 A1 | 3/2005 | Gattis et al. |
| 2005/0065392 A1 | 3/2005 | Peterson et al. |
| 2006/0155157 A1 | 7/2006 | Zarrinpashne et al. |
| 2006/0283780 A1 | 12/2006 | Spivey et al. |
| 2007/0027030 A1 | 2/2007 | Cheung et al. |
| 2007/0073083 A1 | 3/2007 | Sunley |
| 2007/0083073 A1 | 4/2007 | Bagherzadeh et al. |
| 2008/0141713 A1 | 6/2008 | Verma |
| 2008/0267852 A1 | 10/2008 | Schumacher et al. |
| 2008/0275143 A1 | 11/2008 | Malhotra et al. |
| 2008/0281136 A1 | 11/2008 | Bagherzadeh et al. |
| 2008/0293980 A1 | 11/2008 | Kiesslich et al. |
| 2009/0043141 A1 | 2/2009 | Mazanec et al. |
| 2009/0087496 A1 | 4/2009 | Katusic et al. |
| 2009/0202427 A1 | 8/2009 | Katusic et al. |
| 2009/0259076 A1 | 10/2009 | Simmons et al. |
| 2009/0267852 A1 | 10/2009 | Tahmisian et al. |
| 2010/0000153 A1 | 1/2010 | Kurkjian et al. |
| 2010/0003179 A1 | 1/2010 | Katusic et al. |
| 2010/0185034 A1 | 7/2010 | Nishimura et al. |
| 2010/0191031 A1 | 7/2010 | Sundaram |
| 2010/0197482 A1 | 8/2010 | Basset et al. |
| 2010/0249473 A1 | 9/2010 | Butler |
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0124488 A1 | 5/2011 | Neltner et al. |
| 2011/0160508 A1 | 6/2011 | Ma et al. |
| 2011/0189559 A1 | 8/2011 | Baldanza et al. |
| 2011/0240926 A1 | 10/2011 | Schellen et al. |
| 2011/0257453 A1 | 10/2011 | Chinta et al. |
| 2011/0315012 A1 | 12/2011 | Kuznicki et al. |
| 2012/0041246 A1* | 2/2012 | Scher .............. B01J 21/066 585/500 |
| 2012/0065412 A1 | 3/2012 | Abdallah et al. |
| 2012/0129690 A1 | 5/2012 | Larcher et al. |
| 2012/0172648 A1 | 7/2012 | Seebauer |
| 2012/0197053 A1 | 8/2012 | Cantrell et al. |
| 2012/0198769 A1 | 8/2012 | Schirrmeister et al. |

(56) References Cited

U.S. PATENT DOCUMENTS

| | | |
|---|---|---|
| 2012/0204716 A1 | 8/2012 | Schirrmeister et al. |
| 2012/0215045 A1 | 8/2012 | Butler |
| 2012/0222422 A1 | 9/2012 | Nunley et al. |
| 2013/0023079 A1 | 1/2013 | Kang et al. |
| 2013/0023709 A1 | 1/2013 | Cizeron et al. |
| 2013/0025201 A1 | 1/2013 | Dalton |
| 2013/0040806 A1 | 2/2013 | Dismukes et al. |
| 2013/0042480 A1 | 2/2013 | Turulin |
| 2013/0142707 A1 | 6/2013 | Chinta et al. |
| 2013/0158322 A1 | 6/2013 | Nyce et al. |
| 2013/0165728 A1 | 6/2013 | Zurcher et al. |
| 2013/0178680 A1 | 7/2013 | Ha et al. |
| 2013/0225884 A1 | 8/2013 | Weinberger et al. |
| 2013/0253248 A1 | 9/2013 | Gamoras et al. |
| 2013/0270180 A1 | 10/2013 | Zhang et al. |
| 2014/0012053 A1 | 1/2014 | Iyer et al. |
| 2014/0018589 A1 | 1/2014 | Iyer et al. |
| 2014/0080699 A1 | 3/2014 | Ghose et al. |
| 2014/0107385 A1 | 4/2014 | Schammel et al. |
| 2014/0121433 A1 | 5/2014 | Cizeron et al. |
| 2014/0128484 A1 | 5/2014 | Hassan et al. |
| 2014/0128485 A1 | 5/2014 | Hassan et al. |
| 2014/0171707 A1 | 6/2014 | Nyce et al. |
| 2014/0181877 A1 | 6/2014 | Haykinson et al. |
| 2014/0194663 A1 | 7/2014 | Butler |
| 2014/0249339 A1 | 9/2014 | Simanzhenkov et al. |
| 2014/0274671 A1 | 9/2014 | Schammel et al. |
| 2014/0275619 A1 | 9/2014 | Chen et al. |
| 2014/0378728 A1 | 12/2014 | Davis et al. |
| 2015/0010467 A1 | 1/2015 | Ito et al. |
| 2015/0152025 A1 | 6/2015 | Cizeron et al. |
| 2015/0210610 A1 | 7/2015 | Rafique et al. |
| 2015/0232395 A1 | 8/2015 | Nyce et al. |
| 2015/0307415 A1 | 10/2015 | Rafique et al. |
| 2015/0368167 A1 | 12/2015 | Weinberger et al. |
| 2016/0272556 A1 | 9/2016 | Rafique et al. |
| 2016/0272557 A1 | 9/2016 | Radaelli et al. |
| 2016/0289143 A1 | 10/2016 | Duggal et al. |

FOREIGN PATENT DOCUMENTS

| | | |
|---|---|---|
| CN | 101224432 | 7/2008 |
| CN | 101387019 A | 3/2009 |
| CN | 102093157 A | 6/2011 |
| CN | 102125825 A | 7/2011 |
| DE | 1905517 A1 | 8/1970 |
| DE | 2540257 A1 | 4/1977 |
| DE | 3406751 A1 | 8/1985 |
| DE | 4039960 A1 | 9/1991 |
| DE | 4338414 C1 | 3/1995 |
| DE | 4338416 C1 | 4/1995 |
| EP | 0253522 A2 | 1/1988 |
| EP | 303438 A2 | 2/1989 |
| EP | 608447 A | 8/1994 |
| EP | 0634211 A1 | 1/1995 |
| EP | 0722822 A1 | 7/1996 |
| EP | 0716064 B1 | 7/1998 |
| EP | 1110930 A1 | 6/2001 |
| EP | 0761307 B1 | 2/2003 |
| EP | 0764467 B1 | 2/2003 |
| EP | 1632467 A1 | 3/2006 |
| EP | 1749807 A1 | 2/2007 |
| EP | 1749806 B1 | 10/2008 |
| FR | 649429 A | 12/1928 |
| GB | 733336 A | 7/1955 |
| JP | 2005161225 A | 6/2005 |
| WO | 8607351 A1 | 12/1986 |
| WO | 0204119 A1 | 1/2002 |
| WO | 2004033488 A2 | 4/2004 |
| WO | 2004056479 A1 | 7/2004 |
| WO | 2004103936 A1 | 12/2004 |
| WO | 2005067683 | 12/2006 |
| WO | 2007130515 A2 | 11/2007 |
| WO | 2008005055 A2 | 1/2008 |
| WO | 2008014841 A1 | 2/2008 |
| WO | 2008022147 A1 | 2/2008 |
| WO | 2008073143 A2 | 6/2008 |
| WO | 2009071463 A2 | 6/2009 |
| WO | 2009074203 A1 | 6/2009 |
| WO | 2009115805 A1 | 9/2009 |
| WO | 2010005453 A2 | 1/2010 |
| WO | 2011008464 A1 | 1/2011 |
| WO | 2011041184 A2 | 4/2011 |
| WO | 2011050359 A1 | 4/2011 |
| WO | 2010069488 | 5/2011 |
| WO | 2011149996 A2 | 12/2011 |
| WO | 2012162526 A2 | 11/2012 |
| WO | 2013177433 A2 | 11/2013 |
| WO | 2013177461 A2 | 11/2013 |
| WO | 2014049445 A2 | 4/2014 |
| WO | 2014143880 A1 | 9/2014 |
| WO | 2015105911 A1 | 7/2015 |
| WO | 2015106023 A1 | 7/2015 |

OTHER PUBLICATIONS

Berstad, D. et al., "Low-temperature CO2 removal from natural gas" Energy Procedia (2012) 26:41-48.

Graves, C.R. "Recycling CO2 into Sustainable Hydrocarbon Fuels: Electrolysis of CO2 and H2O" Dissertation, Columbia University (2010).

Gupta, M. "Review on Heat Recovery Unit with Thermoelectric Generators" Intl J Eng and Innov Tech (IJEIT) (2014) 4(4):128-131.

Kaibe, H. et al. "Recovery of Plant Waste Heat by a Thermoelectric Generating System" Komatsu Tech Report (2011) 57(164):26-30.

Li, B. et al. "Advances in CO2 capture technology: A patent review" Applied Energy (2013) 102:1439-1447.

Office action dated Sep. 11, 2015 for U.S. Appl. No. 14/789,946.

Office action dated Sep. 11, 2015 for U.S. Appl. No. 14/789,953.

Ohashi, Y. et al. "Development of Carbon Dioxide Removal System from the Flue Gas of Coal Fired Power Plant" Energy Procedia (2011) 4:29-34.

Seeberger, A. et al. "Gas Separation by Supported Ionic Liquid Membranes" DGMK-Conference, Hamburg, Germany (2007).

Simons, K. "Membrane Technologies for CO2 Capture" Dissertation, U. of Twente (2010).

Suzuki, K. "Toshiba's Activity in Clean Coal and Carbon Capture Technology for Thermal Power Plants" APEC Clean Fossil Energy Technical and Policy Seminar (Feb. 22, 2012).

Weinberger, S. et al. "Process for Separating Hydrocarbon Compounds" U.S. Appl. No. 14/820,460, filed Aug. 6, 2015.

Witek-Krowiak, A. et al. "Carbon Dioxide Removal in a Membrane Contactor-Selection of Absorptive Liquid/Membrane System" Intl J Chem Eng and Appl. (2012) 3(6):391-395.

Xu, G. et al. "An Improved CO2 Separation and Purification System Based on Cryogenic Separation and Distillation Theory" Energies (2014) 7:3484-3502.

Yan, D. "Modeling and Application of a Thermoelectric Generator" Thesis, Univ. Toronto (2011).

Duggal, S. et al. "Advanced Oxidative Coupling of Methane" U.S. Appl. No. 14/868,911, filed Sep. 29, 2015.

International search report and written opinion dated Nov. 11, 2015 for PCT Application No. US2014/067465.

Office action dated Nov. 13, 2015 for U.S. Appl. No. 13/900,898.

Smith, et al. Recent developments in solvent absorption technologies at the CO2CRC in Australia. Energy Procedia 1 (2009): 1549-1555.

"Autothermal Partial Oxidative Coupling of Methane," IP.com, Prior Art Database Technical Disclosure, Jul. 29, 2008, 5 pages.

Barrett, et al. "The determination of pore volume and area distributions in porous substances—Computations from nitrogen isotherms." J. Am. Chem. Soc. (1951) 73:373-380.

Bollmann, et al. "Ethylene tetramerization: a new route to produce 1-octene in exceptionally high selectivities." J Am Chem Soc. (Nov. 17, 2004) 126(45):14712-3.

Botella, et al. "Effect of Potassium Doping on the Catalytic Behavior of Mo—V—Sb Mixed Oxide Catalysts in the Oxidation of Propane to Acrylic Acid." Catalysis Letters (Sep. 2003) 89(3-4):249-253.

(56) References Cited

OTHER PUBLICATIONS

Carter, et al. "High activity ethylene trimerisation catalysts based on diphosphine ligands." Chem Commun (Camb). (Apr. 21, 2002) (8):858-9.
Cavani et al. "Oxidative dehydrogenation of ethane and propane: How far fro commercial implementation?" Catalysis Today (2007) 127:113-131.
Chemsystems PERP Report Ethylene Oxide/Ethylene Glycol 2005.
Chen, et al. "M2 Forming—A Process for Aromatization of Light Hydrocarbons." Ind. Eng. Chem. Process. Des. Dev. (1986) 25:151-155.
Choudhary et al. "Aromatization of dilute ethylene over Ga-modified ZSM-5 type zeolite catalysts" Microporous and Mesoporous Materials (2001) 47:253-267.
Choudhary et al. "Oxidative conversion of methane/natural gas into higher hydrocarbons" Catalysis Surveys from Asia (2004) 8(1):15-25.
Choudhary et al. "Surface basicity and acidity of alkaline earth-promoted La2O3 catalysts and their performance in oxidative coupling of methane" J Chem. Technol. Biotechnol (1998) 72:125-130.
Choudhary, et al. "Aromatization of dilute ethylene over GA-modified ZSM-5 type zeolite catalysts" Microporous and Mesoporous Materials. (2001) 253-267.
Christopher et al. "Engineering selectivity in heterogeneous catalysis: Ag nanowires as selective ethylene epoxidation catalysts" J Am Chem Soc. (2008) 130:11264-11265.
Debart et al., "-MnO2 Nanowires: A Catalyst for the O2 Electrode in Rechargeable Lithium Batteries," Angew. Chem. Int. Ed. (2008) 47:4521-4524.
Enger et al., "A review of catalytic partial oxidation of methane to synthesis gas with emphasis on reaction mechanisms over transition metal catalysts," Applied Catalysis A: General 346:1-27, Aug. 2008.
Gao et al., "A study on methanol steam reforming to CO2 and H2 over the La2CuO4 nanofiber catalyst," Journal of Solid State Chemistry 181:7-13, 2008.
Gao et al., "The direct decomposition of NO over the La2CuO4 nanofiber catalyst," Journal of Solid State Chemistry 181:2804-2807, 2008.
Guo et al. "Current Status and Some Perspectives of Rare Earth Catalytic Materials" J Chinese Rare Earth Soc (2007) 25(1):1-15.
Guo, X. et al. "Direct, Nonoxidative Conversion of Methane to Ethylene, Aromatics, and Hydrogen" Science (2014) 344:616-619.
Huang et al., "Exploiting Shape Effects of La2O3 Nanocatalysts for Oxidative Coupling of Methane Reaction," The Royal Society of Chemistry 2013, 5 pages.
Huang et al., "Exploiting Shape Effects of La2O3 Nanocatalysts for Oxidative Coupling of Methane Reaction," The Royal Society of Chemistry 2013, 7 pages (Electronic Supplementary Information).
International search report and written opinion dated Mar. 6, 2014 for PCT/US2013/042480.
International search report and written opinion dated Jun. 12, 2015 for PCT Application No. US2015/010688.
International search report and written opinion dated Nov. 1, 2013 for PCT/US2013/049742.
International Search Report and Written Opinion dated Mar. 17, 2014 for PCT/US2013/021312.
International search report dated Mar. 19, 2014 for PCT Application No. PCT/US2013/073657.
Kaminsky, M.P. et al. "Deactivation of Li-Based Catalysts for Methane Oxidative Coupling" Poster ACS Symposium on Natural Gas Upgrading II (Apr. 5-10, 1992).
Kaminsky, M.P. et al. "Oxygen X-Ray Absorption Near-Edge Structure Characterization of the Ba-Doped Yttria Oxidative Coupling Catalyst" J Catalysis (1992) 136:16-23.
Keller, et al. Synthesis of Ethylene via Oxidative Coupling of Methane. Journal of Catalysis 73: 9-19, 1982.
Knuuttila, et al. "Advanced Polyethylene Technologies—Controlled Material Properties. Long Term Properties of Polyolefins" Advances in Polymer Science (2004) 169:13-28.
Kuang, et al. "Grafting of PEG onto lanthanum hydroxide nanowires". Materials Letters (2008) 62:4078-4080.
Labinger, "Oxidative Coupling of Methane: An Inherent Limit to Selectivity?" Catalysis Letters (1988) 1:371-376.
Li, et al. "Combined Single-Pass Conversion of Methane Via Oxidative Coupling and Dehydroaromatization." Catalysis Letters (Sep. 2003) 89(3-4):275-279.
Li, et al. Energy and Fuels. (2008) 22: 1897-1901.
Ling et al. "Preparation of Ag_coreAu_core Nanowires and Their Surface Enhanced Raman Spectroscopic Studies" Acta Chem Sinica (2007) 65(9):779-784.
Liu, et al. A novel Na_WO4-Mn.SiC monolithic foam catalyst with improved thermal properties for the oxidative coupling of methane. Catalysis Communications 9: 1302-1306, 2008.
Lunsford, "The Catalytic Oxidative Coupling of Methane," Angew. Chem. Int. Ed. Engl. (1995) 34:970-980.
Lunsford, J.H. "Catalytic conversion of methane to more useful chemicals and fuels: a challenge for the 21st century" Catalysis Today (2000) 63:165-174.
Mimoun, H. et al. "Oxypyrolysis of Natural Gas" Appl Catalysis (1990) 58:269-280.
Mleczko, et al. "Catalytic oxidative coupling of methane—reaction engineering aspects and process schemes" Fuel Processing Tech (1995) 42:217-248.
Natural Gas Spec Sheet, 2003, prepared by Florida Power and Light Company.
Neltner et al. "Production of Hydrogen Using Nanocrystalline Protein-Templated Catalysts on M13 Phage" ACS Nano (2010) 4(6): 3227-3235.
Neltner. Hybrid Bio-templated Catalysts. Doctoral Thesis, Massachusetts Institute of Technology, Jun. 2010, 156 pages.
Nexant/Chemsystems HDPE Report, PERP 09/10-3, Jan. 2011.
Nghiem, XS "Ethylene Production by Oxidative Coupling of Methane: New Process Flow Diagram based on Adsorptive Separation" Berlin, Mar. 14, 2014.
Nielsen, et al. "Treat LPGs with amines." Hydrocarbon Process (1997) 79:49-59.
Niu, et al. "Preparation and Characterization of La2O2CO3 Nanowires with High Surface Areas" J Chinese Rare Earth Soc (Dec. 2005) 23:33-36.
Notice of Allowance dated Jun. 8, 2015 for U.S. Appl. No. 13/739,954.
Nyce, et al., "Ethylene-to-Liquids Systems and Methods", U.S. Appl. No. 14/591,850, filed Jan. 7, 2015.
Nyce, G. et al. PCT/US2015/010525 filed Jan. 7, 2015 for "Ethylene-to-Liquids Systems and Methods".
Office action dated Oct. 23, 2014 for U.S. Appl. No. 13/739,954.
Olah, G. Hydrocarbon Chemistry. 2nd Edition, John Wiley & Sons, 2003.
Pak et al., "Elementary Reactions in the Oxidative Coupling of Methane over Mn/Na2WO4/SiO2 and Mn/Na2WO4/MgO Catalysts," Journal of Catalysis (1998) 179:222-230.
Qiu et al., "Steady-state conversion of methane to aromatics in high yields using an integrated recycle reaction system," Catalysis Letters 48:11-15, 1997.
Radaelli, G. et al. "Efficient Oxidative Coupling of Methane Processes and Systems" U.S. Appl. No. 14/789,953, filed Jul. 1, 2015.
Rafique et al. "Ethylene-to-Liquids Systems and Methods" filed Sep. 15, 2014 as U.S. Appl. No. 62/050,729.
Rafique et al. "Oxidative Coupling of Methane Implementations for Olefin Production" filed Oct. 31, 2014 as U.S. Appl. No. 62/073,478.
Rafique et al. "Oxidative Coupling of Methane Implementations for Olefin Production" U.S. Appl. No. 14/592,668, filed Jan. 8, 2015.
Rafique, H. et al. "Oxidative Coupling of Methane Implementations for Olefin Production" U.S. Appl. No. 14/789,946, filed Jul. 1, 2015.
Rafique, H. et al. PCT/US2015/010688 filed Jan. 8, 2015 for "Oxidative Coupling of Methane Implementations for Olefin Production".
Saito, et al. "Dehydrogenation of Propane Over a Silica-Supported Gallium Oxide Catalyst." Catalysis Letters (Sep. 2003) 89(3-4):213-217.

(56) References Cited

OTHER PUBLICATIONS

Schweer et al., "OCM in a fixed-bed reactor: limits and perspectives," Catalysis Today 21:357-369, 1994.
Sheridan, D. et al. PCT/US2014/067465 filed Nov. 25, 2014 for "Integrated Mixers and Heat Exchangers for Oxidative Coupling Methane Systems".
Somorjai et al., "High technology catalysts towards 100% selectivity Fabrication, characterization and reaction studies," Catalysis Today 100:201-215, 2005.
Sugiyama, et al. "Redox Behaviors of Magnesium Vanadate Catalysts During the Oxidative Dehydrogenation of Propane." Catalysis Letters (Sep. 2003) 89(3-4):229-233.
Takanabe et al., "Mechanistic Aspects and eaction Pathways for Oxidative Coupling of Methane on Mn/Na2WO4/SiO2 Catalysts," J. Phys. Chem. C (2009) 113(23):10131-10145.
Takanabe et al., "Rate and Selectivity Enhancements Mediated by OH Radicals in the Oxidative Coupling of Methane Catalyzed by Mn/Na2WO4/SiO2," Angew. Chem. Int. Ed. (2008) 47:7689-7693.
Tong et al. "Development Strategy Research of Downstream Products of Ethene in Tianjin" Tianjin Economy (1996) 37-40.
Trautmann et al., "Cyrogenic Technology for Nitrogen Rejection from Variable Content Natural Gas," XIV Convencion Internacional de Gas, Caracas, Venezuela May 10-12, 2000. (ref from client).
Wang et al., "Autothermal oxidative coupling of methane on the SrCO3/Sm2O3 catalysts," Catalysis Communications 10(6):807-810, 2009.
Wang et al., "Comparative study on oxidation of methane to ethane and ethylene over Na2WO4—Mn/SiO2 catalysts prepared by different methods," Journal of Molecular Catalysis A: Chemical (2006) 245:272-277.
Wang et al., "Low-temperature selective oxidation of methane to ethane and ethylene over BaCO3/La2O3 catalysts prepared by urea combustion method," Catalysis Communications 7(2):59-63, 2006.
Wong et al., "Oxidative Coupling of Methane Over Alkali Metal Oxide Promoted LA2O3/BACO3 Catalysts," Journal of Chemical Technology and Biotechnology 65(4):351-354, 1996.
Xu, et al. "Maximise ethylene gain and acetylene selective hydrogenation efficiency." Petroleum technology quarterly (2013) 18.3:39-42.
Yang et al., "Anisotropic syntheses of boat-shaped core-shell Au—Ag nanocrystals and nanowires," Nanotechnology 17(9): 2304-2310, 2006.
Yu, C et al. "Oxidative Coupling of Methane over Acceptor-doped SrTiO3: Corelation between p-type Conductivity an dC2 Silectivity and C2 Yield," J. Catalysis (1992) 13(5):338-344.
Zhang, Q. Journal of Natural Gas Chem., (2003) 12:81.
Zhao, X-W, "Technologies and Catalysts for Catalytic Preparation of Ethene," Industrial Catalysis (2004) 12 (Supplement):285-289.
Zhou, M et al., "Functionalization of lanthanum hydroxide nanowires by atom transfer radical polymerization," Nanotechnology (2007) 18(40): 7 pages.
Zhou. "BP-UOP Cyclar Process". Handbook of Petroleum Refining Processes, The McGraw-Hill Companies (2004), pp. 2.29-2.38.
Zimmermann et al., "Ethylene," Ullmann's Encyclopedia of Industrial Chemistry, Wiley-VCH Verlag GmbH & Co. KGaA, Weinheim, Germany, 2009, 66 pages.
European search report and search opinion dated Jan. 20, 2016 for EP Application No. 13817389.3.
Notice of allowance dated Jan. 4, 2016 for U.S. Appl. No. 14/789,953.
Notice of allowance dated Jan. 13, 2016 for U.S. Appl. No. 14/789,946.
Office action dated Jan. 14, 2016 for U.S. Appl. No. 13/936,870.
Office action dated Dec. 23, 2015 for U.S. Appl. No. 13/936,783.
Oil Refinery—Wikipedia, The Free Encyclopedia Website. Jan. 2009.
American Petroleum Institute Publication 534 "Heat Recovery Steam Generators" Jan. 1995 (51 pages).
Co-pending U.S. Appl. No. 15/076,402, filed Mar. 21, 2016.
Co-pending U.S. Appl. No. 15/076,480, filed Mar. 21, 2016.
Notice of allowance dated Apr. 27, 2016 for U.S. Appl. No. 13/900,898.
Office action dated Apr. 22, 2016 for U.S. Appl. No. 15/076,480.
Office action dated May 20, 2016 for U.S. Appl. No. 14/820,460.
Notice of allowance dated Sep. 22, 2016 for U.S. Appl. No. 13/936,870.
International preliminary report on patentability dated Jul. 21, 2016 for PCT Application No. US2015/010688.
International search report and written opinion dated Aug. 11, 2016 for PCT/US2016/024195.
International search report and written opinion dated Aug. 18, 2016 for PCT/US2016/022891.
Notice of allowance dated Aug. 9, 2016 for U.S. Appl. No. 15/076,480.
Notice of allowance dated Aug. 11, 2016 for U.S. Appl. No. 13/900,898.
Notice of allowance dated Aug. 22, 2016 for U.S. Appl. No. 14/820,460.
Co-pending U.S. Appl. No. 15/341,551, filed on Nov. 2, 2016.
Matherne, et al. Chapter 14, Direct Conversion of Methane to C2's and Liquid Fuels: Process Economics, Methane Conversion by Oxidative Processes (1992), 463-482.
Notice of allowance dated Sep. 9, 2016 for U.S. Appl. No. 15/076,480.
Notice of allowance dated Oct. 6, 2016 for U.S. Appl. No. 15,076,480.
Office action dated Oct. 4, 2016 for U.S. Appl. No. 15/076,402.
Office action dated Nov. 7, 2016 for U.S. Appl. No. 13/936,783.
Wang, et al., Critical Influence of BaC03 on Low Temperature Catalytic Activity of BaCO3/Zr02 Catalysts for Oxidative Coupling of Methane, Catalysis Letters (2009), 129:156-162.

\* cited by examiner

OXIDATIVE COUPLING OF METHANE SYSTEMS AND METHODS

CROSS-REFERENCE

This application is a continuation application of U.S. patent application Ser. No. 13/900,898, filed May 23, 2013, which application claims the benefit of U.S. Provisional Patent Application Ser. No. 61/791,312, filed Mar. 15, 2013, U.S. Provisional Patent Application Ser. No. 61/651,485, filed May 24, 2012, each of which is incorporated herein by reference in its entirety.

BACKGROUND

Technical Field

This invention is generally related to vessels and processes useful in an oxidative coupling of methane ("OCM") reaction.

Description of the Related Art

Alkene hydrocarbons are also referred to as 'olefins' within the petrochemical industry and can include any unsaturated hydrocarbon compound containing at least one carbon-to-carbon double bond. Alkenes are used widely within the chemical industry for their general reactivity and ability to polymerize or oligomerize into longer chain hydrocarbon products such as synthetic fuels. Although alkenes are naturally occurring their demand far exceeds the natural supply. Consequently, the vast majority of alkenes are produced via thermal or catalytic cracking of longer chain mixed hydrocarbons such as crude oil or light ends such as napthas. An increasing worldwide demand for longer chain hydrocarbon oils, lubricants and fuels places a demand on hydrocarbon cracking operations to optimize or maximize the formation of longer chain hydrocarbons requiring minimal post-cracking processing to provide such high-demand products. As such, the production of shorter chain alkenes, such as ethylene (IUPAC designation "ethene") using steam or catalytic cracking is in economic tension with the production of generally more valuable longer chain hydrocarbons. Shorter chain alkenes are typically produced using gaseous or liquid light hydrocarbons which are steam cracked at temperatures of 750° C. to 950° C. The cracked gas contains multiple alkene hydrocarbons, including ethylene, and is immediately quenched to halt the numerous secondary (olefin-consuming) free radical reactions within the off-gas. The various alkenes can then be separated from the remaining quenched cracked gas via distillation.

Natural gas is a naturally occurring mixture of hydrocarbon gases including methane and containing up to about twenty percent concentration of higher hydrocarbons such as ethane and small quantities of impurities such as carbon dioxide and hydrogen sulfide. With hundreds of years and trillions of cubic feet of proven, unextracted, natural gas reserves, natural gas potentially provides a rich source of hydrocarbons. Unfortunately, natural gas, or more specifically the methane found in natural gas is expensive to transport for extended distances except by pipeline. Even with the use of pipelines, methane requires significant capital investment in the pipeline itself and incurs significant operational expense in the recompression stations needed to maintain a reasonable pipeline flow. However, restricting transport to pipelines essentially relegates such methane sources to the role of a regional supply, meaning that unless a local demand exists for the methane, the natural gas supply is "stranded"—available for extraction but without a local demand making the extraction economically attractive and practical.

Historically methane has been converted to longer chain hydrocarbons through steam reforming to provide a synthesis gas ("syn-gas"), containing a mixture of carbon monoxide and hydrogen, which is then used as a feedstock to a Fischer-Tropsch process which converts the carbon monoxide and hydrogen into liquid hydrocarbons (often referred to as a "gas-to-liquids" or "GTL" process) that include synthetic lubrication oils and synthetic fuels. While periodically used on a widespread basis, for example by Germany during World War II, the popularity of the Fischer-Tropsch process is hampered by high capital costs associated with the construction of the process, and the high operation and maintenance costs associated with the ongoing operation of the process. However, even with Fischer-Tropsch, the ability to convert methane to short chain alkenes such as ethylene is extremely limited.

Ethylene is widely used in chemical industry, and historically the worldwide production of ethylene has exceeded that of any other organic compound. Ethylene is used in a wide variety of industrial reactions, including: polymerization, oxidation, halogenation and hydrohalogenation, alkylation, hydration, oligomerization, and hydroformylation. Within the United States and Europe, approximately 30% of the ethylene produced is used in the manufacture of three chemical compounds—ethylene oxide which is used as a precursor in the production of ethylene glycol; ethylene dichloride which is used as a precursor in the production of polyvinylchloride; and ethylbenzene which is used as an intermediate in the production of styrene and polystyrene. Significant quantities of ethylene (approx. 60% of total use) are consumed in the production of various forms of polymerized ethylene, or "polyethylene."

The oxidative coupling of methane ("OCM") reaction promotes the formation of alkene hydrocarbons such as ethylene using an exothermic reaction of methane and oxygen over one or more catalysts according to the following equation:

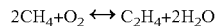

$$2CH_4 + O_2 \leftrightarrow C_2H_4 + 2H_2O$$

The reaction is exothermic ($\Delta H = -67$ kcal/mole) and historically was conducted at very high temperatures of from about 750° C. to about 950° C. to provide a $C_2$ (ethane+ethylene) yield reported to be in the range of 15%-25%. Despite intensive efforts to develop catalysts for the OCM process over the last 30 years, there exists a need for an economic and reliable direct conversion of methane to higher molecular weight hydrocarbons.

The value associated with ethylene production is significant, estimated in excess of $150 billion (US) per year. Used as an intermediate and a raw material feedstock throughout the petrochemical industry, the current ethylene production process via steam cracking consumes greater quantities of energy than nearly all other commodity chemical processes, consumes valuable fractions recovered from crude oil, and is one of the largest contributors to global greenhouse gas ("GHG") emissions in the chemical industry.

BRIEF SUMMARY

Systems and methods for the production of one or more alkene hydrocarbons using a methane source and an oxidant are provided. The methane source and the oxidant are combined over at least one catalyst to provide the one or more alkene hydrocarbons via an oxidative coupling of methane ("OCM") reaction.

Systems for producing at least one higher hydrocarbon, such as a higher alkane, alkene, or other higher hydrocarbon, from a methane source and an oxidant are provided. The systems include at least one vessel having at least one catalyst disposed at least partially within the vessel. The at least one catalyst is configured to catalyze the exothermic reaction of at least a portion of a methane source and at least a portion of an oxidant to provide an oxidative coupling of methane ("OCM") gas including at least one alkene hydrocarbon. The at least one vessel can further include at least one fluid connection configured to receive at least one of a portion of the methane source and a portion of the oxidant and at least one fluid connection configured to remove at least a portion of the oxidative coupling of methane gas.

The system includes at least one thermal adjustment system configured to maintain a thermal profile about the at least one catalyst.

The systems may include a second thermal adjustment system fluidly coupled to the at least one fluid connection configured to receive at least a portion of the oxidant. The second thermal adjustment system may include a non-contact heat transfer unit configured to transfer thermal energy from a heat source to at least a portion of the oxidant. The second thermal adjustment system may also include at least one fluid connection configured to receive at least a portion of the oxidant, at least one fluid connection configured to remove at least a portion of the oxidant from the second thermal adjustment system, the at least one fluid connection configured to remove at least a portion of the oxidant from the second thermal adjustment system fluidly coupled to the at least one fluid connection on the at least one vessel configured to receive at least a portion of the oxidant, at least one fluid connection configured to receive at least a portion of the thermal transfer fluid, and at least one connection configured to remove at least a portion of the heat source. The at least one fluid connection configured to receive at least a portion of the heat source may be configured to receive at least a portion of the oxidative coupling of methane gas removed from the at least one vessel. The second thermal adjustment system heat source may include a combustion heater and the second thermal adjustment system including a combustion heater may further include at least one fluid connection configured to receive at least a portion of the oxidant and at least one fluid connection configured to remove at least a portion of the oxidant from the second thermal adjustment system, the at least one fluid connection configured to remove at least a portion of the oxidant from the second thermal adjustment system fluidly coupled to the at least one fluid connection on the at least one vessel configured to receive at least a portion of the oxidant.

The system may further include a third thermal adjustment system fluidly coupled to the at least one fluid connection on the at least one vessel that is configured to receive at least a portion of the methane source. The third thermal adjustment system may include at least one non-directly contacted heat transfer unit configured to transfer thermal energy from a heat source to at least a portion of the methane source. The third thermal adjustment system may also include at least one fluid connection configured to receive at least a portion of the methane source, at least one fluid connection configured to remove at least a portion of the methane source fluidly coupled to the at least one fluid connection on the at least one vessel configured to receive at least a portion of the methane source, at least one fluid connection configured to receive at least a portion of the heat source and at least one connection configured to remove at least a portion of the heat source. The at least one fluid connection configured to receive at least a portion of the heat source may be configured to receive at least a portion of the oxidative coupling of methane gas removed from the at least one vessel. The third thermal adjustment system may include a combustion heater and the third thermal adjustment system including a combustion heater may also include at least one fluid connection configured to receive at least a portion of the methane source and at least one fluid connection configured to remove at least a portion of the methane source from the third thermal adjustment system, the at least one fluid connection configured to remove at least a portion of the methane source from the third thermal adjustment system fluidly coupled to the at least one fluid connection on the at least one vessel configured to receive at least a portion of the methane source.

The system may also include a fourth thermal adjustment system fluidly coupled to the at least one fluid connection on the at least one vessel that is configured to remove at least a portion of the oxidative coupling of methane gas. The fourth thermal adjustment system may include at least one non-contact heat transfer unit configured to transfer thermal energy from the oxidative coupling of methane gas. The fourth thermal adjustment system may also include at least one fluid connection configured to receive at least a portion of the oxidative coupling of methane gas fluidly coupled to the at least one fluid connection configured to remove at least a portion of the oxidative coupling of methane gas on the at least one vessel, at least one fluid connection configured to remove at least a portion of the oxidative coupling of methane gas from the fourth thermal adjustment system, at least one fluid connection configured to receive at least a portion of a coolant, and at least one connection configured to remove at least a portion of the coolant.

At least a portion of the at least one catalyst may include at least one nanowire catalyst. The at least one nanowire catalyst may include a nanowire catalyst having a substantially similar chemical composition and at least a portion of the substantially similar chemical composition nanowire catalyst may include more than one physical form. The more than one physical form may include at least two of: the substantially similar chemical composition nanowire catalyst deposited on a rigid substrate; the substantially similar chemical composition nanowire catalyst combined with at least one inert material; and the substantially similar chemical composition nanowire catalyst formed into a shape. The substantially similar chemical composition nanowire catalyst may include one or more nanowire catalysts selected from the group consisting of: a metal oxide, a metal hydroxide, a metal oxyhydroxide, a perovskite, a metal oxycarbonate, a metal carbonate, a metal element from any of Groups 1 through 7, a lanthanide, an actinide, or combinations thereof. In some embodiments, one or more dopants comprising a metal element, a semi-metal element, a non-metal element or combinations thereof may be added or otherwise incorporated into the one or more catalysts.

The at least one nanowire catalyst may include one or more nanowire catalysts having a plurality of unique chemical compositions and at least a portion of the nanowire catalysts include more than one physical form. The more than one physical form may include at least two of: the nanowire catalyst deposited on a rigid substrate; the nanowire catalyst combined with at least one inert material; and the nanowire catalyst formed into a shape. The nanowire catalysts may have a plurality of unique chemical composition comprising two or more nanowire catalysts selected from the following: a metal oxide, a metal hydroxide, a metal oxyhydroxide, a metal oxycarbonate, a metal carbonate, a metal element from any of Groups 1 through 7, a lanthanide, an actinide, or combinations thereof. In some embodiments, one or more dopants comprising a metal element, a semi-metal element, a non-metal element or combinations thereof may be added or otherwise incorporated into the one or more catalysts.

The at least one vessel may include a plurality of serially coupled vessels and the at least one connection configured to remove at least a portion of the oxidative coupling of methane gas of a first vessel may be fluidly coupled to at least one connection configured to receive at least a portion of the methane source and at least a portion of the oxidant of a second vessel. The system may also include a fluid connection configured to receive at least a portion of the oxidant disposed between two vessels in the plurality of serially coupled vessels.

The at least one thermal adjustment system may include a plurality of thermal adjustment systems and each of the plurality of thermal adjustment systems may be configured to maintain the thermal profile about the at least one catalyst in at least a portion of the plurality of serially coupled vessels. Each of the plurality of thermal adjustment systems may be configured to maintain a substantially adiabatic profile about the at least one catalyst in a portion of the plurality of serially coupled vessels. Each of the thermal adjustment systems may include a non-contact heat transfer unit configured to transfer thermal energy from the oxidative coupling of methane gas to a coolant and each of the non-contact heat transfer units includes: at least one fluid connection configured to receive at least a portion of the coolant, at least one fluid connection configured to remove at least a portion of the coolant, at least one fluid connection configured to receive at least a portion of the oxidative coupling of methane gas, and at least one connection configured to remove at least a portion of the oxidative coupling of methane gas. In some embodiments, the non-contact heat transfer units may include a "fire tube" boiler (i.e., a boiler having the thermal energy supply/hot fluid inside the tubes and boiling water/steam outside tubes).

At least a portion of the plurality of serially coupled vessels may further include an internal structure configured to support at least one catalyst bed. At least a portion of the at least one catalyst may include at least one nanowire catalyst. The at least one nanowire catalyst may include a nanowire catalyst having a substantially similar chemical composition and at least a portion of the substantially similar chemical composition nanowire catalyst may include more than one physical form. The one or more physical forms can include at least one of: the substantially similar chemical composition nanowire catalyst deposited on a rigid substrate; the substantially similar chemical composition nanowire catalyst combined with at least one inert material; and the substantially similar chemical composition nanowire catalyst formed into a shape. The substantially similar chemical composition nanowire catalyst may include a nanowire catalyst selected from the group consisting of: a metal oxide, a metal hydroxide, a metal oxyhydroxide, a metal oxycarbonate, a metal carbonate, a metal element from any of Groups 1 through 7, a lanthanide, an actinide, or combinations thereof. In some embodiments, one or more dopants comprising a metal element, a semi-metal element, a non-metal element or combinations thereof may be added or otherwise incorporated into the one or more catalysts.

The at least one nanowire catalyst may include a plurality of nanowire catalysts having a plurality of unique chemical compositions and at least a portion of the plurality of nanowire catalysts may include more than one physical form. The more than one physical form may include at least one of: the nanowire catalyst deposited on a rigid substrate; the nanowire catalyst combined with at least one inert material; and the nanowire catalyst formed into a shape.

The at least one vessel may further include an internal structure configured to support a plurality of catalyst beds within all or a portion of the at least one vessel. The at least one vessel may further include at least one fluid connection disposed between at least a portion of adjacent catalyst beds forming the plurality of catalyst beds and configured to receive at least a portion of the oxidant. The one or more thermal adjustment systems may be configured to maintain a substantially adiabatic profile about one or more catalyst beds in the at least one vessel and at least a portion of the one or more thermal adjustment systems may be disposed remote from at least one vessel and the at least one vessel may further include at least one fluid connection disposed between at least a portion of adjacent catalyst beds forming the plurality of catalyst beds and configured to remove at least a portion of the oxidative coupling of methane gas from the at least one vessel and at least one fluid connection disposed between at least a portion of adjacent catalyst beds forming the plurality of catalyst beds and configured to receive at least a portion of the oxidative coupling of methane gas removed from the at least one vessel.

The one or more thermal adjustment systems may include a non-contact heat transfer unit configured to transfer thermal energy from the oxidative coupling of methane gas to a coolant and include: at least one fluid connection configured to receive at least a portion of the coolant; at least one fluid connection configured to remove at least a portion of the coolant; at least one fluid connection configured to receive at least a portion of the oxidative coupling of methane gas; and at least one connection configured to remove at least a portion of the oxidative coupling of methane gas. In some embodiments, the one or more thermal adjustment systems may include a "fire tube" boiler.

At least a portion of the at least one catalyst may include at least one nanowire catalyst. The at least one nanowire catalyst may include a nanowire catalyst having a substantially similar chemical composition; and at least a portion of the substantially similar chemical composition nanowire catalyst may include more than one physical form. The more than one physical form may include at least one of: the substantially similar chemical composition nanowire catalyst deposited on a rigid substrate; the substantially similar chemical composition nanowire catalyst combined with at least one inert material; and the substantially similar chemical composition nanowire catalyst formed into a shape. The single composition nanowire catalyst comprises a nanowire catalyst selected from the group consisting of: a metal oxide, a metal hydroxide, a metal oxyhydroxide, a metal oxycarbonate, a metal carbonate, a metal elements from any of Groups 1 through 7, a lanthanide, an actinide, or combinations thereof. In some embodiments, one or more dopants comprising a metal element, a semi-metal element, a non-metal element or combinations thereof may be added or otherwise incorporated into the one or more catalysts.

The at least one nanowire catalyst may include a plurality of nanowire catalysts and at least a portion of the plurality of nanowire catalysts may have differing chemical compositions and at least a portion of the plurality of nanowire catalysts may include one or more physical forms. The one or more physical forms may include at least one of: the single composition nanowire catalyst deposited on a rigid substrate; the single composition nanowire catalyst combined with at least one inert material; and the single composition nanowire catalyst formed into a shape. In some instances, the nanowire catalyst may be deposited or wash coated onto a porous substrate.

In at least some embodiments, the at least one vessel may be configured to react the methane source and the oxidant to provide the OCM gas under substantially isothermal conditions. The at least one vessel may include a vessel including at least one tube where some or all of an interior portion of the at least one tube is configured to at least partially receive the at least one catalyst; and where a void exists between an exterior portion of the at least one tube and the vessel, the void being structured to receive a thermal transfer medium and contact the thermal transfer medium with the exterior portion of the at least one tube. Some or all the interior portion of the at least one tube may be configured to at least partially receive a chemically inert material. The at least one tube may include an inlet for receiving the methane source and the oxidant and an outlet for removing the oxidative coupling of methane gas; and the void may include: at least one fluid connection configured to receive the thermal transfer medium, the at least one fluid connection proximate the outlet of the at least one tube; at least one fluid connection configured to remove the thermal transfer medium, the at least one fluid connection proximate the inlet of the at least one tube.

The at least one catalyst may include a catalyst having a substantially similar chemical composition; and the at least one catalyst can comprise a nanowire catalyst having at least one physical configuration, the physical configuration comprising at least one of: a nanowire catalyst disposed on the surface of a structural support member; a nanowire catalyst formed into a plurality of shaped members, each of the plurality of shaped members having a similar nanowire catalyst composition; and a nanowire catalyst formed into a plurality of shaped members, at least a portion of the plurality of shaped members having a dissimilar nanowire catalyst composition.

The at least one catalyst in the at least one tube may include a nanowire catalyst having a substantially similar chemical composition; and the nanowire catalyst includes at least one of: a metal oxide, a metal hydroxide, a metal oxyhydroxide, a metal oxycarbonate, a metal carbonate, a metal element from any of Groups 1 through 7, a lanthanide, an actinide, or combinations thereof. In some embodiments, one or more dopants comprising a metal element, a semi-metal element, a non-metal element or combinations thereof may be added or otherwise incorporated into the one or more catalysts.

The at least one catalyst may include a plurality of catalysts, each having differing chemical compositions; and the at least one catalyst comprises a plurality of nanowire catalysts having more than one physical configuration, the more than one physical configuration comprises at least two of: a nanowire catalyst disposed on the surface of a structural support member; a nanowire catalyst formed into a plurality of shaped members, each of the plurality of shaped members having a similar nanowire catalyst composition; and a nanowire catalyst formed into a plurality of shaped members, at least a portion of the plurality of shaped members having a dissimilar nanowire catalyst composition.

The at least one catalyst in the at least one tube may include a plurality of nanowire catalysts, each of the plurality of nanowire catalysts having differing chemical compositions; and the plurality of nanowire catalysts includes at least two of a metal oxide, a metal hydroxide, a metal oxyhydroxide, a metal oxycarbonate, a metal carbonate, a metal element from any of Groups 1 through 7, a lanthanide, an actinide, or combinations thereof. In some embodiments, one or more dopants comprising a metal element, a semi-metal element, a non-metal element or combinations thereof may be added or otherwise incorporated into the one or more catalysts.

The at least one tube may be disposed in a substantially vertical configuration and may further comprise a permeable obstruction configured to selectively maintain the at least one catalyst within the at least one tube. The at least one tube may have a diameter that is constant along its length or the at least one tube may have a diameter that changes along a length of the tube.

Systems for producing at least one alkene hydrocarbon from a methane source and an oxidant are provided. The systems may include a plurality of serially coupled vessels including at least a first vessel and a last vessel. Each of the serially coupled vessels may include: at least one catalyst disposed at least partially within each of the serially coupled vessels, the at least one catalyst configured to catalyze the exothermic reaction of at least a portion of a methane source and at least a portion of an oxidant to provide an oxidative coupling of methane gas including at least one alkene hydrocarbon. The system may further include at least one fluid connection configured to introduce at least a portion of at least one of the methane source and the oxidant; and at least one fluid connection configured to remove at least a portion of the oxidative coupling of methane gas. The system may further include at least one thermal adjustment system fluidly coupled between each of the plurality of serially coupled vessels. Each thermal adjustment system may include a number of fluid connections, including at least one fluid connection configured to admit oxidative coupling of methane ("OCM") gas to the thermal adjustment system, for example to admit OCM gas from one or more preceding vessels. The thermal adjustment system also includes at least one fluid connection configured to permit the OCM gas to exit the thermal adjustment system, for example to permit the OCM gas to exit the thermal adjustment system and flow to a succeeding vessel. Each thermal adjustment system also includes at least one fluid connection configured to introduce at least a portion of a coolant; and at least one fluid connection configured to remove at least a portion of the coolant.

The system may further include at least one second thermal adjustment system fluidly coupled to at least one fluid connection configured to receive at least a portion of the oxidant. The at least one second thermal adjustment system may include a non-contact heat transfer unit configured to transfer thermal energy from a heat source to at least a portion of the oxidant. The second thermal adjustment system may further include at least one fluid connection configured to receive at least a portion of the oxidant; at least one fluid connection configured to remove at least a portion of the oxidant, the at least one fluid connection configured to remove at least a portion of the oxidant fluidly coupled to the at least one fluid connection configured to receive at least a portion of the oxidant on the at least one vessel; at least one fluid connection configured to receive at least a portion of the heat source; and at least one connection configured to remove at least a portion of the heat source.

Each of the plurality of serially coupled vessels can include at least one fluid connection configured to receive at least a portion of the heat source and may also be configured to receive at least a portion of the oxidative coupling of methane gas removed from the last vessel.

The system can also include a third thermal adjustment system fluidly coupled to the at least one fluid connection configured to receive at least a portion of the methane source on the at least one vessel. In some embodiments, the third thermal adjustment system may include at least one non-contact heat transfer unit configured to transfer thermal energy to at least a portion of the methane source. In some instances, the third thermal adjustment system may further include: at least one fluid connection configured to receive at least a portion of the methane source; at least one fluid connection configured to remove at least a portion of the methane source, the at least one fluid connection configured to remove at least a portion of the methane source fluidly coupled to the at least one fluid connection configured to receive at least a portion of the methane source on the at least one vessel; at least one fluid connection configured to receive at least a portion of a heat source; and at least one connection configured to remove at least a portion of the heat source.

The system may also be configured such that the at least one fluid connection configured to receive at least a portion of a heat source may be configured to receive at least a portion of the oxidative coupling of methane gas removed from the at least one vessel. A combustion heater may be used to provide at least a portion of the thermal energy transferred to at least a portion of the methane source. The third thermal adjustment system may further include: at least one fluid connection configured to receive at least a portion of the methane source; and at least one fluid connection configured to remove at least a portion of the methane source, the at least one fluid connection configured to remove at least a portion of the methane source fluidly coupled to the at least one fluid connection configured to receive at least a portion of the methane source on the at least one vessel.

The system may also include a fourth thermal adjustment system fluidly coupled to the at least one fluid connection configured to remove at least a portion of the oxidative coupling of methane gas on the last vessel. The fourth thermal adjustment system comprises a non-contact thermal transfer unit and may include: at least one fluid connection configured to receive the oxidative coupling of methane gas; at least one fluid connection configured to remove the oxidative coupling of methane gas; at least one fluid connection configured to receive a boiler feed water; and at least one fluid connection configured to remove at least one of a heated boiler feed water, a steam having a pressure of 150 psig or less, and a steam having a pressure of greater than 150 psig.

A fluid connection configured to receive at least a portion of the oxidant, may be disposed between two adjoining vessels in the plurality of serially coupled vessels. In some embodiments, each of the plurality of thermal adjustment systems are configured to maintain the thermal profile about the at least one catalyst in at least a portion of each of the plurality of serially coupled vessels. Each of the plurality of thermal adjustment systems may be configured to maintain a substantially adiabatic profile about the at least one catalyst in each of the portion of the plurality of serially coupled vessels. Each of the thermal adjustment systems may include a non-contact heat transfer unit configured to transfer thermal energy to a coolant. In some embodiments, each of the non-contact heat transfer units may include a "fire tube" boiler.

In some instances, at least a portion of the plurality of serially coupled vessels may further include an internal structure configured to support at least one catalyst bed. In some instances, at least a portion of the plurality of serially coupled vessels may be useful for additional chemical processing, for example steam or thermally cracking of the OCM gas to preferentially increase the concentration of one or more targeted hydrocarbons such as ethylene. At least a portion of the at least one catalyst disposed in each of the serially coupled vessels may include at least one nanowire catalyst. The at least one nanowire catalyst may include a nanowire catalyst having a substantially similar chemical composition and wherein at least a portion of the single composition nanowire catalyst includes more than one physical form. The catalyst may have more than one physical form, and the more than one physical form may include at least two of: the single composition nanowire catalyst deposited on a rigid substrate; the single composition nanowire catalyst combined with at least one inert material; and the single composition nanowire catalyst formed into a shape. The single composition nanowire catalyst comprises a nanowire catalyst may be selected from the group consisting of: a metal oxide, a metal hydroxide, a metal oxyhydroxide, a metal oxycarbonate, a perovskite, a metal carbonate, a metal element from any of Groups 1 through 7, a lanthanide, an actinide, or combinations thereof. In some embodiments, one or more dopants comprising a metal element, a semi-metal element, a non-metal element or combinations thereof may be added or otherwise incorporated into the one or more catalysts.

The at least one nanowire catalyst disposed in each of the serially coupled vessels may include nanowire catalysts having a plurality of unique chemical compositions and at least a portion of the nanowire catalysts may include more than one physical form including at least two of: the single composition nanowire catalyst deposited on a rigid substrate; the single composition nanowire catalyst combined with at least one inert material; and the single composition nanowire catalyst formed into a shape.

Methods for producing at least one alkene hydrocarbon from a methane source and an oxidant are also provided. The methods may include introducing a methane source and an oxidant to at least one vessel including at least one catalyst disposed at least partially within the vessel, the at least one catalyst configured to catalyze an exothermic reaction of at least a portion of the methane source and at least a portion of the oxidant to provide an oxidative coupling of methane ("OCM") gas including at least one alkene hydrocarbon, removing at least a portion of the oxidative coupling of methane ("OCM") gas from the at least one vessel; and maintaining a thermal profile across the at least one catalyst using at least one thermal adjustment system.

Introducing a methane source to the at least one vessel may include introducing to the at least one vessel a methane containing gas having a methane concentration of greater than 5 mol %. In some embodiments, the methane source may contain nitrogen. In some instances, introducing a methane source to the at least one vessel may include introducing to the at least one vessel a methane containing gas having a nitrogen concentration of less than 50 mol %.

Introducing an oxidant to the at least one vessel can include introducing an oxidant containing purified oxygen to the at least one vessel, in some instances the oxidant can include a methane containing gas having an oxygen concentration of greater than 5 mol %. In some instances, air can form at least a portion of the oxidant, and introducing an oxidant to the at least one vessel can include introducing to the at least one vessel an oxygen containing gas having a nitrogen concentration of greater than about 50 mol % and an oxygen concentration of less than about 30 mol %. In some instances a highly purified oxygen can form at least a portion of the oxidant and introducing an oxidant to the at least one vessel can include introducing to the at least one vessel an oxygen containing gas having an oxygen concentration of greater than about 30 mol % and a nitrogen concentration of less than about 5 mol %.

Within the at least one vessel an oxidative coupling of methane ("OCM") gas can be formed. Removing at least a portion of the oxidative coupling of methane ("OCM") gas from the at least one vessel can include removing from the at least one vessel an oxidative coupling of methane ("OCM") gas having an ethylene concentration of greater than 0.5 mol %. The OCM gas may also contain ethane. Removing at least a portion of the oxidative coupling of methane ("OCM") gas from the at least one vessel may also include removing from the at least one vessel an oxidative coupling of methane ("OCM") gas having an ethane concentration of greater than 0.5 mol %. The ethane may be separated from the OCM gas. The method may also include separating at least a portion of the ethane from the oxidative coupling of methane gas to provide a separated ethane having an ethane concentration of greater than about 90 mol %. In some instances, at least a portion of the separated ethane may be recycled to the at least one vessel, or to another point in the overall process stream. In some instances, at least a portion of the separated ethane may be further processed, for example, through one or more operations such as steam cracking, catalytic oxidative dehydrogenation, non-oxidative dehydrogenation, or non-oxidative catalytic cracking, to provide one or more targeted unsaturated hydrocarbons such as ethylene.

The at least one vessel may be maintained at a temperature of less than about 900° C. The at least one vessel may be injected at a pressure of less than about 100 psig within the at least one vessel. The gas hour space velocity (volume of gas flow through the vessel at standard conditions divided by vessel volume) may include maintaining the methane source and the oxidant within the at least one vessel to provide a combined gas hour space velocity (GHSV) of less than about 200,000 hr$^{-1}$; less than about 100,000 hr$^{-1}$, less than about 75,000 hr$^{-1}$; less than about 50,000 hr$^{-1}$; less than about 40,000 hr$^{-1}$; less than about 30,000 hr$^{-1}$; less than about 20,000 hr$^{-1}$; less than about 10,000 hr$^{-1}$; less than about 5,000 hr$^{-1}$; less than about 3,000 hr$^{-1}$; or less than about 1,000 hr$^{-1}$.

The OCM gas may also contain unreacted methane, and removing at least a portion of the oxidative coupling of methane ("OCM") gas from the at least one vessel may include removing from the at least one vessel an oxidative coupling of methane ("OCM") gas having a methane concentration of less than 70 mol %, and in certain embodiments, less than 50 mol %. The methane in the OCM gas may be separated from the OCM gas. At least a portion of the methane may be separated from the oxidative coupling of methane gas to provide a separated methane having an methane concentration of greater than about 90 mol %; and at least a portion may be recycled to the at least one vessel.

The methane introduced to the at least one vessel may be converted to an alkene hydrocarbon. In some instances about 5% or more by volume of the methane introduced to the at least one vessel via the methane source may be converted to an alkene hydrocarbon including ethylene. The methane source may be maintained at a temperature greater than about 500° C. prior to introducing the methane source to the at least one vessel. The methane source may be maintained at a pressure at or below about 100 psig prior to introducing the methane source to the at least one vessel.

The oxidant may be maintained at a temperature at or above about 450° C. prior to introducing the oxidant to the at least one vessel. The oxidant may be maintained at a pressure of about 60 psig prior to introducing the oxidant to the at least one vessel.

The oxidative coupling of methane ("OCM") gas removed from the at least one vessel may be at a temperature at or above about 500° C. after removing the oxidative coupling of methane gas from the at least one vessel. The OCM gas removed from the at least one vessel may be at a pressure at or below about 15 psig after removing the oxidative coupling of methane gas from the at least one vessel.

A thermal profile may be established across the catalyst bed in each of the at least one vessels. In some instances, maintaining a thermal profile across the at least one catalyst using at least one thermal adjustment system may include maintaining a substantially adiabatic thermal profile across the at least one catalyst. Thermal energy liberated by the exothermic reaction may be removed from the OCM gas removed from each of the at least one vessels. In some instances, transferring at least a portion of a thermal energy in the oxidative coupling of methane gas removed from the at least one vessel may include transferring the thermal energy to a cooling medium in each of a plurality of thermal adjustment systems, where the at least one vessel includes a plurality of serially coupled vessels and each of the plurality of thermal adjustment systems is disposed between two of the plurality of serially coupled vessels.

Each of the plurality of thermal adjustment systems may include at least one non-contact heat exchanger and transferring at least a portion of a thermal energy in the oxidative coupling of methane gas to a cooling medium in each of a plurality of thermal adjustment systems may include transferring a thermal energy in the oxidative coupling of methane gas to a boiler feed water within each of the thermal adjustment systems to generate a steam, The generated steam may be removed from each of the plurality of thermal adjustment systems.

The method can further include introducing an intermediate oxidant between at least two of the plurality of serially coupled vessels. In at least some instances, introducing an intermediate oxidant between at least two of the plurality of serially coupled vessels comprises introducing between at least two of the plurality of serially coupled vessels an intermediate oxidant including oxygen containing gas having a nitrogen concentration of at least about 50 mol % and an oxygen concentration of at most about 30 mol %. In at least some instances introducing an intermediate oxidant between at least two of the plurality of serially coupled vessels comprises introducing between at least two of the plurality of serially coupled vessels an intermediate oxidant including oxygen containing gas having an oxygen concentration of at least about 30 mol % and a nitrogen concentration of at most about 5 mol %. In at least some instances, introducing an intermediate oxidant between at least two of the plurality of serially coupled vessels comprises introducing between at least two of the plurality of serially coupled vessels an intermediate oxidant having a temperature less than the temperature of the oxidative coupling of methane ("OCM") gas removed from a first of the serially coupled vessels.

A thermal profile may be established across the catalyst bed in each of the at least one vessels. Establishing a thermal profile across the catalyst bed may, in some instances, include maintaining a thermal profile across the at least one catalyst using at least one thermal adjustment system which may include passing at least a portion of the oxidative coupling of methane ("OCM") gas removed from the at least one vessel through the at least one thermal adjustment system, introducing a coolant into the at least one thermal adjustment system, transferring at least a portion of a thermal energy from the oxidative coupling of methane ("OCM") gas removed from the at least one vessel to the coolant; and removing from the at least one thermal adjustment system the coolant containing at least a portion of the thermal energy removed from the oxidative coupling of methane ("OCM") gas removed from the at least one vessel.

The at least one thermal adjustment system can include at least one non-contact heat exchanger and the method may include introducing at least one of boiler feed water, the oxidant, the methane source, or a fluid cooling medium to provide a cooling medium to one or more non-contact heat exchangers. At least a portion of a thermal energy from the oxidative coupling of methane ("OCM") gas removed from the at least one vessel can be transferred to the cooling medium.

A thermal profile may be maintained across the catalyst bed in some or all of the one or more vessels. In at least some instances, maintaining a thermal profile across the at least one catalyst using at least one thermal adjustment system may include maintaining a substantially isothermal thermal profile across the at least one catalyst. Maintaining a substantially isothermal profile can include providing a heat transfer surface within the at least one vessel, the heat transfer surface disposed at least partially between the at least one catalyst and a coolant and configured to pass at least a portion of a heat generated by the exothermic reaction to the coolant, introducing the coolant to the at least one vessel, and removing the coolant from the at least one vessel.

In at least a portion of the at least one vessels, a heat transfer surface may be used to maintain the isothermal profile. The heat transfer surface may be disposed at least partially between the at least one catalyst and a coolant and configured to pass at least a portion of a heat generated by the exothermic reaction to the coolant. The catalyst may be disposed within an interior portion of a tube and at least a portion of the coolant may be disposed on an exterior surface of the tube opposite the interior portion of the tube containing the at least one catalyst, where the interior portion of the tube in contact with the at least one catalyst forms at least a portion of the heat transfer surface. A coolant may be introduced to the at least one vessel. Introducing the coolant to the at least one vessel may include introducing a thermal transfer medium including at least one of: a heat transfer fluid and a molten salt (e.g., nitrates and nitrites of potassium and sodium, non-chlorine containing salts, and eutectic salt mixtures) to the at least one vessel and removing the coolant from the at least one vessel may include removing a thermal transfer medium including at least one of: a heat transfer fluid and a molten salt from the at least one vessel.

Methods for controlling the systems are also provided. An example method of controlling the production of one or more alkene hydrocarbons generated by the exothermic reaction of a methane source containing methane and an oxidant containing oxygen over at least one catalyst to provide an oxidative coupling of methane ("OCM") gas including the one or more alkene hydrocarbons may include monitoring a concentration of the one or more alkene hydrocarbons in the oxidative coupling of methane ("OCM") gas and responsive to a deviation in the concentration of the one or more alkene hydrocarbons in the oxidative coupling of methane ("OCM") gas from a predetermined threshold, performing at least one of the following:
a) adjusting a quantity or concentration of the methane over the at least one catalyst;
b) adjusting a quantity or concentration of the oxygen over the at least one catalyst;
c) adjusting a proportion between the quantity of oxygen and the quantity of methane over the at least one catalyst;
d) adjusting a temperature of the methane source;
e) adjusting a temperature of the oxidant;
f) adjusting a rate of temperature increase of a quantity of the at least one catalyst; and
g) adjusting an overall temperature increase through a quantity of the at least one catalyst.

In some instances, adjusting a proportion between the quantity of oxygen and the quantity of methane may include adjusting either of the quantity of oxidant or the quantity of the methane source to maintain a stoichiometric ratio between the methane and the oxygen such that the oxygen is a limiting reagent. Adjusting a proportion between the quantity of oxygen and the quantity of methane may include adjusting either of the quantity of oxidant or the quantity of the methane source to maintain a stoichiometric ratio between the methane present in the methane source and the oxygen present in the oxidant such that the methane and the oxygen are in a stoichiometric balance.

In some instances, adjusting a temperature of the methane source may include adjusting, such that the temperature of the methane source is at about 600° C. or less, at least one of: (a) a fuel to a combustion heater used to transfer thermal energy to the methane source; and (b) a thermal transfer fluid used to transfer thermal energy via at least one non-contact heat exchanger to the methane source. The thermal transfer fluid can include at least one of: a portion of the oxidative coupling of methane ("OCM") gas; a saturated steam; and a superheated steam. In at least some instances, the thermal transfer fluid can include the following: a portion of the oxidative coupling of methane ("OCM") gas; a saturated steam; and a superheated steam.

In at least some instances, the quantity of methane may be adjusted by at least one of: adjusting a pressure of the methane source; adjusting a concentration of the methane within the methane source; and adjusting a mass flow rate of the methane source to a vessel containing the at least one catalyst. Adjusting the temperature of the oxidant may include adjusting, such that the temperature of the oxidant is at about 600° C. or less, at least one of: a fuel to a combustion heater used to transfer thermal energy to the oxidant and a thermal transfer fluid used to transfer thermal energy via at least one non-contact heat exchanger to the oxidant. The thermal transfer fluid may include at least one of: a portion of the oxidative coupling of methane ("OCM") gas; a saturated steam; and a superheated steam.

The methane source and oxidant may be mixed to provide a bulk gas mixture at a bulk gas temperature and the temperature of the bulk gas mixture may be limited to about 600° C. or less by adjusting at least one of: a fuel to a combustion heater used to transfer thermal energy to the methane source; a fuel to a combustion heater used to transfer thermal energy to the oxidant; a thermal transfer fluid used to transfer thermal energy via at least one non-contact heat exchanger to the methane source; and a thermal transfer fluid used to transfer thermal energy via at least one non-contact heat exchanger to the oxidant.

In at least some embodiments, adjusting a quantity of the oxygen comprises at least one of: adjusting a pressure of the oxidant; adjusting a concentration of the oxygen within the oxidant; and adjusting a mass flow rate of the oxidant to a vessel containing the at least one catalyst. The method may also include, responsive to detecting a temperature of 1100° C. or greater in the at least one catalyst, reducing the concentration of at least one of the methane and the oxygen in the bulk gas mixture. The method may further include, responsive to a rate of temperature increase of 25° C. per minute or greater in the at least one catalyst, reducing the concentration of at least one of the methane and the oxygen in the bulk gas mixture. The method may further include, responsive to detecting a stoichiometric ratio between the methane and the oxygen such that the methane is a limiting reagent, reducing the concentration of at least one of methane and oxygen in the bulk gas mixture.

In at least some instances, the thermal energy may be removed from the at least one catalyst via a coolant and adjusting a temperature profile across the at least one catalyst may include limiting a temperature increase across or through a catalyst bed containing the at least one catalyst to about 50° C. or less, thereby maintaining the at least one catalyst within a substantially isothermal operating environment. Removing thermal energy from the at least one catalyst via a coolant may include disposing the quantity of the at least one catalyst within an interior space defined by an open-ended, vertical tube and contacting the coolant with at least a portion of an exterior surface of the tube.

The methane source and the oxidant may be combined or otherwise mixed to provide a bulk gas mixture and at least one of: a methane concentration within the bulk gas mixture; an oxygen concentration within the bulk gas mixture; a methane source temperature; and an oxidant temperature may be adjusted to limit to a maximum temperature of about 1000° C. the at least one catalyst, while not removing thermal energy from the at least one catalyst, thereby maintaining the at least one catalyst within a substantially adiabatic operating environment.

In some instances, at least one catalyst may be disposed in the at least one vessel and an overall temperature increase through the quantity of the at least one catalyst may be adjusted using at least one of the methane concentration within the bulk gas mixture; the oxygen concentration within the bulk gas mixture; the methane source temperature; and, the oxidant temperature to provide a temperature increase through the at least one catalyst within the at least one vessel of about 50° C. or more.

A system for providing hydrocarbons having two or more carbon atoms ("$C_{2+}$ hydrocarbons") from methane may be summarized as including an inlet configured to receive a methane source and an inlet configured to receive an oxidant coupled to at least one vessel, the at least one vessel having a catalyst bed disposed therein, the catalyst bed including at least one oxidative coupling of methane ("OCM") catalyst; an inlet zone defined by the portion of the catalyst bed initially contacted by a bulk gas mixture formed by the methane source and the oxidant received by the at least one vessel; a control system operably coupled to the at least one vessel, the control system to: maintain a thermal profile across the catalyst bed during an OCM reaction, the thermal profile characterized by: a temperature of the inlet zone being less than about 600° C.; and a temperature at any point within the catalyst bed being less than about 950° C. and maintain a pressure at any point within the at least one vessel of less than 100 psig; and maintain an OCM reaction within the catalyst bed, the OCM reaction having a methane conversion of at least about 6% and a $C_{2+}$ hydrocarbon selectivity of at least 40%.

The catalyst bed within the at least one vessel may be operated under substantially isothermal conditions; and wherein the control system may be operably coupled to the at least one vessel to further maintain an OCM reaction within the catalyst bed, the OCM reaction having a methane conversion of at least about 20% and a $C_{2+}$ hydrocarbon selectivity of at least 50%.

The system may further include a hollow member defining an interior space, wherein the catalyst bed is disposed at least partially within the interior space; and wherein a thermal transfer medium is disposed on an exterior surface defined by the hollow member to absorb at least a portion of the thermal energy released by the OCM reaction within the catalyst bed. The system may further include at least one thermal transfer device thermally coupled to the at least one vessel, the at least one thermal transfer device to remove a portion of the thermal energy carried by the thermal transfer medium; wherein the control system is further operably coupled to the at least one thermal transfer device to further maintain the thermal transfer medium at a temperature of less than 595° C. The system may further include at least one thermal transfer device thermally coupled to the methane source; wherein the control system is operably coupled to the at least one methane source thermal transfer device to further maintain the methane source at a temperature of at least about 400° C. The system may further include at least one thermal transfer device thermally coupled to the oxidant; wherein the control system is operably coupled to the at least one oxidant thermal transfer device to further maintain the oxidant at a temperature of at least about 400° C.

The control system may be operably coupled to: at least one of a methane source pressure control device, a methane source temperature control device, and a methane source flow control device; and at least one of an oxidant pressure control device, an oxidant temperature control device, and an oxidant flow control device; to further maintain a radial thermal profile of at most about 200° C. within the catalyst bed. The control system may further maintain a temperature gradient through the catalyst bed of at most about 50° C. The control system may further maintain a ratio of the radial thermal profile to the temperature gradient of at least 3:1.

The catalyst bed may include at least one nanowire catalyst having at least one physical form. The at least one nanowire catalyst may include a nanowire catalyst having at least one chemical composition. The at least one nanowire catalyst may include at least one nanowire catalyst selected from the following: a metal oxide, a metal hydroxide, a perovskite, a metal oxyhydroxide, a metal oxycarbonate, a metal carbonate, a metal element from any of Groups 1 through 7, a lanthanide, and an actinide. The at least one nanowire catalyst may include a nanowire catalyst having at least one dopant. The at least one dopant may include at least one dopant selected from the following: a metal element, a semi-metal element, and a non-metal element.

The catalyst bed within the at least one vessel may be operated under substantially adiabatic conditions; and wherein the control system is operably coupled to the at least one vessel to further maintain an OCM reaction within the catalyst bed, the OCM reaction having a methane conversion of at least about 10% and a $C_{2+}$ hydrocarbon selectivity of at least 50%. The system may further include at least one methane source thermal transfer device thermally coupled to the methane source; wherein the control system is operably coupled to the at least one methane source thermal transfer device to further maintain the methane source at a temperature of at least about 400° C.

The system may further include at least one oxidant thermal transfer device thermally coupled to the oxidant; wherein the control system is operably coupled to the at least one oxidant thermal transfer device to further maintain the oxidant at a temperature of at least about 400° C. The control system may be operably coupled to: at least one of a methane source pressure control device, a methane source temperature control device, and a methane source flow control device; and at least one of an oxidant pressure control device, an oxidant temperature control device, and an oxidant flow control device; to further maintain a thermal gradient of less than about 350° C. through the catalyst bed.

The catalyst bed in the at least one vessel may include at least one nanowire catalyst having at least one physical form. The at least one nanowire catalyst may include a nanowire catalyst having at least one chemical composition. The at least one nanowire catalyst may include at least one nanowire catalyst selected from the following: a metal oxide, a metal hydroxide, a perovskite, a metal oxyhydroxide, a metal oxycarbonate, a metal carbonate, a metal element from any of Groups 1 through 7, a lanthanide, and an actinide. The at least one nanowire catalyst may include a nanowire catalyst having at least one dopant. The at least one dopant may include at least one dopant selected from the following: a metal element, a semi-metal element, and a non-metal element.

The at least one vessel may include a plurality of serially coupled vessels, each containing a catalyst bed; wherein the catalyst bed in each of the plurality of serially coupled vessels is operated under substantially adiabatic conditions; and wherein the control system is operably coupled to the plurality of serially coupled vessels to further maintain an OCM reaction having a methane conversion of at least about 10% and a $C_{2+}$ hydrocarbon selectivity of at least 50% within the catalyst bed within each of the plurality of serially coupled vessels. The system may further include at least one thermal transfer device disposed between each of the vessels forming the plurality of serially coupled vessels; and wherein the control system may be operably coupled to each of the thermal transfer devices to maintain to each subsequent vessel a bulk gas temperature of at most 400° C. The control system may be operably coupled to each of the thermal transfer devices to maintain a thermal gradient through the catalyst bed in each of the plurality of serially coupled vessels of less than about 350° C.

The catalyst bed in each of the plurality of serially coupled vessels may include at least one nanowire catalyst having at least one physical form. The at least one nanowire catalyst may include a nanowire catalyst having at least one chemical composition. The at least one nanowire catalyst may include at least one nanowire catalyst selected from the following: a metal oxide, a metal hydroxide, a perovskite, a metal oxyhydroxide, a metal oxycarbonate, a metal carbonate, a metal element from any of Groups 1 through 7, a lanthanide, and an actinide. The at least one nanowire catalyst may include a nanowire catalyst having at least one dopant. The at least one dopant may include at least one dopant selected from the following: a metal element, a semi-metal element, and a non-metal element.

Recycling at least a portion of the separated ethane to the at least one vessel may include recycling at least a portion of the separated ethane to the OCM gas.

BRIEF DESCRIPTION OF THE SEVERAL VIEWS OF THE DRAWINGS

In the drawings, the sizes and relative positions of elements in the drawings are not necessarily drawn to scale. For example, the various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been selected solely for ease of recognition in the drawings.

DETAILED DESCRIPTION OF THE INVENTION

Figure 1:
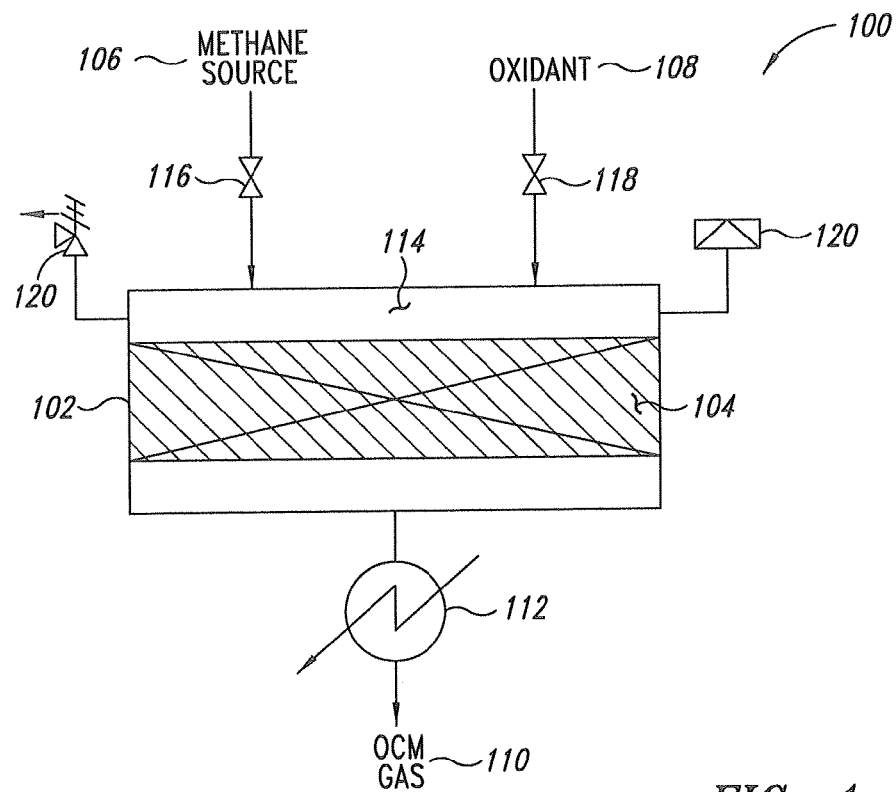
FIG. 1 shows a sectional view of an illustrative vessel for the adiabatic, exothermic, reaction of a methane source and an oxidant over at least one catalyst to provide an oxidative coupling of methane ("OCM") gas.

In the following description, certain specific details are set forth in order to provide a thorough understanding of various embodiments. However, one skilled in the art will understand that the invention may be practiced without these details. In other instances, well-known structures, standard vessel design details, details concerning the design and construction of American Society of Mechanical Engineers (ASME) pressure vessels, and the like have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The oxidative coupling of methane reactors and processes described herein provide significant improvements in $C_2$ and higher hydrocarbon yields, and in particular ethylene yields, while operating at a lower overall temperature, consuming lesser quantities of energy, and having a significantly lower GHG emission and carbon footprint than competitive olefin production facilities. The improvements in yield, operating conditions, energy consumption and GHG emissions are the result of the use of innovative catalysts within innovative processes using innovative methods as described in further detail herein.

As used herein the term "adiabatic" refers to a system experiencing minimal or ideally no interchange or exchange of thermal energy with the surrounding environment. As used herein "adiabatic" vessels and vessels said to be operating under "adiabatic" conditions refer to vessels having no provision specifically for the removal or addition of thermal energy to or from the system. Notwithstanding the foregoing, it will be appreciated that incidental thermal transfer between the vessel and its environment is contemplated within the context of the foregoing definition. Generally, where an adiabatic vessel is used to contain a reaction that releases thermal energy (i.e., an "exothermic" reaction), a positive temperature profile will be maintained between the reactants added to the vessel and the products removed from the vessel. In other words, the products removed from the vessel will generally be at a temperature above the temperature of the reactants introduced to the vessel since the thermal energy liberated by the reaction can only be substantially removed by the products of the reaction.

As used herein the term "isothermal" refers to a system experiencing an interchange or exchange of thermal energy with the surrounding environment providing a controlled level of increase in thermal energy within the system. As used herein, "isothermal" vessels and vessels, methods, and processes said to be operating under "isothermal" conditions refer to vessels, methods, and processes having specific provisions for the removal and dissipation of thermal energy from the vessel, method or process to the surrounding environment, in addition to any incidental heat transfer with the surrounding environment. Generally, where a vessel used to contain an exothermic reaction is said to be operated under "isothermal" conditions, a more neutral temperature profile as compared to a reactor operated under adiabatic conditions will be maintained across at least a portion of, if not the entire vessel. In other words, the temperature profile across at least a portion of the vessel, e.g., from one position in a catalytic bed to another or downstream position within the catalyst bed, may in some instances be substantially flat or increase at a controlled rate that is less than, and sometimes significantly less than, that which would occur under adiabatic conditions where thermal energy is not removed from the reaction vessel. In some cases, the thermal profile across the entire vessel may in some instances be flat, whereby the products removed from the vessel may be at a temperature substantially equal to the temperature of the reactants introduced to the vessel since the thermal energy liberated by the reaction is removed from the vessel and not by the products of the reaction.

As used herein the term "stoichiometric ratio" refers to the ratio of one compound to another compound. For example in the OCM reaction, theoretically two moles of methane are required to react with one mole of oxygen, yielding a balanced stoichiometric ratio of 2:1. The actual concentration of methane to oxygen may be greater than or less than 2:1. For example, where the stoichiometric ratio is 1.5 moles of methane to 1 mole of oxygen (1.5:1), methane is considered the limiting reagent since an insufficient quantity of methane is present to consume all of the oxygen. Similarly, where the stoichiometric ratio is 3 moles of methane to 1 mole of oxygen (3:1), oxygen can be considered the limiting reagent since an insufficient quantity of oxygen is present to consume all of the methane.

Figure 10A:
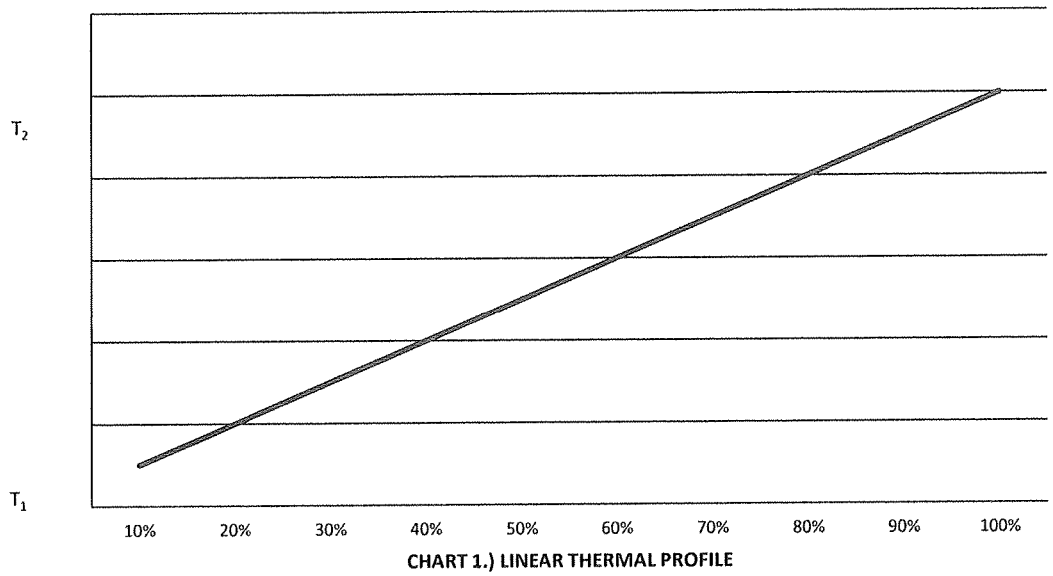
FIG. 10A shows a plot of an illustrative example linear thermal profile of temperature as a function of total percentage of distance traveled.
Figure 10B:
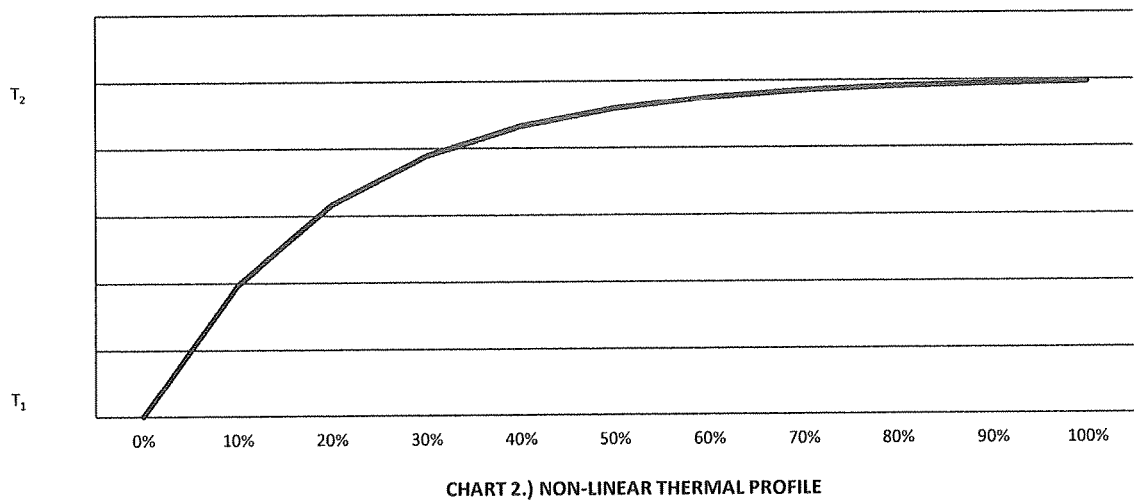
FIG. 10B shows a plot of an illustrative example non-linear thermal profile of temperature as a function of total percentage of distance traveled.

As used herein the term "temperature profile" or "thermal profile" refers to the temperature as a function of position through a reactor system or portion of a reactor system. An illustrative example linear thermal profile is shown in FIG. 10. An illustrative example non-linear thermal profile is shown in FIG. 11. In the illustrative thermal profiles shown in FIGS. 10 and 11, the X-axis represents the percentage of the overall distance through the catalyst bed. A temperature or thermal profile can be either a two-dimensional (e.g. linear function of distance through a catalyst bed) or three dimensions (e.g. linear function of distance through a catalyst bed, to provide a thermal profile as a function of distance through the catalyst bed, and radial function of distance from the center of a catalyst bed, to provide a thermal profile as a function of distance from the center of the catalyst bed).

In general, such temperature profiles may be visualized as a plot of temperature vs. position or location in a given system or component thereof. Such temperature profiles may refer to the continuum of temperatures across an entire reactor system, e.g., including one or more reactor vessels, heat exchangers, input and output streams, or it may refer to a temperature continuum across only a portion of a reactor system, e.g., a single reactor, a portion of a catalyst bed, e.g., a temperature gradient across one or more thicknesses of catalytic material. For example, where a bulk gas mixture having a first temperature $T_1$ and including methane and oxygen are present on a first side of a bed containing one or more catalysts and an OCM gas having a second temperature $T_2$ is present on the opposing or second side of the bed, the temperature increase across the catalyst bed is given by the simple subtraction $T_2$-$T_1$. However, the temperature profile across the bed is a function of the temperature increase per unit length (or volume) through the catalyst bed. The temperature profile through a catalyst bed may, but does not have to be, linear.

As used herein the term "gas hourly space velocity" or the acronym "GHSV" refers to the ratio of reactant gas flow rate (methane source+oxidant) in standard cubic feet per hour or standard cubic meters per hour, divided by the reactor volume (cubic feet or cubic meters). Where diluent gases are added, the GHSV includes the additional volume presented by the diluent gases. As used herein the term "velocity" refers to the superficial or linear velocity of a bulk gas flowing through a defined cross sectional area (e.g. SCFM or ACFM divided by the actual or equivalent cross sectional area in square feet). The resultant ratio has units of inverse hours and is used to relate reactant gas flow rate to reactor volume. The GHSV is one factor considered when scaling a known reactor design to accommodate a lesser or greater reactant flow.

As used herein the term "higher hydrocarbons" refers to any carbon compound containing at least two carbon atoms and includes alkane, alkene, alkynes, cycloalkanes, and aromatic hydrocarbons.

The reactors, systems and methods of the invention are particularly useful in carrying out exothermic catalytic reactions, and particularly such reactions as the catalyst mediated oxidative coupling of methane (OCM). In particular, OCM reactions have previously required extremely high reaction temperatures, e.g., in excess of 700° C. Coupled with the highly exothermic reactions, reactor systems for carrying out such reactions would be required to withstand temperatures well in excess of 700° C., and even when operated isothermally, e.g., using active external cooling systems, would require operating temperatures that are in excess of any conventionally available cooling systems. In addition to the practical limitations associated with simply designing reactor systems able to withstand the operating temperatures necessary to such reactions, it is additionally problematic that such previously described systems generally operate at temperatures at which the feedgas mixtures are highly flammable, and thus subject to explosion.

The present invention, however, provides systems and methods that utilize catalysts that operate at temperature profiles that are far better suited for available system design and manufacture, as well as potentially falling outside the zone of flammability for reaction feedgases, and in conjunction with appropriate control elements, allows control of reaction parameters, and of significant importance, temperature, while providing high yield and selectivity from such catalytic reactions.

In conjunction with such improved catalysts, the reactor systems and methods of the invention are able to initiate and carry out economically valuable exothermic catalytic reactions at lower temperatures and carry on those reactions within practical operating parameters. In particular, initiation and control of exothermic reactions at lower temperatures allows for further progression of the reaction either before maximum temperatures are exceeded, before thermal intervention is required, or with less energy expenditure in exercising such thermal intervention. For example, in particularly preferred aspects, the systems and methods of the invention are operated such that inlet temperatures for feed gases to the reactor system are maintained at less than 600° C., preferably, less than 550° C., more preferably less than 500° C., and in some cases, less than 450° C. The catalyst systems provide the benefit of being catalytic for the desired reaction at these reduced temperatures, and are likewise able to withstand the heat generation associated with the highly exothermic reactions, e.g., for OCM, without exceeding the desired operating parameters, as noted above.

For example, when operating in an adiabatic architecture, such systems include control systems that operate the system such that catalysis is initiated at these lower inlet temperatures, with a reaction heat generation that yields outlet temperatures of less than 950° C., less than 900° C., less than 850° C., less than 800° C., and in some cases, less than 750° C. or even 700° C., while still providing economical conversion and selectivity. Accordingly, such systems may be operated such that the temperature gradient across a reactor system, e.g., inlet temperature to outlet temperature is preferably around 250° C., but optionally ranging from approximately 150° C. to about 500° C.

When operated in an isothermal architecture, e.g., using external heat control systems, as described in greater detail below, the systems of the invention utilize control elements that operate at inlet temperatures that are less than 600° C., or less than the maximum temperature of conventional cooling systems, e.g., 593° C. for molten salt cooling systems, and preferably at the inlet temperatures described above. In some instances, the inlet temperatures in the isothermal system may be less than the reaction temperature and one or more thermal control systems may be used to provide the thermal energy necessary to increase the temperature of the bulk gas mixture to the desired reaction temperature, e.g., 550° C. Because they are being operated nearly isothermally, these systems are preferably controlled such that the outlet temperature of a given reactor system is substantially equivalent to the inlet temperature, e.g., within about 50° C., within about 25° C., within about 10° C., within about 5° C., of the inlet temperature, and in any event not exceeding the maximum operable temperature of the cooling system.

Oxidative Coupling of Methane Process Control

The OCM reaction is an exothermic, catalytic reaction between methane and oxygen to provide an OCM gas containing longer chain hydrocarbons such as ethane, ethylene and higher hydrocarbons such as propane, propylene, butane, butene, and the like. The OCM gas will also contain quantities of unreacted oxygen and methane as well as inert materials such as nitrogen introduced with the methane or oxygen. The exothermic nature of the OCM reaction releases a significant quantity of heat. In an adiabatic operating regime, this heat is not removed during the reaction and is instead carried away from the reaction by the OCM gas, unreacted reagents, and by-products. In an isothermal operating regime, a substantial quantity of this heat is removed from the reaction, typically using a heat transfer media. Thus, a reaction carried out under adiabatic conditions will experience a greater temperature increase between the input streams and the output streams than a comparable reaction carried out under isothermal conditions.

In addition to the methane concentration and oxygen concentration within the reactor, the conversion of methane in the OCM process may also be affected by adjusting the thermal conditions within and around the catalyst. Catalyst thermal conditions include the overall temperature increase through the catalyst (i.e., the temperature of the OCM gas exiting the catalyst bed minus the temperature of the bulk gas mixture introduced to the catalyst), the temperature profile within the catalyst (i.e., point temperature as a function of distance traveled through the catalyst), the maximum temperature within the catalyst or the instantaneous or average rate of temperature increase through the catalyst bed may be adjusted alone or in tandem to affect the conversion of methane to longer chain hydrocarbons in the OCM process. The yield of the OCM process, typically, although not exclusively measured as the quantity of methane converted to one or more desired products, may also be similarly affected by adjusting the catalyst thermal conditions either alone or in tandem.

The conversion of methane in the OCM process can also be affected or influenced by the overall composition of the bulk gas mixture introduced to the catalyst, e.g., methane concentration and/or oxygen concentration. In various instances, one or more inert gases such as nitrogen may be present in the bulk gas mixture. The presence of inert gases provides a stable thermal "heat sink" within the bulk gas mixture that is capable of absorbing thermal energy and consequently limits the temperature increase experienced by the oxygen, methane and OCM gas present in the catalyst bed. The ratio of methane to oxygen (e.g., the stoichiometric ratio of methane to oxygen) within the bulk gas mixture can affect the overall conversion of methane in the OCM reaction.

In some instances, oxygen can be controlled or otherwise maintained as the limiting reactant such that at least a portion of the methane present in the methane source remains unconsumed by the OCM reaction and the exiting OCM gas, while depleted in oxygen, contains a quantity of residual unreacted methane when removed from OCM reaction. OCM gas containing methane may be fed to a subsequent OCM reaction step, generally after an additional oxidant is introduced to support conversion of the unreacted methane present in the OCM gas.

The OCM reaction can occur in a single vessel, in a plurality of serially coupled vessels, in a plurality of parallel vessels, or combinations thereof. One or more catalyst beds may be located in each of the vessels, again arranged in series, parallel or any combination thereof. Where multiple catalyst beds are arranged in series, either in the same or different vessels, additional methane, oxygen, $C_{2+}$ hydrocarbons, inert gases, or any combination thereof may be added, in some instances at a significantly cooler or warmer temperature than the OCM gas exiting the preceding catalyst bed, to adjust the composition and temperature of the bulk gas mixture prior to its introduction to the subsequent catalyst bed. In some instances, each catalyst bed may include the same or a differing number of layers, with each layer including a catalytic material, an inert material, or combinations thereof.

Where the OCM process is carried out in a single vessel operating under adiabatic conditions, the ability to independently control bulk gas composition, bulk gas temperature, catalyst bed structure, catalyst bed composition, and catalyst thermal profile provides a variety of measurable process variables and control variables that can be adjusted to affect the performance, conversion, selectivity, and yield of the OCM process. Where the OCM process is carried out in a plurality of serial or tandem vessels, the ability to independently control across each vessel or collectively control across all vessels the control bulk gas composition, bulk gas temperature, catalyst bed structure, catalyst bed composition, and catalyst thermal profile provides the ability to operate the OCM process to meet varying production demands.

Bulk Gas Pressure, Temperature, Flow, and Composition

The composition of the bulk gas mixture provides another variable that may be adjusted to control the OCM process. The bulk gas is formed by combining at least the methane source and an oxidant to provide the methane and oxygen needed for the OCM reaction. In instances where more than one catalyst bed is present in each of the one or more vessels, the bulk gas temperature, pressure or composition may be controlled or otherwise adjusted prior to the introduction of the bulk gas mixture to some or all of the beds.

One or more secondary reactants including other gases such as longer chain, alkane, alkene, and alkyne hydrocarbons may also be introduced to the bulk gas mixture. The composition of the bulk gas mixture is a direct function of the composition of the constituent methane source and oxidant used to provide the bulk gas mixture. In at least some instances, the methane source or the oxidant may contain one or more inert gases such as nitrogen. Thus, by controlling the quantity of methane or inert gas present in the methane source and controlling the quantity of oxygen or inert gas present in the oxidant, a bulk gas mixture having virtually any composition and methane to oxygen stoichiometric ratio can be provided.

In determining the composition of the methane source, one or more analyzers may be used to provide one or more signals indicative of the composition, including methane and inert gas content, of the methane source. One or more analyzers may be used to provide one or more signals indicative of the composition, including oxygen and inert gas content, of the oxidant. In at least some instances, one or more analyzers may be used to provide one or more process signals indicative of the flow or composition, including oxygen, methane, secondary reactant, and inert gas content of the bulk gas mixture prior to introduction to the catalyst bed in at least some of the plurality of vessels. In a like or similar manner any number of analyzers may be used on one or more constituent gases used to provide the bulk gas mixture. For example, where one or more $C_{2+}$ hydrocarbons are used to form a portion of the bulk gas mixture, one or more analyzers may be used to determine the composition of the $C_{2+}$ hydrocarbon gas, or to determine the concentration of one or more targeted gas species, hydrocarbon or otherwise, in the $C_{2+}$ hydrocarbon gas.

The temperature of the bulk gas mixture provides another variable that may be used for control of the OCM process. The temperature of the bulk gas mixture can be adjusted or controlled by increasing or decreasing the amount of thermal energy imparted to the methane source, the oxidant, or the bulk gas mixture, for example through the use of one or more thermal transfer devices using a heat transfer fluid at a desired temperature (e.g., using air or cooling water to reduce the temperature or a high temperature fluid or process fluid to increase the temperature), one or more combustion gas thermal transfer devices using a combustion fuel to provide thermal energy, or combinations thereof. Thus, by controlling the quantity of thermal energy added to or removed from the methane source or the oxidant a bulk gas mixture having virtually any temperature may be introduced to a catalyst bed.

In determining the temperature of the methane source, one or more thermocouples, resistive thermal devices (RTDs) or similar temperature measuring devices may be used to provide one or more signals indicative of the temperature of the methane source. One or more thermocouples, resistive thermal devices (RTDs) or similar temperature measuring devices may be used to provide one or more signals indicative of the temperature of the oxidant. In at least some instances, one or more thermocouples, resistive thermal devices (RTDs) or similar temperature measuring devices may be used to provide one or more signals indicative of the temperature of the bulk gas mixture prior to introduction of the bulk gas mixture to the catalyst bed in at least some of the plurality of vessels.

The pressure of the bulk gas mixture provides another variable that may be used for control of the OCM process. The pressure of the bulk gas mixture can be adjusted or controlled by increasing or decreasing the amount of compressive energy imparted to the methane source, the oxidant, or the bulk gas mixture, for example through the use of one or more gas compressors or by controlling the back pressure through the one or more vessels 102. Thus, by controlling the quantity of compressive energy imparted to the methane source or the back pressure through the one or more vessels 102, the oxidant, or the bulk gas mixture itself, a bulk gas mixture at virtually any pressure may be introduced to a catalyst bed.

In determining the pressure of the methane source, one or more pressure transducers or similar pressure measuring devices may be used to provide one or more signals indicative of the pressure of the methane source. One or more pressure transducers or similar pressure measuring devices may be used to provide one or more signals indicative of the pressure of the oxidant. In at least some instances, one or more pressure transducers or similar pressure measuring devices may be used to provide one or more signals indicative of the pressure of the bulk gas mixture prior to introduction of the bulk gas mixture to the catalyst bed in at least some of the plurality of vessels.

The flowrate of the bulk gas mixture to each of the one or more catalyst beds in each of the one or more vessels provides another variable that may be used for control of the OCM process. The flowrate of the bulk gas mixture can be adjusted or controlled by increasing or decreasing the methane source flowrate, the oxidant flowrate, or combinations thereof, for example through the use of one or more flow control valves. In addition, one or more block valves, arranged for example in a double block and bleed arrangement, may be used to provide a safety system for some or all of the one or more vessels. Thus, by controlling the flow of the methane source, the oxidant, or the bulk gas mixture itself, a bulk gas mixture at virtually any flowrate may be introduced to the subsequent catalyst bed.

To determine the flowrate of the methane source, one or more mass or volumetric flow meters or similar flow measuring devices may be used to provide one or more signals indicative of the flowrate of the methane source. One or more mass or volumetric flow meters or similar flow measuring devices may be used to provide one or more signals indicative of the flowrate of the oxidant. In at least some instances, one or more mass or volumetric flow meters or similar flow measuring devices may be used to provide one or more signals indicative of the flowrate of the bulk gas mixture prior to introduction of the bulk gas mixture to the catalyst bed in at least some of the plurality of vessels.

Catalyst Thermal Conditions

Each of the one or more vessels may contain one or more catalyst beds and each of the one or more catalyst beds may include one or more layers of catalyst. In some instances, each of the one or more vessels may contain a single catalyst bed containing a catalyst having a similar chemical composition and physical structure. In other instances, each of the one or more vessels may contain the same or a differing number of catalyst beds and each of the catalyst beds may contain the same or a differing number of layers. Thus, by controlling the catalyst load, one or more preferred OCM gas properties may be adjusted in an individual process or even an individual vessel within a larger process.

Where the catalyst operates under substantially adiabatic conditions, the thermal energy released by the exothermic OCM reaction is removed primarily with the OCM gas and to a lesser extent in the form of parasitic convective losses from less than ideally insulated process equipment, vessels, and piping. Due to the lack of heat transfer within the catalyst bed itself, the temperature gradient or increase across a catalyst bed operated under substantially adiabatic conditions will be greater than the temperature gradient or increase across a comparable bed operated under substantially isothermal conditions.

In at least some instances, one or more temperature sensors may be located at the inlet to and outlet from all or a portion of the one or more catalyst beds, at intervals within the catalyst bed, or combinations thereof. The temperature sensors can provide one or more signals indicative of the temperature prior to the catalyst bed, within the catalyst bed, exiting the catalyst bed, the temperature gradient or increase across the catalyst bed or combinations thereof. At least a portion of the catalyst temperature data may be monitored over a measured time period and the resultant temperature change with respect to time (dT/dt) may be determined. At least a portion of the temperature data may be used as a process variable input to one or more temperature, pressure, flow, or composition controllers generating at least one control output directed to one or more final control elements acting on the methane source, the oxidant, the bulk gas mixture, or combinations thereof.

The catalyst bed inlet temperature, catalyst bed outlet temperature, or the temperature gradient or increase across a catalyst bed operated under substantially adiabatic conditions may be adjusted by controlling the temperature, pressure, composition or flowrate of any or all of the methane source, the oxidant, or the bulk gas mixture. As used herein, the term "catalyst bed inlet temperature" and "inlet temperatures" or similar terms referencing a catalyst bed refer to the temperature at the point in the catalyst bed where catalytic chemical reactivity commences. Similarly, the maximum temperature within a catalyst bed operated under substantially adiabatic conditions may be adjusted by controlling the temperature, pressure, composition or flowrate of any or all of the methane source, the oxidant, or the bulk gas mixture.

In at least some instances, temperatures may be determined at periodic intervals within the catalyst bed to provide a thermal profile of a catalyst bed operating under substantially isothermal conditions. While, in an ideal case, the thermal profile for a catalyst bed operated under isothermal conditions would be a flat line (i.e., constant temperature through the bed), in practice even under isothermal conditions a thermal profile that varies with location in the catalyst bed will result. For example, where the OCM reaction occurs at the greatest rate, the thermal profile will generally show a temperature increase or peak due to the inability of the thermal transfer fluid to absorb all of the thermal energy released within the region of the catalyst bed where the OCM reaction occurs. Similar to the adiabatically operated catalyst bed, the thermal profile through an isothermally operated catalyst bed provides insight into the location or locations within the catalyst bed where the OCM reaction may be initiated or occurring at the greatest rate based on the measured output of thermal energy within the bed. In at least some instances, the composition of the OCM gas exiting a catalyst bed may be altered, affected or even controlled based upon the thermal profile across the catalyst bed. Additionally, determination of the thermal profile across a catalyst bed permits monitoring and controlling the catalyst bed conditions on an continuous basis by providing one or more reliably measured process variables (temperature within the catalyst bed) that may be used as an input to one or more temperature, pressure, flow or composition controllers acting on the methane source, the oxidant, the bulk gas mixture, or combinations thereof. Where one or more vessels are serially coupled, separate thermal profiles may be developed for each of the vessels and the temperature, pressure, flow or composition controllers acting on the methane source, the oxidant, the bulk gas mixture, or combinations thereof introduced to each of the plurality of vessels may be individually (i.e., the thermal profile across a single vessel) or collectively (i.e., the thermal profile across all of the one or more vessels) controlled.

Where the catalyst operates under substantially isothermal conditions, the thermal energy released by the exothermic OCM reaction is removed primarily by a heat transfer fluid to limit the temperature buildup within the catalyst bed. However, even with the removal of a portion of the thermal energy via the thermal transfer fluid, a portion of the thermal energy released by the OCM reaction will be removed with the OCM gas. Due to the removal of at least a portion of the thermal energy via the thermal transfer fluid, the temperature gradient or increase across a catalyst bed operated under substantially isothermal conditions will be less than the temperature gradient or increase across a comparable bed operated under substantially adiabatic conditions.

In at least some instances, one or more temperature sensors may be located at the inlet to and outlet from all or a portion of the one or more catalyst beds, at intervals within the catalyst bed, or combinations thereof. The temperature sensors can provide one or more signals indicative of the temperature prior to the catalyst bed, within the catalyst bed, exiting the catalyst bed, the temperature gradient or increase across the catalyst bed or combinations thereof. At least a portion of the catalyst temperature data may be monitored over a measured time period and the resultant temperature change with respect to time (dT/dt) may be determined. At least a portion of the temperature data may be used as a process variable input to one or more temperature, pressure, flow, or composition controllers generating at least one control output directed to one or more final control elements acting on the methane source, the oxidant, the bulk gas mixture, the thermal transfer fluid removing thermal energy from the catalyst bed, or combinations thereof.

The catalyst bed inlet temperature, catalyst bed outlet temperature, or the temperature gradient or increase across a catalyst bed operated under substantially isothermal conditions may be adjusted by controlling the temperature, pressure, composition or flowrate of any or all of the methane source, the oxidant, or the bulk gas mixture. The catalyst bed inlet temperature, catalyst bed outlet temperature, or the temperature gradient or increase across a catalyst bed operated under substantially isothermal conditions may also be adjusted by controlling the flowrate or temperature of the thermal transfer fluid used to remove thermal energy from the catalyst bed. The maximum temperature within a catalyst bed operated under substantially isothermal conditions may be adjusted by controlling the temperature, pressure, composition or flowrate of any or all of the methane source, the oxidant, or the bulk gas mixture. The maximum temperature within a catalyst bed operated under substantially isothermal conditions may be adjusted by controlling the flowrate or temperature of the thermal transfer fluid used to remove thermal energy from the catalyst bed.

In at least some instances, temperatures may be determined at periodic intervals within the catalyst bed to provide a thermal profile of the catalyst bed, for example temperatures measured at fixed or variable intervals through the catalyst bed. The thermal profile through a catalyst bed provides insight into the location or locations within the catalyst bed where the OCM reaction may be initiated or occurring at the greatest rate based on the measured output of thermal energy within the bed. In at least some instances, the composition of the OCM gas exiting a catalyst bed may be altered, affected or even controlled based upon the thermal profile across the catalyst bed. Additionally, determination of the thermal profile across a catalyst bed permits monitoring and controlling the catalyst bed on an continuous basis by providing one or more reliably measured process variables (temperature within the catalyst bed) that may be used as an input to one or more temperature, pressure, flow or composition controllers acting on the methane source, the oxidant, the bulk gas mixture, or combinations thereof. Where one or more vessels are serially coupled, separate thermal profiles may be developed for each of the vessels and the temperature, pressure, flow or composition controllers acting on the methane source, the oxidant, the bulk gas mixture, or combinations thereof introduced to each of the plurality of vessels may be individually (i.e., the thermal profile across a single vessel) or collectively (i.e., the thermal profile across all of the one or more vessels) controlled.

OCM Gas Temperature, Pressure, Flow, and Composition

The temperature, pressure, flow, or composition of the OCM gas exiting from each of the one or more catalyst beds in each of the one or more vessels may be monitored individually at different locations or as a group at a single location in or proximate each of the one or more vessels. Using temperature sensors/transmitters, pressure sensors/transmitters, flow sensors/transmitters, or composition analyzers, one or more signals may be introduced to one or more controllers used to modulate or control the temperature, pressure, flow, or composition of the methane source; to modulate or control the temperature, pressure, flow, or composition of the oxidant; to modulate or control the catalyst thermal conditions, or combinations thereof to provide an OCM gas having one or more targeted properties.

In at least some instances, one or more targeted OCM gas properties may include an OCM gas having a concentration of one or more longer chain hydrocarbons, for example ethane, ethylene, propane, propylene, butane, butene, and the like that falls within a range. In at least some instances, one or more targeted OCM gas properties may include an OCM gas having a methane concentration that falls within a range. In at least some instances, one or more targeted OCM gas properties may include an OCM gas having an oxygen concentration that falls within a range.

In at least some instances, the composition, pressure, flow, or temperature of the OCM gas may be used as a process variable input to one or more controllers providing one or more control outputs to one or more final control elements, for example, one or more flow control valves, used to control the composition of the methane source, the oxidant, the bulk gas mixture, or combinations thereof in some or all of the plurality of vessels. In at least some instances, the composition, pressure, or temperature of the OCM gas may be used as a process variable input to one or more controllers providing one or more control outputs to one or more final control elements, for example, one or more temperature control valves, used to directly or indirectly control the temperature of the methane source, the oxidant, the bulk gas mixture, or combinations thereof in some or all of the plurality of vessels. In at least some instances, the composition, pressure, or temperature of the OCM gas may be used as a process variable input to one or more controllers providing one or more control outputs to one or more final control elements, for example, one or more pressure control valves, used to directly or indirectly control the pressure of the methane source, the oxidant, the bulk gas mixture, or combinations thereof in some or all of the plurality of vessels.

FIG. 1 shows schematically a system 100 for the production of one or more alkene hydrocarbons via oxidative coupling of methane ("OCM") in the presence of at least one catalyst. The system 100 includes at least one vessel 102 containing one or more catalysts disposed in at least one catalyst bed 104. A methane source 106 and an oxidant 108 are either pre-mixed or combined and introduced to the at least one vessel 102 or introduced separately to the one or more vessels 102 and an oxidative coupling of methane ("OCM") gas 110 is removed from the one or more vessels 102. At least a portion of the thermal energy within the OCM gas 110 is removed using one or more thermal transfer devices 112. Within the at least one vessel 102, methane in the methane source 106 and oxygen in the oxidant 108 exothermically react as they pass through the one or more catalysts disposed in the at least one catalyst bed 104. In at least some embodiments, the extent of the at least one catalyst bed 104 can include substantially the entire cross sectional area of the at least one vessel 102, thereby minimizing or eliminating the possibility of gas bypass around the at least one catalyst bed 104. The lack of thermal energy transfer within the at least one vessel 102 depicted in FIG. 1 permits the operation of the one or more catalysts forming the at least one catalyst bed 104 under substantially adiabatic conditions.

Methane Source

The OCM reaction is a catalytic gas phase reaction where methane is reacted in the presence of oxygen and one or more catalysts to exothermically produce one or more hydrocarbons containing two or more carbon atoms (collectively referred to herein as "$C_{2+}$ compounds") and water. Methane is supplied via the methane source 106. The introduction of the methane source 106 to the one or more vessels 102 can be manually or automatically controlled using one or more final control elements 116. The methane source 106 can be any gas or mixture of gases containing at least about 5 mol % methane; at least about 10 mol % methane; at least about 20 mol % methane; at least about 30 mol % methane; at least about 40 mol % methane; at least about 50 mol % methane; at least about 60 mol % methane; at least about 70 mol % methane; at least about 80 mol % methane; at least about 90 mol % methane; or at least about 95 mol % methane.

The methane source 106 can include a commercial natural gas source, for example a natural gas feed from one or more municipal or industrial gas suppliers. In some embodiments, at least a portion of the methane source 106 can include biogas—methane derived from one or more processes involving the decay of organic substances. In some embodiments, at least a portion of the methane source 106 can be provided as a byproduct from another co-located process facility. In some embodiments, at least a portion of the methane source 106 can be provided by a liquefied natural gas ("LNG") or compressed natural gas ("CNG") terminal or storage facility. In one preferred embodiment, at least a portion of the methane source 106 can include an industrial methane source, for example methane drawn from a pipeline which typically does not contain an odorant such as the mercaptan-based odorants commonly found in commercially sourced natural gas. In another preferred embodiment, at least a portion of the methane source 106 can include wellhead natural gas drawn directly from a naturally occurring or manmade subterranean reservoir or from storage facilities fluidly coupled to the naturally occurring reservoir.

A potentially attractive methane source 106 can be found in wellhead natural gas located in remote or difficult to access areas (i.e., "stranded" natural gas) such as deep-sea platforms, or wellheads in remote geographic regions such as the Antarctic or in the tundra regions of Asia and North America. Although methane is quite valuable, the inherent difficulties in transporting a relatively light hydrocarbon gas having a very low boiling point often precludes the use of surface transport for large quantities of methane via ship or truck, for example in the form of liquefied natural gas and relegates the transmission of large quantities of methane to pipelines. Such pipelines require significant capital investment in infrastructure such as recompression stations, and frequently incur high operating expenses such as electric or steam to power the recompression stations, to provide economic transport for large quantities of methane. Conversion of methane to one or more alkene hydrocarbons using OCM and subsequent oligomerization or polymerization of the alkene hydrocarbons to products that are in local demand or that are more amenable to low cost, long distance, transport, for example chemical intermediates or liquid fuels such as gasoline and diesel, provide economically attractive alternatives to the transport of methane extracted from stranded sources as either LNG or CNG.

Wellhead methane gas may contain numerous impurities upon extraction. Typical impurities can include, but are not limited to, ethane, propane, butanes, pentanes, and higher molecular weight hydrocarbons, hydrogen sulfide, carbon dioxide, water vapor, and inert gases such as helium and nitrogen. In some instances, all or a portion of the one or more inert gases present may be as a consequence of their injection into the subterranean formation to stimulate the extraction of natural gas from the formation.

Typically, higher molecular weight hydrocarbons (e.g., $C_3$ and higher hydrocarbons) present in the natural gas are partially or completely removed from the natural gas via condensation to form a natural gas liquid ("NGL"). Of the remaining impurities present in the natural gas, hydrogen sulfide and other sulfur containing compounds present in the natural gas are removed upstream of the at least one vessel 102 to reduce, or ideally eliminate, the formation of corrosive sulfur oxides in the OCM process. In at least some embodiments, the wellhead methane can pass through one or more separation or purification processes to remove all or a portion of the hydrogen sulfide and other sulfur containing compounds present in the methane source 106. After purification or separation, the sulfur concentration in the methane source 106 can be about 50 ppm or less; about 40 ppm or less; about 30 ppm or less; about 20 ppm or less; about 10 ppm or less; about 5 ppm or less; or about 1 ppm or less. In at least some embodiments, the wellhead methane can pass through one or more separation or purification processes to remove all or a portion of the carbon dioxide present in the methane source 106. After purification or separation, the carbon dioxide concentration in the methane source 106 can be about 50 ppm or less; about 40 ppm or less; about 30 ppm or less; about 20 ppm or less; about 10 ppm or less; about 5 ppm or less; or about 1 ppm or less.

In some embodiments, a wellhead supplying at least a portion of the methane source 106 may use nitrogen, carbon dioxide, other inert gas(es), or inert gas mixtures to stimulate the production of subterranean natural gas, particularly as the supply of natural gas contained in the reservoir becomes depleted. In some instances, all or a portion of the nitrogen present in the methane source 106 can be removed, for example using one or more distillation or cryogenic distillation processes such as those typically found in a nitrogen rejection unit ("NRU"). At least a portion of the nitrogen recovered from the methane source 106 can be recycled to the wellhead for use in stimulating additional production from one or more natural gas or crude oil wells. However, the separation of nitrogen from the methane source 106 may not be 100% effective and some quantity of residual nitrogen may remain in the methane source 106. After separation of the nitrogen from the methane source 106, the nitrogen concentration in the methane source 106 can be less than about 50 mol %; less than about 40 mol %; less than about 30 mol %; less than about 20 mol %; less than about 10 mol %; less than about 5 mol %; less than about 2 mol %; less than about 1 mol %; or less than about 0.5 mol %.

In at least some instances, the methane source 106 can be at a pressure greater than atmospheric pressure upon mixing with the oxidant 108 or introduction to the one or more vessels 102. In at least some instances, the increased pressure may be attributable at least in part to the extraction pressure of the methane source 106 at the wellhead. In other instances, one or more compressors, for example one or more centrifugal, reciprocating, or screw-type compressors, may be used to increase the pressure of the methane source 106. The methane source 106 can be at a pressure of less than about 150 psig; less than about 100 psig; less than about 75 psig; less than about 60 psig; less than about 50 psig; less than about 40 psig; less than about 30 psig; less than about 20 psig; less than about 15 psig; less than about 10 psig; less than about 5 psig; or less than about 1 psig.

In at least some instances, the rate of the OCM reaction occurring in the one or more vessels 102 can be influenced, adjusted, or controlled based, at least in part, on the temperature of the methane source 106. The temperature of the methane source 106 can be adjusted using one or more thermal transfer devices capable of transferring thermal energy to the methane source 106. Such thermal transfer devices can include, but are not limited to, non-contact combustion type heaters and non-contact thermal fluid heat exchangers. The methane source 106 can be at a temperature of less than about 600° C.; less than about 575° C.; less than about 550° C.; less than about 525° C.; less than about 500° C.; less than about 450° C.; or less than about 400° C.

In at least some instances, the methane source 106 can contain one or more $C_{2+}$ alkane hydrocarbons, for example ethane, propane, butane, pentane, hexane, and the like. The alkane $C_{2+}$ hydrocarbons can be naturally formed with the methane source 106 or back-added or recycled to the methane source 106 from another source after extraction, including recycling a portion of a product gas from one or more vessels 102. The alkane $C_{2+}$ concentration within the methane source 106 can be less than about 20 mol %; less than about 15 mol %; less than about 10 mol %; less than about 8 mol %; less than about 5 mol %; less than about 2 mol %; less than about 1 mol %; or less than about 0.5 mol %.

Oxidant

Oxygen is introduced to the one or more vessels 102 via the oxidant 108. In some instances, at least a portion of the oxidant 108 may be supplied in the form of purified oxygen, for example as supplied by an air separation unit ("ASU"). As used herein, the term "purified oxygen" can refer to a gas having an oxygen concentration greater than 21 mol %. The use of purified oxygen to provide at least a portion of the oxidant 108 may be possible, for example, where an ASU is used to provide nitrogen used to extract crude oil or natural gas at the wellhead. In other instances, at least a portion of the oxidant 108 may be supplied in the form of air or compressed air, containing about 21 mol % oxygen and about 78 mol % nitrogen. In some instances, the oxidant 108 may be a mixture of air and purified oxygen having an oxygen concentration between that of air and purified oxygen. Thus, the oxidant 108 can be any gas or mixture of gases containing at least about 5 mol % oxygen; at least about 10 mol % oxygen; at least about 20 mol % oxygen; at least about 30 mol % oxygen; at least about 40 mol % oxygen; at least about 50 mol % oxygen; at least about 60 mol % oxygen; at least about 70 mol % oxygen; at least about 80 mol % oxygen; at least about 90 mol % oxygen; or at least about 95 mol % oxygen.

The oxidant 108 may also contain nitrogen and small quantities of inert gases such as argon, particularly where air is used to provide some or all of the oxidant 108. The nitrogen concentration in the oxidant 108 is dependent upon the one or more sources used to provide the oxygen, however the nitrogen concentration in the oxidant 108 can be no more than about 5 mol %; no more than about 10 mol %; no more than about 20 mol %; no more than about 30 mol %; no more than about 40 mol %; no more than about 50 mol %; no more than about 60 mol %; no more than about 70 mol %; or no more than about 80 mol %.

The introduction of the oxidant 108 to the one or more vessels 102 can be manually or automatically controlled using one or more final control elements 118. Controlling the oxygen concentration within the one or more vessels 102 can influence, affect, or control the OCM reaction occurring within the one or more catalysts disposed in the catalyst bed 104. As such, the ability to adjust the oxygen concentration within the oxidant 108 may be accomplished in one embodiment by supplying a portion of the oxidant 108 in the form of compressed air having an oxygen concentration of about 21 mol %, and adding a second portion of the oxidant 108 in the form of purified oxygen in a controlled manner to achieve any desired or target oxygen concentration within oxidant 108.

The oxidant 108 can be at a pressure greater than atmospheric pressure upon introduction to the one or more vessels 102. In at least some instances, the increased pressure may be attributable at least in part to the pressure of the oxidant 108 source, for example an oxidant 108 including purified oxygen at a high pressure may be available from an ASU. In other instances, one or more compressors may be used to increase the pressure of the oxidant 108 upstream of the one or more vessels 102. The oxidant 108 can be at a pressure of less than about 150 psig; less than about 100 psig; less than about 75 psig; less than about 60 psig; less than about 50 psig; less than about 40 psig; less than about 30 psig; less than about 20 psig; less than about 15 psig; less than about 10 psig; less than about 5 psig; or less than about 1 psig.

In at least some instances, the rate of the OCM reaction within the one or more vessels 102 can be influenced, adjusted, or controlled based at least in part on the temperature of the oxidant 108. The temperature of the oxidant 108 can be adjusted using one or more thermal transfer devices capable of transferring thermal energy to the oxidant 108. Such thermal transfer devices can include, but are not limited to, non-contact combustion type heaters and non-contact thermal fluid heat exchangers. The oxidant 108 can be at a temperature of less than about 600° C.; less than about 575° C.; less than about 550° C.; less than about 525° C.; less than about 500° C.; less than about 450° C.; or less than about 400° C.

Bulk Gas Mixture

At least a portion of the methane source 106 and at least a portion of the oxidant 108 combine before entering the at least one vessel 102 or within the at least one vessel 102 to provide a bulk gas mixture 114 containing at least methane and oxygen. In at least some embodiments, nitrogen may also be present in the bulk gas mixture 114, introduced with the methane source, the oxidant or both the methane source and the oxidant. In some instances, one or more $C_{2+}$ alkane, alkene, alkyne, or aromatic hydrocarbons may be added to the bulk gas mixture either prior its introduction to the at least one vessel 102 or within the at least one vessel 102. In at least some instances, all or a portion of the one or more $C_{2+}$ alkane, alkene, alkyne, or aromatic hydrocarbons added to the bulk gas mixture may include one or more $C_{2+}$ hydrocarbons separated from the OCM gas 110.

Nitrogen passes through the OCM catalyst as an inert and may beneficially provide a "heat sink" during the OCM reaction by absorbing at least a portion of the heat liberated by the exothermic OCM reaction. To the extent that nitrogen can be used as a "heat sink" which affects the temperature or thermal profile through one or more catalysts within the one or more vessels, the nitrogen concentration within the bulk gas mixture 114 may be used to adjust, affect, or control the OCM reaction. In at least some embodiments, a minimum nitrogen concentration may therefore be maintained within the bulk gas mixture 114 formed by the methane source 106 and the oxidant 108 within the at least one vessel 102. The nitrogen concentration within the bulk gas mixture 114 can be at most about 5 mol %; at most about 10 mol %; at most about 15 mol %; at most about 20 mol %; at most about 25 mol %; at most about 30 mol %; at most about 40 mol %; at most about 50 mol %; at most about 60 mol %; at most about 70 mol %; at most about 75 mol %. Nitrogen exiting the one or more vessels 102 in the OCM gas 110 may also serve as a refrigerant useful in post-process separation of the OCM gas into one or more product or intermediate streams. For example, in some embodiments a portion of the OCM gas 110 containing nitrogen can be compressed and expanded to provide refrigeration useful, for example, in one or more downstream cryogenic separation processes. See, e.g., Provisional U.S. Patent Application No. 61/586,711, filed Jan. 13, 2012, the full disclosure of which is hereby incorporated herein by reference in its entirety for all purposes to the extent that subject matter and definitions contained in the incorporated application do not contradict the subject matter and definitions contained in this application.

The bulk gas mixture 114 in the one or more vessels 102 can be at a pressure greater than atmospheric pressure. The bulk gas mixture 114 can be at a pressure of less than about 150 psig; less than about 100 psig; less than about 75 psig; less than about 60 psig; less than about 50 psig; less than about 40 psig; less than about 30 psig; less than about 20 psig; less than about 15 psig; less than about 10 psig; less than about 5 psig; or less than about 1 psig.

In at least some instances, the rate of the OCM reaction within the one or more vessels 102 can be influenced, adjusted, or controlled based, at least in part, on the temperature of the bulk gas mixture 114. The temperature of the bulk gas mixture 114 can be adjusted by adjusting the temperature of the methane source 106, the oxidant 108, or both the methane source 106 and the oxidant 108. In some instances, the bulk gas mixture 114 may be passed through one or more thermal transfer devices prior to entering the one or more vessels 102. The bulk gas mixture 114 in the one or more vessels 102 can be at a temperature of less than about 600° C.; less than about 575° C.; less than about 550° C.; less than about 525° C.; less than about 500° C.; less than about 450° C.; or less than about 400° C.

The composition of the bulk gas mixture 114 depends on the composition of the constituent methane source 106 and the constituent oxidant 108. Adjusting the concentration of methane or oxygen in the bulk gas mixture 114 will beneficially or adversely impact the formation of desired products such as ethylene and will also control the rate of the exothermic OCM reaction. The methane concentration within the bulk gas mixture 114 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %. The oxygen concentration within the bulk gas mixture 114 in the one or more vessels 102 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %. Although not shown in FIG. 1, in at least some situations, one or more $C_{2+}$ alkane, alkene, alkyne, or aromatic hydrocarbons may be added to the bulk gas mixture 114. The $C_{2+}$ hydrocarbon concentration within the bulk gas mixture 114 in the one or more vessels can be less than about 10 mol %; less than about 5 mol %; less than about 3 mol %; less than about 2 mol %; less than about 1 mol %; less than about 0.5 mol %; or less than about 0.05 mol %.

In one or more embodiments, the oxygen concentration in the bulk gas mixture 114 can be advantageously adjusted to control the rate of the exothermic OCM reaction within the one or more vessels 102. In some embodiments, the oxygen concentration within the bulk gas mixture 114 can be measured and adjusted via one or more feedback controllers communicably coupled to one or more final control elements (not shown in FIG. 1) that control the oxygen concentration within the oxidant 108.

The methane-to-oxygen stoichiometric ratio in the bulk gas mixture 114 will also affect the overall conversion of raw materials to one or more preferred products such as ethylene. Establishing the stoichiometric ratio, expressed as methane molar concentration to oxygen molar concentration, within the bulk gas mixture 114 such that oxygen is the limiting reagent (i.e., maintaining a stoichiometric ratio of greater than 2:1) may advantageously minimize the likelihood of a detonation or deflagration occurring within the one or more vessels 102. One or more analyzers may be used to determine either or both the methane and the oxygen concentration(s) in the bulk gas mixture 114 and provide a process signal input indicative of the concentration(s) to one or more flow or composition controllers. The one or more controllers can provide an output signal to one or more final control elements, for example one or more flow control valves used to control or otherwise adjust the flow of either or both the methane source and the oxidant to the bulk gas mixture 114. In at least some embodiments, the stoichiometric ratio (expressed as methane molar concentration to oxygen molar concentration) in the gas mixture can be greater than about 2:1; greater than about 2.25:1; greater than about 2.5:1; greater than about 2.75:1; greater than about 3:1; greater than about 3.5:1; greater than about 4:1; greater than about 4.5:1; greater than about 5:1; greater than about 7.5:1; or greater than about 10:1.

In at least some embodiments, if stoichiometric ratio in the bulk gas mixture 114 falls into a range where methane becomes the limiting reagent (i.e., excess oxygen is present) the risk of detonation or deflagration within the one or more vessels 102 may increase to an unacceptable level. In at least some circumstances, automatic or manual controls may reduce the methane concentration, the oxygen concentration, or both the methane and the oxygen concentration in the bulk gas mixture 114 to zero when the stoichiometric ratio in the gas mixture is less than about 2:1; less than about 1.9:1; less than about 1.8:1; less than about 1.7:1; less than about 1.6:1; less than about 1.5:1; less than about 1.4:1; less than about 1.3:1; less than about 1.2:1; or less than about 1.1:1.

In some instances, one or more automated control systems may be operably coupled to the OCM reactor 102. In at least some embodiments, such automated control systems may use correlations capable of determining the formation of flammable or explosive conditions in the bulk gas mixture 114. Such correlations may be experimentally derived, or determined from other sources, e.g., correlations known in the art. Such correlations may be derived from process conditions such as the gas phase composition (e.g., oxidant concentration) within the OCM reactor 102, the OCM reactor catalyst bed 104, the bulk gas mixture 114 or the OCM gas 110, or the temperature or temperature rate of change within the OCM reactor 102, the OCM reactor catalyst bed 104, the bulk gas mixture 114, or the OCM gas 110. Instrumentation, such as sensors, transmitters, and the like, and controls, such as single or multi-loop controllers, programmable logic controllers, and distributed control systems, suitable for the measurement and control of gas (e.g., methane, oxygen, nitrogen, ethane, ethylene, etc.) composition and concentration, temperature, pressure are well known in the art and are not addressed herein for brevity. Responsive to the determination that an explosive or flammable bulk gas mixture 114 is likely, appropriate control measures such as limiting or restricting the quantity of methane source 106 or oxidant 108 added to the OCM reactor 102.

Additional safeguards against deflagration or detonation may include, but are not limited to, maintaining the methane/oxygen mixture in the bulk gas mixture 114 at a temperature less than the auto-ignition temperature of the mixture prior to heating the bulk gas to the reaction temperature in the OCM reactor 102. In at least some embodiments, where the bulk gas 114 is at or above the auto-ignition temperature, the ratio of methane to oxygen in the bulk gas 114 may be maintained above the upper flammability limit of the mixture at the operating pressure of the OCM reactor 102. Such safeguards may include, but are not limited to, one or more manual control systems, one or more automated control systems, or any other control devices, systems or final control elements capable of adjusting, limiting, controlling, or altering the quantities of methane and oxygen introduced to the OCM reactor 102.

Products

At least a portion of the methane present in the methane source 106 can react in the presence of the one or more catalysts 104 to provide one or more $C_{2+}$ hydrocarbons including at least ethane and ethylene. The hydrogen liberated during the conversion of methane to the one or more $C_{2+}$ hydrocarbons combines with the oxygen to form water vapor. The oxygen present also combines with at least a portion of the carbon present in the methane to form carbon dioxide in the OCM gas 110. The overall conversion of methane and oxygen to one or more $C_{2+}$ hydrocarbons is dependent upon at least, catalyst composition, reactant concentration, and reaction temperature and pressure within the one or more vessels 102 and the thermal profile through the one or more catalysts 104, the maximum temperature within the one or more catalysts 104, the maximum temperature rise within the one or more catalysts, or combinations thereof.

In addition to the one or more $C_{2+}$ hydrocarbons, the OCM gas 110 removed from the one or more vessels 102 may also contain residual unreacted methane, residual unreacted oxygen, water, and carbon dioxide. Ethane will be present in the OCM gas 110. The ethane concentration within the OCM gas 110 can be at least about 0.25 mol %; at least about 0.5 mol %; at least about 0.75 mol %; at least about 1 mol %; at least about 1.5 mol %; at least about 2 mol %; at least about 2.5 mol %; at least about 3 mol %; at least about 3.5 mol %; at least about 4 mol %; at least about 4.5 mol %; or at least about 5 mol %. Ethylene will also be present in the OCM gas 110. The ethylene concentration within the OCM gas 110 can be at least about 0.25 mol %; at least about 0.5 mol %; at least about 0.75 mol %; at least about 1 mol %; at least about 1.5 mol %; at least about 2 mol %; at least about 2.5 mol %; at least about 3 mol %; at least about 3.5 mol %; at least about 4 mol %; at least about 4.5 mol %; or at least about 5 mol %.

The conversion of methane to higher molecular weight hydrocarbons, such as ethane and ethylene is dependent upon the residence time of reactants such as methane, ethane, and higher hydrocarbons in the OCM reactor 102. In particular, the ratio of ethane to ethylene is dependent upon the residence time of reactants such as methane, ethane, and higher hydrocarbons in the OCM reactor 102 at temperatures in excess of about 800° C. Experience has indicated the formation of ethylene within the OCM reactor 102 may occur as a secondary reaction that may rely upon a steam or thermal cracking process rather than an oxidative process. Thus, the conversion of ethane to ethylene may occur at the elevated temperatures of the OCM reaction, either in portions of the OCM reactor 102 or immediately following the OCM reactor 102 where the oxidant concentration is reduced.

Maintaining oxygen as a limiting reagent in the bulk gas mixture 114 provides a quantity unreacted methane in the OCM gas 110. The concentration of unreacted methane within the OCM gas 110 will vary over time with the aging of the one or more catalysts in the at least one catalyst bed 104. In some instances, the methane concentration in the OCM gas 110 may tend to increase over time with the aging of the one or more catalysts in the at least one catalyst bed 104. The methane concentration in the OCM gas 110 can be less than about 40 mol %; less than about 30 mol %; less than about 25 mol %; less than about 20 mol %; less than about 15 mol %; less than about 10 mol %; less than about 5 mol %; or less than about 1 mol %. Unreacted methane may be separated from the OCM gas 110 for recycle, or may be used as a reactant if all or a portion of the OCM gas 110 is used to provide at least a portion of the methane source 106 in one or more subsequent vessels 102.

Unreacted oxygen may also be present in the OCM gas 110. The concentration of oxygen within the OCM gas 110 may vary over time with the aging of the one or more catalysts in the at least one catalyst bed 104. In some instances, the oxygen concentration in the OCM gas 110 may tend to increase over time with the aging of the one or more catalysts in the at least one catalyst bed 104. The oxygen concentration in the OCM gas 110 can be less than about 10 mol %; less than about 8 mol %; less than about 5 mol %; less than about 3 mol %; less than about 2 mol %; less than about 1 mol %; less than about 0.5 mol %; or less than about 0.1 mol %. Unreacted oxygen may be separated from the OCM gas 110 for recycle, or may be used as a reactant if all or a portion of the OCM gas 110 is used to provide at least a portion of the methane source 106 in one or more subsequent vessels 102.

Carbon dioxide is a product of the complete combustion of methane and also a catalytic byproduct of the combination of oxygen and carbon in the presence of the one or more catalysts in the at least one catalyst bed 114. In some instances, the carbon dioxide concentration in the OCM gas 110 may tend to increase over time with the aging of the one or more catalysts in the at least one catalyst bed 104. The carbon dioxide concentration in the OCM gas 110 can be less than about 10%; less than about 5 mol %; less than about 4 mol %; less than about 3 mol %; less than about 2 mol %; less than about 1 mol %; or less than about 0.5 mol.

As noted above, the OCM product gas typically includes ethane as one component, either as an unreacted feedgas component or an OCM reaction co-product. In certain embodiments, at least a portion of the ethane present in the OCM gas 110 can be separated from the OCM gas 110 and recycled back into one or more injection points within the OCM reactor system, in order to convert that ethane to ethylene. In some embodiments, at least a portion of the ethane is separated from the OCM product gas (e.g., by passing the OCM gas 110 through a downstream or post-production cryogenic separaton process, see, e.g., U.S. patent application Ser. No. 13/739,954, filed Jan. 11, 2013, and incorporated herein by reference in its entirety for all purposes). In at least some instances, at least a portion of the separated ethane may be re-injected directly into one of the OCM reactors 102 at one or more points in a multistage OCM reactor system, including within an intermediate zone in a single catalyst bed. The injection point may include any one or more of the sequentially coupled OCM reactors 102 forming the reactor train. In one or more preferred embodiments, however, the ethane may be injected into the OCM reactor system either at an intermediate portion of one or more OCM reactors 102, or even more preferably, into the OCM gas 110 at the exit of the final OCM reactor 102 in an OCM reactor train, prior to cooling of the OCM gas 110. In particular, by injecting the ethane into the high temperature OCM gas 110, advantage can be taken of the process conditions in the OCM gas 110 to steam crack the ethane to ethylene. While this steam cracking of ethane to ethylene is also achieved by injecting the ethane at an earlier stage, the prolonged exposure to the elevated temperature may detrimentally result in greater combustion of the ethane and ethylene through the OCM reactors 102. Although described in terms of recycled ethane from the OCM product gas, it will be appreciated that completely exogenous sources of ethane may supply the injected ethane, e.g., an ethane output from an NGL processing facility, or the like.

In at least some embodiments, one or more higher hydrocarbons can be combined with the OCM gas 110 prior to cooling the OCM gas in the thermal transfer device 112. In at least some embodiments, one or more higher hydrocarbons can be introduced to the catalyst bed 104 in the OCM reactor 102. To reduce the likelihood of forming undesirable byproducts, the oxygen concentration of the OCM gas 110 at the point of combination with the one or more higher hydrocarbons can be less than about 2 mol %, less than about 1 mol %, or less than 0.5 mol %. To improve the yield of desirable higher hydrocarbon products, the temperature of the OCM gas 110 at the point of combination with the one or more higher hydrocarbons can be greater than about 750° C.; greater than about 800° C.; greater than about 850° C.; or greater than about 900° C. In at least some embodiments the temperature of the higher hydrocarbons may be increased prior to combination with the OCM gas 110 or introduction to the OCM reactor 102 to minimize the cooling effect of the higher hydrocarbons on the OCM gas 110. In at least some embodiments, prior to combining with the OCM gas 110 or being introduced to the OCM reactor, the temperature of the higher hydrocarbons can be increased to a temperature less than about 750° C.; less than about 700° C.; less than about 650° C.; or less than about 600° C.

Figure 11A:
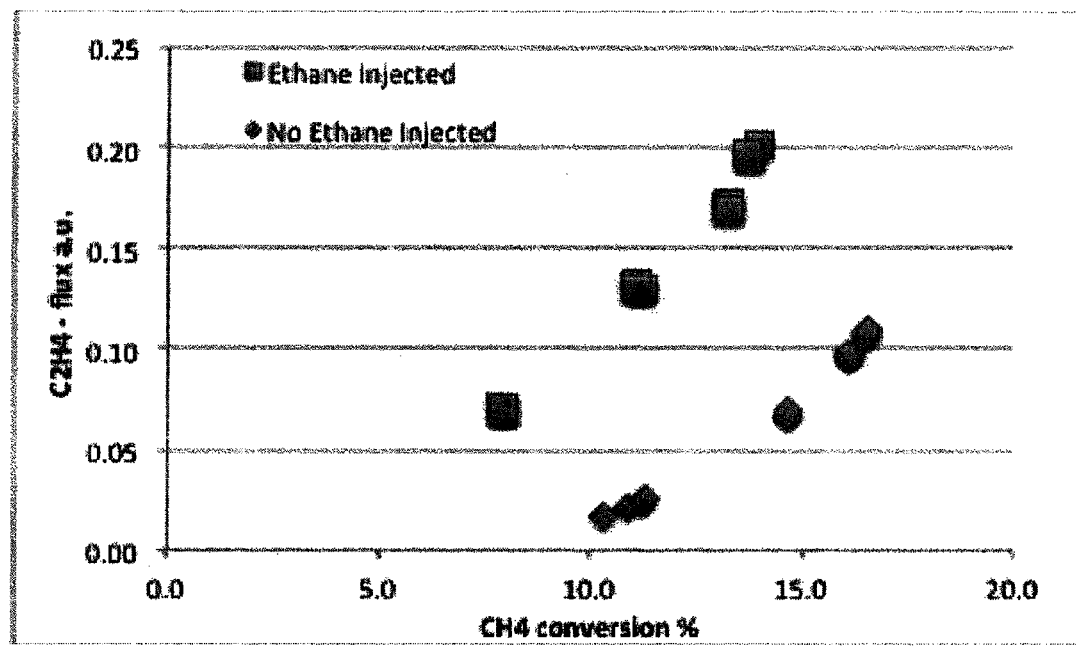
FIG. 11A shows a plot of an illustrative relationship between methane conversion and ethylene flux for an example oxidative coupling of methane reactor system.
Figure 11B:
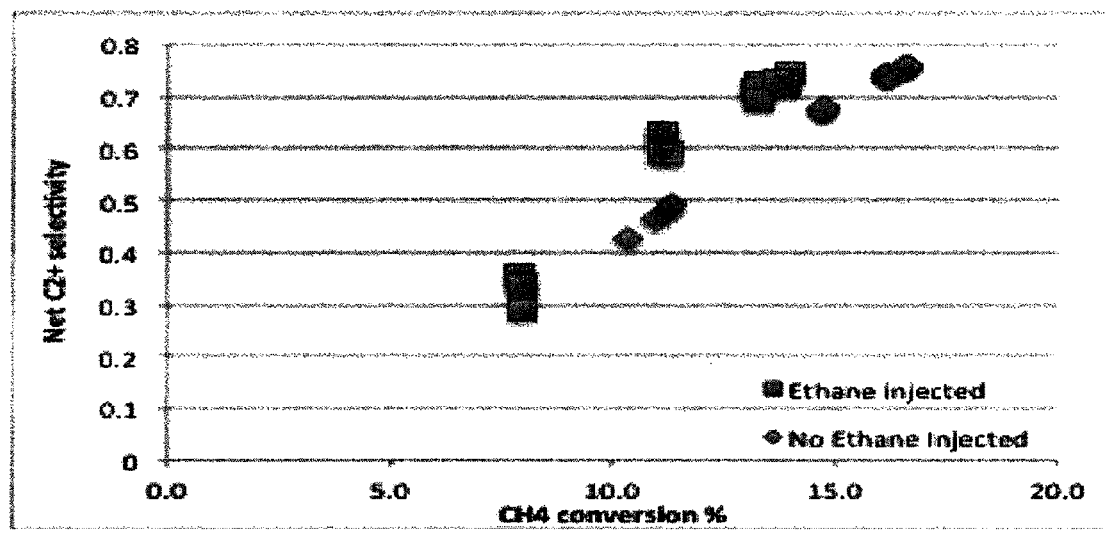
FIG. 11B shows a plot of an illustrative relationship between methane conversion and higher hydrocarbon selectivity for an example oxidative coupling of methane reactor system.

Significant cracking of ethane to ethylene occurs when the ethylene is introduced within the catalyst bed 104 of the OCM reactor 102. At the same time the amount of selectivity of the OCM reaction is only slightly affected by the addition of up to 8 mol % ethane into the OCM gas 110 upstream of the thermal transfer device 112. In such instances, the thermal transfer device 112 may advantageously serve as a quench device to halt the steam or thermal cracking of the OCM gas 110. FIGS. 11A and 11B present experimental data demonstrating an increase in ethylene flux from the OCM reactor 102 while noting little change in OCM selectivity from methane to C2 hydrocarbons in consequence to the addition of ethane to the catalyst bed 104 in the OCM reactor 102. The use of the OCM gas 110 exiting the OCM reactor 102 as a heat source and diluent for cracking ethane may be applicable to $C_{3+}$ hydrocarbons where the temperature of the OCM gas 110 is maintained at a level limiting the conversion of the $C_{3+}$ hydrocarbons to undesirable byproducts such as coke, particularly when the $C_{3+}$ hydrocarbons include long chain alkanes.

Accordingly, in at least some embodiments, ethane or one or more higher hydrocarbons may be introduced at any point in the OCM reactor 102 including in the methane source 106, the bulk gas mixture 114, or at various points within the OCM reactor 102, for instance at one or more points within the catalyst bed 104. In at least some embodiments, ethane may be preferentially introduced at locations in the OCM reactor system where the concentration of the oxidant 108 is reduced to lessen the formation of undesirable reaction byproducts such as coke and similar long chain combustion byproducts. The ethane or one or more higher hydrocarbons may be introduced to the catalyst bed 104 using one or more distributors fabricated from one or more non-reactive materials, for instance a ceramic oxide coated high temperature compatible metal or metal alloy such as Inconel, Hastelloy, and Alloy N155 and the like. In at least some implementations the one or more distributors may include a thermal control system to limit the temperature of the distributor and thereby lessen the likelihood of occurrence of premature cracking of the ethane or the one or more higher hydrocarbons prior to the introduction of the ethane or one or more higher hydrocarbons to the OCM reactor 102.

In at least some embodiments, one or more higher hydrocarbons available as a commodity (e.g., ethane, propane, butane, etc.) may be introduced to the catalyst bed 104 in the OCM reactor 102. In such embodiments, the addition rate (e.g., moles/hr) of higher hydrocarbons to the catalyst bed 104 in the OCM reactor 102 can be equal to the methane addition rate from the methane source 106, one half of the methane addition rate from the methane source 106, or about one quarter of the methane addition rate from the methane source 106.

In at least some embodiments, one or more hydrocarbons generated as byproducts in an ethylene to liquids ("ETL") production facility may be introduced to the OCM gas 110 exiting the OCM reactor 102. In such embodiments, the temperature of the OCM gas 110 may be adjusted prior to combining with the ETL hydrocarbon byproducts to minimize the likelihood of coke formation within the OCM gas 110. In at least some embodiments, the temperature of the OCM gas 110 may be adjusted to a temperature of from about 800° C. to about 850° C.; from about 750° C. to about 800° C.; or from about 700° C. to about 750° C.

The addition of one or more higher hydrocarbons or one or more ETL hydrocarbon byproducts to the catalyst bed 104 in the OCM reactor 102 or to the OCM gas 110 can increase the likelihood of a detonation or deflagration event if greater than expected levels of oxidant are present at the point of addition of the one or more higher hydrocarbons or one or more ETL hydrocarbon byproducts. Responsive montoring and control of the thermal profile in catalyst bed 104 or a responsive monitoring of oxidant level in the OCM reactor 102 may be employed to proactively adjust or halt the flow of one or more higher hydrocarbons or one or more ETL hydrocarbon byproducts to the OCM reactor under high oxidant concentration conditions.

Catalysts

The catalytic materials described herein generally comprise one or more catalysts in combination with a support, binder and/or diluent material. In some embodiments, diluents are selected from bulk materials (e.g. commercial grade), nano materials (nanowires, nanorods, nanoparticles, etc.) and combinations thereof. Catalysts useful in the disclosed catalytic forms and formulations include any heterogeneous catalyst. The catalysts can have various elemental components and activity in a variety of reactions. In certain embodiments the catalyst is an OCM active catalyst. The exact elemental components or morphological form of the catalysts is not critical, provided they may be used in combination with the supports, diluents and/or binders described herein. In this regard, catalysts useful for practice of various embodiments of the invention include any bulk and/or nanostructured catalyst in any combination. For example, in some embodiments the catalyst comprises a catalyst as described in co-pending U.S. application Ser. No. 13/115,082 (U.S. Pub. No. 2012/0041246); U.S. Application entitled "Catalysts for Petrochemical Analysis", filed May 24, 2012; U.S. Provisional Application Nos. 61/489,651; 61/564,832; 61/564,834 and 61/564,836; and U.S. Provisional Application entitled "Nanowire Catalysts", filed May 24, 2012, the full disclosures of which are hereby incorporated by reference in their entirety for all purposes to the extent that material in the incorporated applications does not contradict material contained herein.

As discussed herein, the conversion of methane and oxygen to one or more hydrocarbons occurs as a gas phase catalytic reaction. Any conventionally produced bulk catalyst may be used to promote the catalytic reaction, however in at least one preferred embodiment the catalyst includes at least one inorganic catalytic polycrystalline nanowire. Catalysts useful in the embodiments described herein include heterogeneous catalysts with various elemental components and having activity in a variety of reactions. In certain embodiments the catalyst is an OCM active catalyst. The exact elemental components or morphological form of the catalysts is not critical, provided they may be used in combination with the supports, diluents and/or binders described herein. In this regard, catalysts useful for practice of various embodiments of the invention include any bulk and/or nanostructured catalyst in any combination. In certain embodiments, the catalyst is a nanowire catalyst, for example a nanowire comprising a metal oxide, metal hydroxide, metal oxyhydroxide, metal oxycarbonate, metal carbonate or combinations thereof. In some other related embodiments, the catalyst is an inorganic nanowire comprising one or more metal elements from any of Groups 1 through 7, lanthanides, actinides or combinations thereof and a dopant comprising a metal element, a semi-metal element, a non-metal element or combinations thereof.

In some other embodiments, the catalyst is an inorganic catalytic polycrystalline nanowire, the nanowire having a ratio of effective length to actual length of less than one and an aspect ratio of greater than ten as measured by TEM in bright field mode at 5 keV, wherein the nanowire comprises one or more elements from any of Groups 1 through 7, lanthanides, actinides or combinations thereof. Such a nanowire may optionally include one or more dopants.

In other embodiments, the present invention is directed to catalyst forms and formulations comprising a catalytic nanowire which comprises at least four different doping elements, wherein the doping elements are selected from a metal element, a semi-metal element and a non-metal element. In other embodiments, the catalyst is a catalytic nanowire comprising at least two different doping elements, wherein the doping elements are selected from a metal element, a semi-metal element and a non-metal element, and wherein at least one of the doping elements is K, Sc, Ti, V, Nb, Ru, Os, Ir, Cd, In, Tl, S, Se, Po, Pr, Tb, Dy, Ho, Er, Tm, Lu or an element selected from any of groups 6, 7, 10, 11, 14, 15 or 17.

Other embodiments include catalytic forms and formulations wherein the catalyst is a catalytic nanowire comprising at least one of the following dopant combinations: Eu/Na, Sr/Na, Na/Zr/Eu/Ca, Mg/Na, Sr/Sm/Ho/Tm, Sr/W, Mg/La/K, Na/K/Mg/Tm, Na/Dy/K, Na/La/Dy, Na/La/Eu, Na/La/Eu/In, Na/La/K, Na/La/Li/Cs, K/La, K/La/S, K/Na, Li/Cs, Li/Cs/La, Li/Cs/La/Tm, Li/Cs/Sr/Tm, Li/Sr/Cs, Li/Sr/Zn/K, Li/Ga/Cs, Li/K/Sr/La, Li/Na, Li/Na/Rb/Ga, Li/Na/Sr, Li/Na/Sr/La, Li/Sm/Cs, Ba/Sm/Yb/S, Ba/Tm/K/La, Ba/Tm/Zn/K, Cs/K/La, Cs/La/Tm/Na, Cs/Li/K/La, Sm/Li/Sr/Cs, Sr/Cs/La, Sr/Tm/Li/Cs, Zn/K, Zr/Cs/K/La, Rb/Ca/In/Ni, Sr/Ho/Tm, La/Nd/S, Li/Rb/Ca, Li/K, Tm/Lu/Ta/P, Rb/Ca/Dy/P, Mg/La/Yb/Zn, Rb/Sr/Lu, Na/Sr/Lu/Nb, Na/Eu/Hf, Dy/Rb/Gd, Na/Pt/Bi, Rb/Hf, Ca/Cs, Ca/Mg/Na, Hf/Bi, Sr/Sn, Sr/W, Sr/Nb, Zr/W, Y/W, Na/W, Bi/W, Bi/Cs, Bi/Ca, Bi/Sn, Bi/Sb, Ge/Hf, Hf/Sm, Sb/Ag, Sb/Bi, Sb/Au, Sb/Sm, Sb/Sr, Sb/W, Sb/Hf, Sb/Yb, Sb/Sn, Yb/Au, Yb/Ta, Yb/W, Yb/Sr, Yb/Pb, Yb/W, Yb/Ag, Au/Sr, W/Ge, Ta/Hf, W/Au, Ca/W, Au/Re, Sm/Li, La/K, Zn/Cs, Na/K/Mg, Zr/Cs, Ca/Ce, Na/Li/Cs, Li/Sr, Cs/Zn, La/Dy/K, Dy/K, La/Mg, Na/Nd/In/K, In/Sr, Sr/Cs, Rb/Ga/Tm/Cs, Ga/Cs, K/La/Zr/Ag, Lu/Fe, Sr/Tm, La/Dy, Sm/Li/Sr, Mg/K, Li/Rb/Ga, Li/Cs/Tm, Zr/K, Li/Cs, Li/K/La, Ce/Zr/La, Ca/Al/La, Sr/Zn/La, Sr/Cs/Zn, Sm/Cs, In/K, Ho/Cs/Li/La, Cs/La/Na, La/S/Sr, K/La/Zr/Ag, Lu/Tl, Pr/Zn, Rb/Sr/La, Na/Sr/Eu/Ca, K/Cs/Sr/La, Na/Sr/Lu, Sr/Eu/Dy, Lu/Nb, La/Dy/Gd, Na/Mg/Tl/P, Na/Pt, Gd/Li/K, Rb/K/Lu, Sr/La/Dy/S, Na/Ce/Co, Na/Ce, Na/Ga/Gd/Al, Ba/Rh/Ta, Ba/Ta, Na/Al/Bi, Cs/Eu/S, Sm/Tm/Yb/Fe, Sm/Tm/Yb, Hf/Zr/Ta, Rb/Gd/Li/K, Gd/Ho/Al/P, Na/Ca/Lu, Cu/Sn, Ag/Au, Al/Bi, Al/Mo, Al/Nb, Au/Pt, Ga/Bi, Mg/W, Pb/Au, Sn/Mg, Zn/Bi, Gd/Ho, Zr/Bi, Ho/Sr, Gd/Ho/Sr, Ca/Sr, Ca/Sr/W, Sr/Ho/Tm/Na, Na/Zr/Eu/Tm, Sr/Ho/Tm/Na, Sr/Pb, Sr/W/Li, Ca/Sr/W or Sr/Hf.

In other embodiments, the catalyst comprises a lanthanide mixed oxide compound. For example, in certain embodiments the catalyst is a catalytic nanowire comprising $Ln1_{4-x}Ln2_xO_6$ and a dopant comprising a metal element, a semi-metal element, a non-metal element or combinations thereof, wherein Ln1 and Ln2 are each independently a lanthanide element, wherein Ln1 and Ln2 are not the same and x is a number ranging from greater than 0 to less than 4. In other embodiments, the catalyst is a catalytic nanowire comprising a mixed oxide of Y—La, Zr—La, Pr—La, Ce—La or combinations thereof and at least one dopant selected from a metal element, a semi-metal element and a non-metal element.

In some other embodiments, the catalyst comprises a mixed oxide of a rare earth element and a Group 13 element, wherein the catalytic nanowire further comprises one or more Group 2 elements. In some more specific embodiments, the foregoing catalyst is a nanowire catalyst.

In another embodiment the catalyst comprises a lanthanide oxide doped with an alkali metal, an alkaline earth metal or combinations thereof, and at least one other dopant from groups 3-16. In some more specific embodiments, the foregoing catalyst is a nanowire catalyst.

The catalysts for use in conjunction with the invention preferably provide a C2+ selectivity of greater than 50%, greater than 55%, greater than 60%, greater than 65%, greater than 70%, greater than 75%.

The catalysts typically also provide methane conversions of greater than 10%, greater than 12%, greater than 15%, greater than 20%, greater than 22%, greater than 25%, and even greater than 30%.

In certain preferred embodiments, the catalysts will provide selectivity of 50% or greater with conversion of greater than 10%, greater than 15%, greater than 20%, greater than 25%, or greater than 30%. Likewise, in still further embodiments, the catalysts of certain embodiments will provide a selectivity of 55% or greater with conversion of greater than 10%, greater than 15%, greater than 20%, greater than 25%, or greater than 30%. Further in still other embodiments, the catalysts of certain embodiments will provide a selectivity of 60% or greater with conversion of greater than 10%, greater than 15%, greater than 20%, greater than 25%, or greater than 30%.

In still other embodiments, the catalyst comprises a single pass methane conversion in an OCM reaction catalyzed by the nanowire is greater than 10%, greater than 15%, greater than 20%, or even greater than 25% for example in some such embodiments the catalyst is a catalytic nanowire. In other embodiments the catalyst comprises a C2 selectivity of greater than 10%, greater than 20%, greater than 30%, greater than 40%, greater than 50%, or even greater than 60%, in the OCM reaction when the OCM reaction is performed with an oxygen source other than air or $O_2$. In certain embodiments of the foregoing, the catalyst is a catalytic nanowire.

In yet other embodiments, the catalyst comprises a mixed oxide of magnesium and manganese, wherein the catalyst further comprises lithium and boron dopants and at least one doping element from groups 4, 9, 12, 13 or combinations thereof. In other examples, the catalyst comprises an oxide of a rare earth element, wherein the catalyst further comprises at least one doping element from groups 1-16, lanthanides, actinides or combinations thereof. In still other examples, the catalyst comprises a mixed oxide of manganese and tungsten, wherein the catalyst further comprises a sodium dopant and at least one doping element from groups 2, 4-6, 8-15, lanthanides or combinations thereof. In yet other embodiments, the catalyst comprises a mixed oxide of a lanthanide and tungsten, wherein the catalyst further comprises a sodium dopant and at least one doping element from groups 2, 4-15, lanthanides or combinations thereof, wherein the catalyst comprises a $C_2$ selectivity of greater than 50% and a methane conversion of greater than 10%, 15% or even 20% when the catalyst is employed as a heterogenous catalyst in the oxidative coupling of methane at a reactor inlet temperature of 750° C. or less.

In other aspects, the catalytic forms and formulations comprise a catalyst comprising a mixed oxide of manganese and tungsten, wherein the catalyst further comprises a sodium dopant and at least one doping element from groups 2, 16 or combinations thereof.

In some other embodiments, the catalyst comprises a rare earth oxide and one or more dopants, wherein the dopant comprises Eu/Na, Sr/Na, Na/Zr/Eu/Ca, Mg/Na, Sr/Sm/Ho/Tm, Sr/W, Mg/La/K, Na/K/Mg/Tm, Na/Dy/K, Na/La/Dy, Na/La/Eu, Na/La/Eu/In, Na/La/K, Na/La/Li/Cs, K/La, K/La/S, K/Na, Li/Cs, Li/Cs/La, Li/Cs/La/Tm, Li/Cs/Sr/Tm, Li/Sr/Cs, Li/Sr/Zn/K, Li/Ga/Cs, Li/K/Sr/La, Li/Na, Li/Na/Rb/Ga, Li/Na/Sr, Li/Na/Sr/La, Li/Sm/Cs, Ba/Sm/Yb/S, Ba/Tm/K/La, Ba/Tm/Zn/K, Cs/K/La, Cs/La/Tm/Na, Cs/Li/K/La, Sm/Li/Sr/Cs, Sr/Cs/La, Sr/Tm/Li/Cs, Zn/K, Zr/Cs/K/La, Rb/Ca/In/Ni, Sr/Ho/Tm, La/Nd/S, Li/Rb/Ca, Li/K, Tm/Lu/Ta/P, Rb/Ca/Dy/P, Mg/La/Yb/Zn, Rb/Sr/Lu, Na/Sr/Lu/Nb, Na/Eu/Hf, Dy/Rb/Gd, Na/Pt/Bi, Rb/Hf, Ca/Cs, Ca/Mg/Na, Hf/Bi, Sr/Sn, Sr/W, Sr/Nb, Zr/W, Y/W, Na/W, Bi/W, Bi/Cs, Bi/Ca, Bi/Sn, Bi/Sb, Ge/Hf, Hf/Sm, Sb/Ag, Sb/Bi, Sb/Au, Sb/Sm, Sb/Sr, Sb/W, Sb/Hf, Sb/Yb, Sb/Sn, Yb/Au, Yb/Ta, Yb/W, Yb/Sr, Yb/Pb, Yb/W, Yb/Ag, Au/Sr, W/Ge, Ta/Hf, W/Au, Ca/W, Au/Re, Sm/Li, La/K, Zn/Cs, Na/K/Mg, Zr/Cs, Ca/Ce, Na/Li/Cs, Li/Sr, Cs/Zn, La/Dy/K, Dy/K, La/Mg, Na/Nd/In/K, In/Sr, Sr/Cs, Rb/Ga/Tm/Cs, Ga/Cs, K/La/Zr/Ag, Lu/Fe, Sr/Tm, La/Dy, Sm/Li/Sr, Mg/K, Li/Rb/Ga, Li/Cs/Tm, Zr/K, Li/Cs, Li/K/La, Ce/Zr/La, Ca/Al/La, Sr/Zn/La, Sr/Cs/Zn, Sm/Cs, In/K, Ho/Cs/Li/La, Cs/La/Na, La/S/Sr, K/La/Zr/Ag, Lu/Tl, Pr/Zn, Rb/Sr/La, Na/Sr/Eu/Ca, K/Cs/Sr/La, Na/Sr/Lu, Sr/Eu/Dy, Lu/Nb, La/Dy/Gd, Na/Mg/Tl/P, Na/Pt, Gd/Li/K, Rb/K/Lu, Sr/La/Dy/S, Na/Ce/Co, Na/Ce, Na/Ga/Gd/Al, Ba/Rh/Ta, Ba/Ta, Na/Al/Bi, Cs/Eu/S, Sm/Tm/Yb/Fe, Sm/Tm/Yb, Hf/Zr/Ta, Rb/Gd/Li/K, Gd/Ho/Al/P, Na/Ca/Lu, Cu/Sn, Ag/Au, Al/Bi, Al/Mo, Al/Nb, Au/Pt, Ga/Bi, Mg/W, Pb/Au, Sn/Mg, Zn/Bi, Gd/Ho, Zr/Bi, Ho/Sr, Gd/Ho/Sr, Ca/Sr, Ca/Sr/W, Na/Zr/Eu/Tm, Sr/Ho/Tm/Na, Sr/Pb, Sr/W/Li, Ca/Sr/W, Sr/Hf or combinations thereof.

In various embodiments of the foregoing catalysts, the catalyst comprises a $C_2$ selectivity of greater than 50% and a methane conversion of greater than 20% when the catalyst is employed as a heterogenous catalyst in the oxidative coupling of methane at a temperature of 750° C. or less.

In various embodiments of the foregoing catalysts, the catalyst comprises a $C_2$ selectivity of greater than 50% and a methane conversion of greater than 10%, 15%, 20% or even 25% when the catalyst is employed as a heterogenous catalyst in the oxidative coupling of methane at a temperature of 750° C. or less. Some or all of the catalysts may be used directly without a support structure, for example in the form of loose catalyst, agglomerated catalyst, sintered catalyst, catalyst pressed or otherwise formed into various shapes such as rings, saddles, spoked wheels, snowflakes, and the like that provide a high ratio of exposed surface area to volume. Some or all of the catalysts may be affixed, bonded or otherwise attached to an inert underlying substrate that provides structural strength and form to the catalyst. The underlying substrate may also provide a plurality of gas flow channels, for example where the substrate is structured in the form of a hexagonal honeycomb structure or a square "egg-crate" structure.

In some embodiments the nanowires forming the nanowire catalyst may have a surface area of between 0.0001 and 3000 m$^2$/g, between 0.0001 and 2000 m$^2$/g, between 0.0001 and 1000 m$^2$/g, between 0.0001 and 500 m$^2$/g, between 0.0001 and 100 m$^2$/g, between 0.0001 and 50 m$^2$/g, between 0.0001 and 20 m$^2$/g, between 0.0001 and 10 m$^2$/g or between 0.0001 and 5 m$^2$/g. In some embodiments the nanowires have a surface area of between 0.001 and 3000 m$^2$/g, between 0.001 and 2000 m$^2$/g, between 0.001 and 1000 m$^2$/g, between 0.001 and 500 m$^2$/g, between 0.001 and 100 m$^2$/g, between 0.001 and 50 m$^2$/g, between 0.001 and 20 m$^2$/g, between 0.001 and 10 m$^2$/g or between 0.001 and 5 m$^2$/g. In some other embodiments the nanowires have a surface area of between 2000 and 3000 m$^2$/g, between 1000 and 2000 m$^2$/g, between 500 and 1000 m$^2$/g, between 100 and 500 m$^2$/g, between 10 and 100 m$^2$/g, between 5 and 50 m$^2$/g, between 2 and 20 m$^2$/g or between 0.0001 and 10 m$^2$/g. In other embodiments, the nanowires have a surface area of greater than 2000 m$^2$/g, greater than 1000 m$^2$/g, greater than 500 m$^2$/g, greater than 100 m$^2$/g, greater than 50 m$^2$/g, greater than 20 m$^2$/g, greater than 10 m$^2$/g, greater than 5 m$^2$/g, greater than 1 m$^2$/g, greater than 0.0001 m$^2$/g.

Other catalysts useful in the context of the catalytic forms and formulations described herein will be readily apparent to one of ordinary skill in the art.

Referring back to FIG. 1, introduction of the methane source 106 to the one or more vessels 102 may be partially or completely obstructed by one or more final control elements 116. In at least some instances, the final control element 116 includes one or more variable final control elements, for example one or more control valves, suitable for modulating the rate at which the methane source 106 is introduced to the one or more vessels 102. In at least some instances, the final control element 116 includes one or more discrete final control elements, for example a plurality of open/close block valves arranged in a double block and bleed arrangement to affirmatively halt the introduction of the methane source 106 to the one or more vessels 102.

Introduction of the oxidant 108 to the one or more vessels 102 may be partially or completely obstructed by one or more final control elements 118. In at least some instances, the final control element 118 includes one or more variable final control elements, for example one or more control valves, suitable for modulating the rate at which the oxidant 108 is introduced to the one or more vessels 102. In at least some instances, the final control element 118 includes one or more discrete final control elements, for example a plurality of open/close block valves arranged in a double block and bleed arrangement, to affirmatively halt the introduction of the oxidant 108 to the one or more vessels 102.

In at least some embodiments one or more pressure relief devices 120 may be fluidly coupled to each of the one or more vessels 102. The one or more pressure relief devices can be selected, sized, or rated at least in part based upon the volume of each of the respective one or more vessels 102 to which they are fluidly coupled, the expected composition within each of the respective one or more vessels 102 to which they are fluidly coupled, the expected operating temperature of each of the respective one or more vessels 102 to which they are fluidly coupled, the expected operating pressure of each of the respective one or more vessels 102 to which they are fluidly coupled, or any combination thereof. The one or more pressure relief devices 120 may include, but are not limited to, one or more pressure safety valves, one or more rupture discs, or combinations thereof. Where multiple pressure relief devices 120 are fluidly coupled to each of the respective one or more vessels 102, each of the pressure relief devices may have differing structures, fluid connections, pressure activation ratings, temperature ratings, or combinations thereof.

Each of the one or more vessels 102 can have any physical size, shape, or configuration. Where multiple vessels 102 are used, each may have the same size or may of a different size. Each of the one or more vessels 102 can have an operating temperature of less than about 1500° C.; less than about 1250° C.; less than about 1100° C.; less than about 1000° C.; less than about 950° C.; less than about 900° C.; less than about 850° C.; less than about 800° C.; less than about 750° C.; less than about 700° C.; or less than about 650° C. Each of the one or more vessels 102 can be constructed of a material selected based at least in part on the expected operating temperature, operating pressure, and corrosivity of the methane source 106, the oxidant 108, the one or more catalysts, and the OCM gas 110. Example materials of construction for each of the one or more vessels can include, but is not limited to, one or more carbon steel alloys, one or more stainless steel alloys, one or more nickel alloys, or one or more combinations thereof. In at least some instances, a refractory or similar thermally insulative lining may be installed within at least a portion of the one or more vessels 102.

Although depicted as entering the one or more vessels 102 separately, in at least some instances all or a portion of the methane source 106 and the oxidant 108 are mixed, joined or otherwised combined to provide the bulk gas mixture 114 prior to introduction to the one or more vessels 102. Where at least a portion of the methane source 106 and at least a portion of the oxidant 108 are introduced to the one or more vessels 102 separately, one or more structures, systems or devices, for example one or more baffles, vanes, or flow diverters, may be installed within some or all of the one or more vessels 102 to promote the mixing of the methane source 106 and the oxidant 108 to provide a substantially homogeneous bulk gas mixture 114 within the one or more vessels 102. The GHSV through each of the one or more vessels 102 may be the same or different since changes in either the reactant gas flow rate or the volume of each of the one or more vessels 102 will affect the GHSV. The GHSV in each of the one or more reactors can be less than about 100,000 h$^{-1}$; less than about 75,000 h$^{-1}$; less than about 50,000 h$^{-1}$; less than about 40,000 h$^{-1}$; less than about 30,000 h$^{-1}$; less than about 20,000 h$^{-1}$; less than about 10,000 h$^{-1}$; less than about 5,000 h$^{-1}$; less than about 4,000 h$^{-1}$; less than about 2,000 h$^{-1}$; or less than about 1,000 h$^{-1}$.

The temperature gradient or rise rate within the catalyst bed 104 is a function of the temperature, pressure, and composition of the bulk gas mixture 114 as well as the composition of the catalyst bed 104. The temperature gradient or rise rate within the catalyst bed 104 is also a function of the linear velocity of the bulk gas mixture 114 through the catalyst bed 104. The linear velocity of the bulk gas mixture 114 through the catalyst bed 104 can be less than about 50 meters/sec (m/s); less than about 25 m/s; less than about 20 m/s; less than about 15 m/s; less than about 10 m/s; less than about 5 m/s; less than about 2.5 m/s; less than about 1 m/s; less than about 0.5 m/s; less than about 0.1 m/s.

In at least some embodiments, the operating pressure of each of the one or more vessels 102 may be maintained at less than 15 pounds per square inch gauge ("psig") to avoid registration as a pressure vessel under the latest version of the American Society of Mechanical Engineers (ASME®)

Section VIII Pressure Vessel Code ("ASME® Section VIII"). In other instances, the operating pressure of the one or more vessels may be greater than 15 psig and each of the one or more vessels 102 may be an ASME registered pressure vessel under ASME® Section VIII. In those other instances, the operating pressure of the one or more vessels 102 can be less than about 150 psig; less than about 100 psig; less than about 75 psig; less than about 50 psig; or less than about 25 psig.

One or more catalyst beds 104, each containing at least one catalyst, are disposed at least partially within the one or more vessels 102. Within each of the one or more vessels 102, one or more structural supports, for example in the form of a structural frame, structural mesh or structural grating capable of permitting the passage of gases with minimal pressure drop, may extend across all or a portion of the cross-sectional area of each of the one or more vessels 102. Where multiple catalyst beds 104 are used, each of the catalyst beds 104 can be supported using a structural support such as a structural frame, structural mesh or structural grating. The exact construction and structure of the structural support can depend upon the nature, composition, depth, and specific density of the one or more catalysts disposed on the structural support. In some embodiments, the one or more catalysts may be disposed on a rigid carrier structure, such as a honeycomb structure, that is capable of providing structural support for itself and the surrounding carrier structures, in which case the structural support in each of the one or more vessels 120 may be a simple structural framework sized and positioned to support the catalyst carrier structures and imposing minimal, if any, gas phase pressure drop in addition to the inherent pressure drop through the one or more catalysts themselves. In some embodiments, the one or more catalysts may be formed into random or fixed shapes, such as rings, saddles, pellets, trilobes, tablets, rib with holes, spheres, extrusions, spoked wheels, granules, microspheres, and the like, in which case the structural support in each of the one or more vessels 102 may include at least one of a structural support grating or mesh to support the one or more catalysts.

The catalyst bed 104 can include one catalyst having a single chemical composition and single physical shape, one catalyst having a single chemical composition and a plurality of differing physical shapes, a plurality of catalysts each having differing chemical compositions and a single physical shape, a plurality of catalysts each having differing chemical compositions and differing physical shapes, an inert material having a single chemical composition and single physical shape, one inert material having a single chemical composition and a plurality of differing physical shapes, a plurality of inert materials each having differing chemical compositions and a single physical shape, a plurality of inert materials each having differing chemical compositions and differing physical shapes, or combinations thereof.

In at least some embodiments, the catalyst bed 104 may include a plurality of distinct layers, zones, or sections. In at least some embodiments, one or more inert materials may be used as a physical support for the one or more catalysts in each of the one or more catalysts beds 104. The one or more catalyst beds 104 in each of the one or more vessels 102 can have the same or different depth, thickness, composition, or combinations thereof. For example, in at least some embodiments, the one or more catalyst beds 104 can include a base layer of rigid inert support material, one or more layers of structured catalyst including one or more catalyst compositions on a rigid substrate, and one or more layers of loose shaped catalyst. The overall thickness or depth of the one or more catalyst beds 104 can be based in whole or in part on thermal considerations such as the desired overall temperature rise through the one or more catalyst beds 104 or the overall temperature rise through one or more layers within the catalyst bed 104 or the desired overall temperature profile through the one or more catalyst beds 104 or the overall temperature profile through one or more layers within the catalyst bed 104. In some instances, the composition or structure of the one or more catalyst beds 104 in each of the one or more vessels 102 can be based in whole or in part on a desired gas pressure drop through the one or more catalyst beds 104.

In at least some embodiments, each of the one or more catalyst beds 104 can include one or more layers having an individual or combined overall depth or thickness of less than about 300 inches; less than about 200 inches; less than about 100 inches; less than about 80 inches; less than about 60 inches; less than about 48 inches; less than about 42 inches; less than about 36 inches; less than about 30 inches; less than about 24 inches; less than about 18 inches; less than about 12 inches; or less than about 6 inches. The one or more catalyst beds 104 can have a length/diameter ("L/D") ratio of less than about 300; less than about 250; less than about 200; less than about 150; less than about 100; less than about 50; less than about 25; or less than about 10. In at least some situations, each of the one or more catalyst beds 104 can contain a structured catalyst layer including one or more catalysts disposed on a rigid structural support having a thickness of less than about 24 inches; less than about 18 inches; less than about 12 inches; less than about 8 inches; less than about 4 inches; less than about 2 inches; or less than about 1 inch. In at least some situations, each of the one or more catalyst beds 104 can contain a structured inert layer including one or more rigid structural inert supports having a thickness of less than about 24 inches; less than about 18 inches; less than about 12 inches; less than about 8 inches; less than about 4 inches; less than about 2 inches; or less than about 1 inch. In at least some situations, each of the one or more catalyst beds 104 can contain one or more random or unstructured catalyst layers including one or more catalysts having one or more physical or chemical compositions and having a bed thickness of less than about 24 inches; less than about 18 inches; less than about 12 inches; less than about 8 inches; less than about 4 inches; less than about 2 inches; or less than about 1 inch. In at least some situations, each of the one or more catalyst beds 104 can contain one or more random or unstructured inert layers including one or more inerts having one or more physical or chemical compositions and having a bed thickness of less than about 24 inches; less than about 18 inches; less than about 12 inches; less than about 8 inches; less than about 4 inches; less than about 2 inches; or less than about 1 inch.

When the one or more catalyst beds 104 are operated under substantially adiabatic conditions, the temperature rise or increase across the bed can be controlled or by adjusting the temperature of the methane source 106, the oxidant 108, or both the methane source 106 and the oxidant 108. Such control provides the ability to limit the temperature increase through the one or more catalyst beds 104. Under substantially adiabatic conditions, the temperature increase across the one or more catalyst beds 104 can be greater than about 50° C.; greater than about 100° C.; greater than about 150° C.; greater than about 200° C.; or greater than about 250° C. In at least some embodiments, the methane source 106, oxidant 108, or both the methane source 106 and the oxidant 108 may be halted or interrupted to the one or more vessels 102 when the one or more vessels are operated under substantially adiabatic conditions and the temperature increase across or through the one or more catalyst beds is greater than about 100° C.; greater than about 150° C.; greater than about 200° C.; greater than about 250° C.; greater than about 275° C.; greater than about 300° C.; greater than about 325° C.; or greater than about 350° C.

When the one or more catalyst beds 104 are operated under substantially adiabatic conditions, the maximum temperature attained within the one or more catalyst beds 104 also can be controlled by adjusting the temperature, pressure, flow, or composition of the methane source 106, the oxidant 108, the bulk gas mixture 114, or combinations thereof. Such control provides the ability to limit the maximum temperature attained within the one or more catalyst beds 104. Under substantially adiabatic conditions, the maximum temperature within the one or more catalyst beds 104 can be less than about 1000° C.; less than about 950° C.; less than about 900° C.; less than about 850° C.; less than about 800° C.; less than about 750° C.; less than about 700° C.; less than about 650° C.; or less than about 600° C. Under substantially adiabatic conditions, the operating temperature within the one or more catalyst beds 104 can be from about 400° C. to about 950° C.; from about 500° C. to about 900° C.; from about 500° C. to about 850° C.; from about 500° C. to about 800° C.; or from about 500° C. to about 750° C. In at least some embodiments, the methane source 106, oxidant 108, or both the methane source 106 and the oxidant 108 may be halted or interrupted to the one or more vessels 102 when the one or more vessels are operated under substantially adiabatic conditions and the maximum temperature within the one or more catalyst beds is greater than about 700° C.; greater than about 750° C.; greater than about 800° C.; greater than about 850° C.; greater than about 900° C.; greater than about 950° C.; greater than about 1000° C.; greater than about 1050° C.; or greater than about 1100° C.

Additionally, when the one or more catalyst beds 104 are operated under substantially adiabatic conditions, the rate of temperature increase at any point within the one or more catalyst beds 104 can be controlled using by adjusting the temperature of the methane source 106, the oxidant 108, or both the methane source 106 and the oxidant 108. Such control provides the ability to limit the rate of temperature increase at any point within the one or more catalyst beds 104. Under substantially adiabatic conditions, the rate of temperature change at any point within the one or more catalyst beds 104 can be less than about 50° C./min; less than about 40° C./min; less than about 30° C./min; less than about 25° C./min; less than about 20° C./min; less than about 15° C./min; less than about 10° C./min; less than about 5° C./min; less than about 1° C./min. In at least some embodiments, the methane source 106, oxidant 108, or both the methane source 106 and the oxidant 108 may be halted or interrupted to the one or more vessels 102 when the one or more vessels are operated under substantially adiabatic conditions and the maximum rate of temperature increase at any point within the one or more catalyst beds is greater than about 5° C./min; greater than about 10° C./min; greater than about 15° C./min; greater than about 20° C./min; greater than about 25° C./min; greater than about 30° C./min; greater than about 40° C./min; or greater than about 50° C./min.

Where the one or more vessels 102 are operated under substantially adiabatic conditions as depicted in FIG. 1, the thermal energy released by the OCM reaction occurring within the catalyst will substantially only be removed with the OCM gas 110. Upon removal from the one or more vessels 102, at least a portion of the thermal energy carried by the OCM gas 110 can be removed using one or more thermal transfer devices 112. At least a portion of the one or more thermal transfer devices 112 can include one or more coolant injection points, for example one or more points where a cooled, or even liquefied gas such as nitrogen, oxygen, methane, or combinations thereof are introduced. At least a portion of the one or more thermal transfer devices 112 can include one or more non-contact heat transfer devices such as a heat exchanger or air cooler. The temperature of the OCM gas 110 after removal from the one or more thermal transfer devices 112 can vary based upon the use of the OCM gas 110. For example, where the OCM gas 110 removed from the one or more thermal transfer devices 112 will be used to provide all or a portion of the methane source 106 to a subsequent one or more vessels 102, the temperature of the OCM gas removed from the one or more vessels 102 may be no less than about 100° C.; no less than about 200° C.; no less than about 300° C.; no less than about 400° C.; no less than about 500° C.; no less than about 600° C.; no less than about 700° C.; no less than about 800° C.; or no less than about 900° C. Where the OCM gas 110 removed from the one or more thermal transfer devices 112 will be introduced to subsequent separation or distillation processes to remove or recover one or more components, the temperature of the OCM gas removed from the one or more vessels 102 may be no more than about 400° C.; no more than about 350° C.; no more than about 300° C.; no more than about 250° C.; no more than about 200° C.; no more than about 150° C.; no more than about 100° C.; or no more than about 50° C.

Operating under substantially adiabatic conditions, temperature increase across each catalyst bed 104, the outlet temperature of each catalyst bed 104, and the temperature profile of each catalyst bed 104 may be controlled based upon the temperature, pressure, flow, and composition of the methane source 106, the oxidant 108, and the bulk gas mixture 114. Each catalyst bed 104 inlet, outlet, and intermediate temperatures may be measured via one or more temperature sensors and transmitters (not shown in FIG. 1). All or a portion of the measured catalyst bed 104 temperature data may be used to provide one or more process input signals indicative of the measured catalyst temperature(s) to one or more temperature, pressure, flow, or composition controllers. The one or more controllers can provide a control signal output to one or more final control elements used to control the temperature, pressure, or flow of at least one of the methane source 106 or the oxidant 108. For example, responsive to some or all of the catalyst bed 104 inlet temperature, the catalyst bed 104 outlet temperature, the catalyst bed 104 maximum temperature, the catalyst bed 104 temperature gradient, or the catalyst bed 104 temperature profile, one or more of the temperature, pressure, flow, or composition of the methane source 106 or oxidant 108 may be controlled or otherwise adjusted using one or more control valves or the like.

In at least some situations, the longer chain saturated hydrocarbons produced in the OCM reaction can be subjected to one or more steam or thermal cracking operations using residual methane and nitrogen present in the OCM gas 110 as diluents to desaturate at least a portion of the saturated hydrocarbons, thereby increasing the concentration of one or more targeted unsaturated hydrocarbons such as ethylene, propylene, butene, and the like. In at least some situations, the steam or thermal cracking operation on the OCM gas 110 may occur prior to the removal of the OCM gas 110 from the at least one vessel 102, for example by introducing high pressure steam to at least a portion of the at least one vessel 102. In other instances, the OCM gas 110 removed from the at least one vessel 102 may be introduced to a separate chamber within the at least one vessel 102 or to a separate vessel 102 in which higher hydrocarbon cracking may occur.

In at least some embodiments, one or more higher hydrocarbons, for instance recovered ethane or $C_1$-$C_4$ light ends captured in an ethylene to liquids separations process, may be introduced to the OCM reactor 102, before the OCM reactor 102 (e.g., by mixing with the methane source 106), or after the OCM reactor 102 (e.g., by mixing with the OCM gas 110). In at least some embodiments, at least a portion of the one or more higher hydrocarbons may be introduced directly within the catalyst bed 104. In other embodiments, at least a portion of the one or more higher hydrocarbons may be introduced to the OCM gas 110 prior to cooling the OCM gas in a thermal transfer device 112 fluidly coupled to the OCM reactor 110.

The thermal transfer device 112 may provide all or a portion of the quench to halt the steam or thermal cracking of the OCM gas 110. Where more than one vessel 102 is used, for example where a plurality of serially coupled vessels 102 are used, steam or thermal cracking may be used in some or all of the vessels, for example in the last one, two or three serially coupled vessels 102. In some instances, the OCM gas 110 removed from the at least one vessel 102 may be introduced to a subsequent vessel dedicated to steam or thermal cracking of the OCM gas 110. The ability to thermally crack at least a portion of the OCM gas 110 prior to removal from the at least one vessel can advantageously convert a portion of the saturated hydrocarbons present in the OCM gas 110 to one or more targeted unsaturated hydrocarbons.

The OCM reaction processes and systems described herein provide the advantageous ability to operate an OCM process, at low reaction temperatures (e.g., less than 800° C.), low operating pressures (e.g., less than 120 psig), using air as an oxidant while maintaining a high GHSV (e.g., greater than 50,000 hr$^{-1}$). In one example, the OCM process using air to provide the oxidant 108 may provide ethylene and ethane yields in excess of 2% each while maintaining an adiabatic bed temperature of less than 750° C., a reaction pressure of less than 100 psig, and a GHSV in excess of 100,000 hr$^{-1}$.

Figure 2:
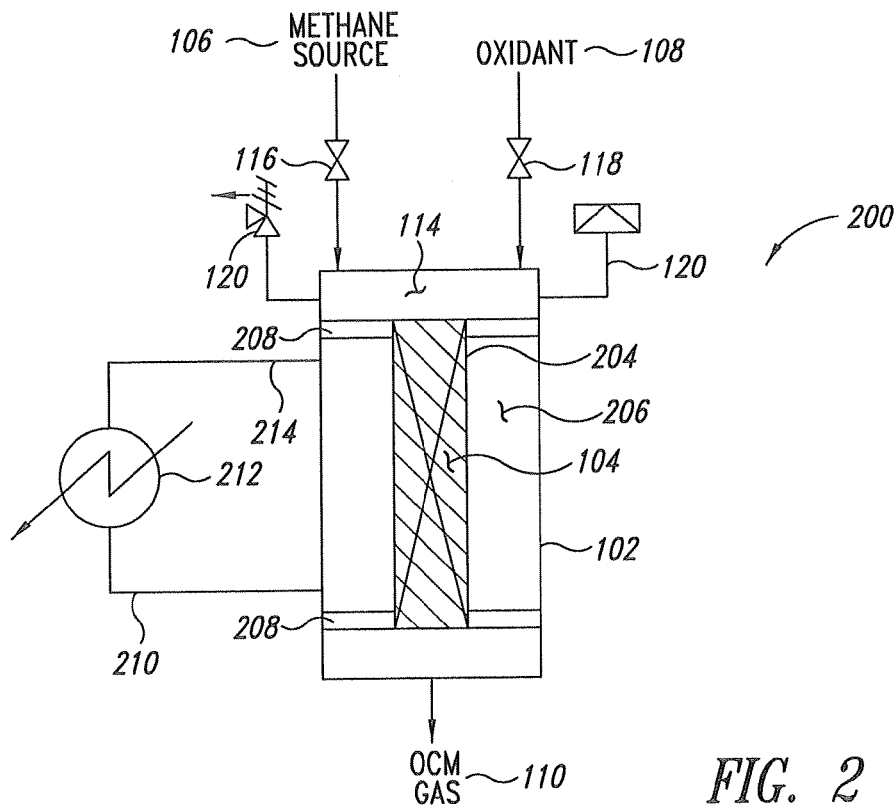
FIG. 2 shows a sectional view of an illustrative vessel for the isothermal, exothermic, reaction of a methane source and an oxidant over at least one catalyst to provide an oxidative coupling of methane ("OCM") gas.

FIG. 2 shows schematically a system 200 for the production of one or more alkene hydrocarbons via oxidative coupling of methane ("OCM") in the presence of at least one catalyst. The system 200 includes at least one vessel 102 containing one or more catalysts forming at least one catalyst bed 104. Within the at least one vessel 102, the at least one catalyst bed 104 is at least partially disposed within an interior space formed within one or more hollow members 204 such as one or more cylindrical heat exchanger tubes. Methane present in the methane source 106 and oxygen present in the oxidant 108 exothermically react as they pass through the one or more catalysts forming the at least one catalyst bed 104 in each of the one or more hollow members 204. In at least some embodiments, a plurality of hollow members 204, each containing one or more catalysts forming one or more catalyst beds 104 can extend across substantially all the cross sectional area of the at least one vessel 102, thereby minimizing or eliminating the possibility of gas bypass around the at least one catalyst bed 104. In at least some embodiments, the at least one vessel 102 may physically resemble a vertically oriented shell and tube heat exchanger having one or more hollow members 204 configured to form a plurality of equivalent, parallel, flow paths arranged on a triangular or square tube pitch. A tubesheet 208 may be affixed to each end of the one or more hollow members to fluidly isolate the bulk gas mixture 114 and the OCM gas 110 from a void 206 through which a coolant may flow about the one or more hollow members 204.

The void 206 extends from an exterior surface defined by the one or more hollow members 204 to an interior surface of the one or more vessels 102. In at least some embodiments, a coolant is circulated through the void 206 to transfer thermal energy released by the exothermic OCM reaction occurring within the at least one catalyst forming the one or more catalyst beds 104 within the one or more hollow members 204. In some instances, the void 206 can include one or more sections, each containing the same or a different coolant at the same or different temperatures to provide a plurality of operating temperature ranges throughout the length of the one or more hollow members 204. One or more external thermal transfer devices 212 is fluidly coupled 210, 214 to the void 206 and used to remove thermal energy from the coolant prior to reintroducing the coolant back into the void 206. The use of one or more external thermal transfer devices 212 to remove at least a portion of the thermal energy released by the OCM reaction occurring within the one or more catalyst beds 104 disposed within the one or more hollow members 204, permits the operation of the one or more catalyst beds 104 under substantially isothermal conditions.

When the one or more catalyst beds 104 are operated under substantially isothermal conditions, the temperature increase across the one or more catalyst beds 104 can be limited or controlled by adjusting at least one of the flowrate or temperature of the coolant within the void 206. The temperature increase across the one or more catalyst beds 104 may also be limited or otherwise controlled by adjusting one or more of the temperature, pressure, flow, or composition of the methane source 106, the oxidant 108, or the bulk gas mixture 114. Such control provides the ability to limit the temperature increase through the one or more catalyst beds 104. Under substantially isothermal conditions, the temperature increase or axial temperature gradient across the one or more catalyst beds 104 (e.g. measured from tube entry to tube exit, or the difference between inlet temperature and outlet temperature) can be less than about 50° C.; less than about 40° C.; less than about 30° C.; less than about 25° C.; less than about 20° C.; less than about 15° C.; less than about 10° C.; less than about 5° C.; or less than about 1° C.

Under substantially isothermal conditions, a temperature profile may develop radially outward from the center of the tube—in other words, the temperature of the catalyst bed measured at the center of the hollow member 204 may be greater than the temperature measured proximate the interior wall of the hollow member 204 where thermal energy is exchanged with the coolant in the void 206. This differential temperature across the diameter of the hollow member may be referred to as a "radial temperature gradient." The radial temperature gradient may be linearly dependent or non-linearly dependent (e.g., exponential, hyperbolic, parabolic, etc.) upon the distance from the center of the hollow member 204. In at least some embodiments the temperature difference between the catalyst at the center of the hollow member and the catalyst proximate the hollow member wall can be less than about 500° C.; less than about 450° C.; less than about 400° C.; less than about 350° C.; less than about 300° C.; less than about 250° C.; less than about 200° C.; less than about 150° C.; less than about 100° C.; less than about 50° C.; less than about 25° C.; less than about 10° C.; or less than about 5° C.

Operationally, the radial temperature gradient within a vessel 102 operated under substantially isothermal conditions can be greater, and in some instances significantly greater, than the axial temperature gradient within the hollow member 204. In some instances, the radial temperature gradient (temperature difference between catalyst in center and proximate the wall of the hollow member 204) and the axial temperature gradient (catalyst temperature difference between tube inlet and tube exit) can be greater than about 10° C.; greater than about 25° C.; greater than about 50° C.; greater than about 100° C.; greater than about 150° C.; greater than about 200° C.; or greater than about 250° C.

In at least some embodiments, the methane source 106, oxidant 108, or both the methane source 106 and the oxidant 108 may be halted or interrupted to the one or more vessels 102 when the one or more vessels are operated under substantially isothermal conditions and the temperature increase across or through the one or more catalyst beds is greater than about 5° C.; greater than about 10° C.; greater than about 15° C.; greater than about 20° C.; greater than about 25° C.; greater than about 30° C.; greater than about 45° C.; greater than about 60° C.; or greater than about 75° C.

When the one or more catalyst beds 104 are operated under substantially isothermal conditions, the maximum temperature attained within the one or more catalyst beds 104 can be controlled by adjusting at least one of the flowrate or temperature of the coolant within the void 206. The maximum temperature attained within the one or more catalyst beds 104 may also be limited or otherwise controlled by adjusting one or more of the temperature, pressure, flow, or composition of the methane source 106, the oxidant 108, or the bulk gas mixture 114. Such control provides the ability to limit the maximum temperature attained within the one or more catalyst beds 104. Under substantially isothermal conditions, the maximum temperature within the one or more catalyst beds 104 can be less than about 1000° C.; less than about 950° C.; less than about 900° C.; less than about 850° C.; less than about 800° C.; less than about 750° C.; less than about 700° C.; less than about 650° C.; or less than about 600° C. Under substantially isothermal conditions, the operating temperature within the one or more catalyst beds 104 can be from about 400° C. to about 950° C.; from about 500° C. to about 900° C.; from about 500° C. to about 850° C.; from about 500° C. to about 800° C.; or from about 500° C. to about 750° C. In at least some embodiments, the methane source 106, oxidant 108, or both the methane source 106 and the oxidant 108 may be halted or interrupted to the one or more vessels 102 when the one or more vessels are operated under substantially isothermal conditions and the maximum temperature within the one or more catalyst beds is greater than about 650° C.; greater than about 700° C.; greater than about 750° C.; greater than about 800° C.; greater than about 850° C.; greater than about 900° C.; greater than about 950° C.; greater than about 1000° C.; or greater than about 1050° C.

Additionally, when the one or more catalyst beds 104 are operated under substantially isothermal conditions, the rate of temperature change at any point within the one or more catalyst beds 104 can be controlled by adjusting at least one of the flowrate or temperature of the coolant within the void 206. Such control provides the ability to limit the rate of temperature change at any point within the one or more catalyst beds 104. Under substantially isothermal conditions, the rate of temperature change at any point within the one or more catalyst beds 104 can be less than about 50° C./min; less than about 40° C./min; less than about 30° C./min; less than about 25° C./min; less than about 20° C./min; less than about 15° C./min; less than about 10° C./min; less than about 5° C./min; less than about 1° C./min. In at least some embodiments, the methane source 106, oxidant 108, or both the methane source 106 and the oxidant 108 may be halted or interrupted to the one or more vessels 102 when the one or more vessels are operated under substantially isothermal conditions and the maximum rate of temperature change at any point within the one or more catalyst beds is greater than about 5° C./min; greater than about 10° C./min; greater than about 15° C./min; greater than about 20° C./min; greater than about 25° C./min; greater than about 30° C./min; greater than about 40° C./min; or greater than about 50° C./min.

Operating under substantially isothermal conditions within each of the hollow members 204 containing a catalyst bed 104, the temperature increase or gradient across the catalyst bed 104, the outlet temperature of the catalyst bed 104, and the temperature profile of the catalyst bed 104 may be partially or completely controlled by adjusting at least one of the temperature, pressure, flow, and composition of the methane source 106 or the oxidant 108. Additionally within each of the hollow members 204 containing a catalyst bed 104, the temperature increase or gradient across the catalyst bed 104, the outlet temperature of the catalyst bed 104, and the temperature profile of the catalyst bed 104 may also be partially or completely controlled by adjusting at least one of the temperature or the flowrate of the coolant flowing through the void 206. The temperature of the coolant within the void 206 may be controlled, for example through the use of one or more temperature controllers and coupled to one or more final control elements configured to increase or decrease the amount of thermal energy removed from the coolant using the one or more thermal transfer devices 212.

The inlet, outlet, and intermediate temperatures for each catalyst bed 104 are measured using one or more temperature sensors and transmitters (not shown in FIG. 2). In at least some situations, all or a portion of the measured catalyst bed 104 temperature data may be used to provide one or more process variable inputs to one or more temperature, pressure, flow, or composition controllers coupled to final control elements acting on the methane source 106 or the oxidant 108. In those situations, responsive to some or all of the catalyst bed 104 inlet temperature, the catalyst bed 104 outlet temperature, the catalyst bed 104 maximum temperature, the catalyst bed 104 temperature gradient or increase, or the catalyst bed 104 temperature profile, one or more of the temperature, pressure, flow, or composition of the methane source 106 or oxidant 108 may be adjusted using one or more final control elements such as one or more control valves or the like.

In at least some situations, all or a portion of the measured catalyst bed 104 temperature data may be used to provide one or more process variable inputs to one or more temperature or flow controllers coupled to final control elements acting on the coolant within the void 206. In those situations, responsive to some or all of the catalyst bed 104 inlet temperature, the catalyst bed 104 outlet temperature, the catalyst bed 104 maximum temperature, the catalyst bed 104 temperature gradient or increase, or the catalyst bed 104 temperature profile, one or more of the level, temperature or flow of the coolant through the void 206 may be adjusted using one or more final control elements such as one or more control valves or the like. In at least some instances, the coolant level within the void 206 may be adjusted during start-up and operation of the at least one vessel. For example during start-up the level of the coolant may be maintained at a low level to permit heat to build within the catalyst bed 104, promoting the formation of one or more targeted hydrocarbons. As the temperature builds within the catalyst bed 104, the coolant level within the void 206 can be adjusted to maintain a desired temperature or temperature profile within the catalyst bed 104.

The one or more hollow members 204 can include a hollow member having any cross-sectional profile. An example hollow member 204 includes an electric resistance welded ("ERW") or seamless drawn carbon steel alloy, stainless steel alloy, or nickel alloy tube having a diameter of less than about 0.375 inches; less than about 0.5 inches; less than about 0.625 inches; less than about 0.75 inches; less than about 0.875 inches; less than about 1 inch; less than about 1.25 inches; less than about 1.5 inches; or less than about 2 inches. An example hollow member 204 includes an electric resistance welded ("ERW") or seamless drawn carbon steel alloy, stainless steel alloy, or nickel alloy tube having a wall thickness of less than about 0.2 inches; less than about 0.1 inches; less than about 0.075 inches; less than about 0.05 inches; or less than about 0.025 inches. The one or more hollow members 204 can have any length, including lengths of less than about 20 feet; less than about 15 feet; less than about 10 feet; less than about 8 feet; less than about 6 feet; less than about 4 feet; less than about 3 feet; less than about 2 feet; less than about 1.5 feet; less than about 1 foot; less than about 0.5 feet; or less than about 0.1 feet.

Each of the one or more hollow members 204 can contain a catalyst bed 104 including one or more catalysts, one or more inert materials, or any combination thereof. In at least some embodiments, the catalyst bed 104 within each of the hollow members 104 may include a plurality of distinct layers, zones, or sections. In at least some embodiments, the one or more catalysts 104 disposed within each of the one or more hollow members 204 can include one or more inert materials used as a support for the one or more catalysts within each of the hollow members 204. The one or more catalysts can include one or more different composition catalysts, one or more active catalyst concentrations, one or more inerts, or combinations thereof. In at least some embodiments one or more screens, grids, or support structures may be disposed proximate one or both ends of the one or more hollow members 204 to maintain the one or more catalysts within the hollow member 204. The GHSV through each of the one or more hollow members 204 may be the same or different since changes in either the reactant gas flow rate or the volume of each of the one or more hollow members 204 will affect the GHSV. The GHSV in each of the one or more hollow members 204 can be less than about 100,000 $h^{-1}$; less than about 75,000 $h^{-1}$; less than about 50,000 $h^{-1}$; less than about 40,000 $h^{-1}$; less than about 30,000 $h^{-1}$; less than about 20,000 $h^{-1}$; less than about 10,000 $h^{-1}$; less than about 5,000 $h^{-1}$; less than about 4,000 $h^{-1}$; less than about 2,000 $h^{-1}$; or less than about 1,000 $h^{-1}$.

The temperature gradient or rise rate within the catalyst bed 104 is a function of the linear velocity, temperature, pressure, and composition of the bulk gas mixture 114 as well as the composition of the catalyst bed 104. The temperature gradient or rise rate within the catalyst bed 104 is also a function of the linear velocity of the bulk gas mixture 114 through the catalyst bed 104. The linear velocity of the bulk gas mixture 114 through the catalyst bed 104 can be less than about 50 meters/sec (m/s); less than about 25 m/s; less than about 20 m/s; less than about 15 m/s; less than about 10 m/s; less than about 5 m/s; less than about 2.5 m/s; less than about 1 m/s; less than about 0.5 m/s; less than about 0.1 m/s.

The one or more hollow members 204 can be physically bonded to and affixed within one or more tubesheets 208 that form a portion of the void 206 to prevent loss of the coolant from the void 206. Where multiple hollow members 204 are used, for example where the vessel 102 includes a shell and tube type heat exchanger, one or more intermediate tube stays or baffles (not shown in FIG. 2, but well known to those in the chemical engineering art) may be affixed periodically along the lengths of a portion of the one or more hollow members 204 to maintain spacing between the one or more hollow members 204, to permit the flow of coolant between the one or more hollow members 204, and to promote an even distribution and flow pattern of the coolant within the void 206.

The void 206 can be partially or completely filled with one or more coolants. The one or more coolants can be selected based upon maximum operating temperature, heat transport capability, stability, flowability, corrosivity or combinations thereof. The coolant can flow through the thermal transfer device 212 via pumping, closed-loop thermosyphoning or combinations thereof. The one or more coolants can include, but are not limited to one or more molten metal or salt coolants, one or more liquid coolants, one or more gaseous coolants, or combinations thereof. In some embodiments, the one or more coolants can include one or more fusible alloys such as sodium, sodium-potassium alloys, lead, or lead bismuth alloys. In one or more preferred embodiments, the one or more coolants include one or more molten salts including a mixture of sodium fluoride and sodium tetrafluoroborate ($NaF$—$NaBF_4$), lithium fluoride and beryllium fluoride (FLiBe), or lithium fluoride, sodium fluoride, and potassium fluoride (FLiNaK). In at least some embodiments, one or more mineral or thermal transfer oils can be used as a coolant within the void 206. Other similar coolants, including but not limited to solar salts such as $NaNO_2$, $NaNO_3$, and $KNO_3$, may be substituted.

Relatively high temperature coolant can be removed from the void 206 and introduced to the one or more thermal transfer devices 212 via one or more connections 214 that fluidly couple the one or more thermal transfer devices 212 to the void 206. The relatively high temperature coolant passes through the one or more thermal transfer devices 212 and is returned as a relatively low temperature coolant to the void 206 via one or more connections 210 that fluidly couple the one or more thermal transfer devices 212 to the void 206. In at least some embodiments, one or more coolant storage systems (not shown in FIG. 2) may be fluidly coupled to the void 206 to accept and maintain the coolant at or above the liquification temperature of the coolant, for example when the coolant is removed or otherwise isolated from the one or more vessels 102 or one or more thermal transfer devices 212 to permit maintenance or repair of the one or more vessels 102 or one or more thermal transfer devices 212.

At least a portion of the thermal energy removed from the void 206 by the coolant may be removed from the coolant via the one or more thermal transfer devices 212. The one or more thermal transfer devices 212 can include one or more non-contact heat transfer devices such as a heat exchanger to transfer thermal energy from the coolant to one or more thermal fluids, or air cooler to transfer thermal energy from the coolant to air passing through the air cooler. In at least some embodiments, the one or more thermal transfer devices 212 can include heat transfer surfaces having one or more enhanced heat transfer surfaces such as fins or flutes.

The temperature of the coolant exiting the one or more thermal transfer devices 212 can vary based upon the thermal transfer medium used to remove thermal energy from the coolant, the freezing point of the coolant, the desired temperature of the one or more catalyst beds, or combinations thereof. For example, where the temperature of the OCM gas 110 removed from the one or more thermal transfer devices 112 will be used to provide all or a portion of the methane source 106 to a one or more subsequent vessels 102, the temperature of the OCM gas removed from the one or more vessels 102 may be greater than about 100° C.; greater than about 200° C.; greater than about 300° C.; greater than about 400° C.; greater than about 500° C.; greater than about 600° C.; greater than about 700° C.; greater than about 800° C.; or greater than about 900° C. Where the OCM gas 110 removed from the one or more thermal transfer devices 112 will be introduced to subsequent separation or distillation processes to remove or recover one or more components, the temperature of the OCM gas removed from the one or more vessels 102 may be less than about 400° C.; less than about 350° C.; less than about 300° C.; less than about 250° C.; less than about 200° C.; less than about 150° C.; less than about 100° C.; or less than about 50° C.

Figure 3:
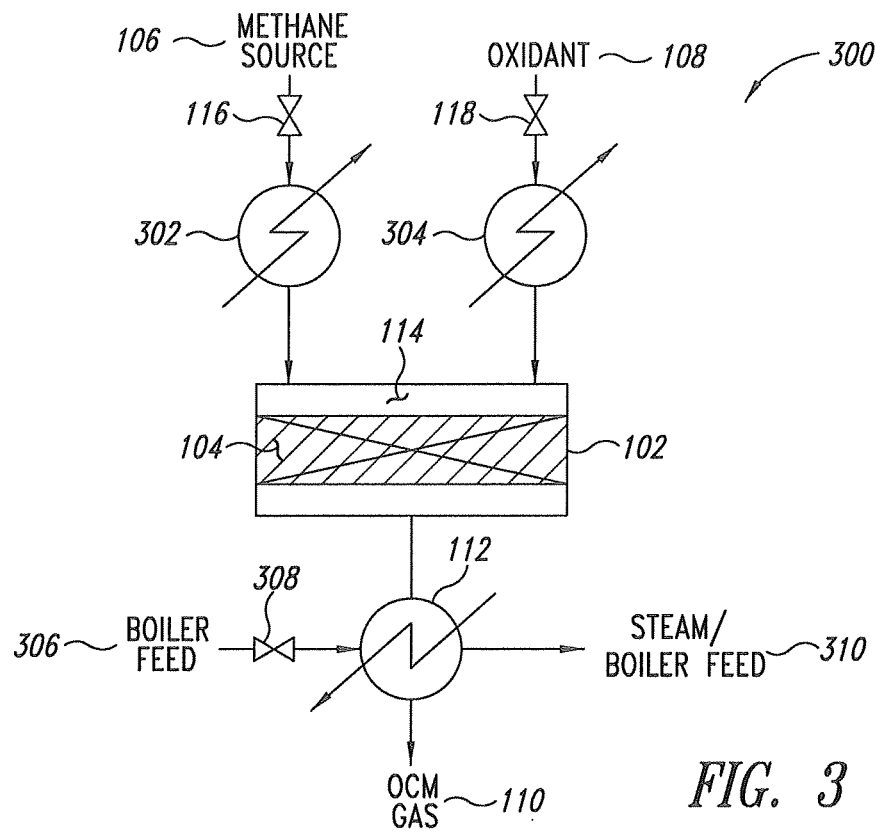
FIG. 3 shows a sectional view of an illustrative vessel for the adiabatic exothermic reaction of a methane source and an oxidant over at least one catalyst to provide an oxidative coupling of methane ("OCM") gas including preheating of the methane source and oxidant.

FIG. 3 shows schematically a system 300 for the production of one or more alkene hydrocarbons via oxidative coupling of methane ("OCM") using one or more vessels 102 having one or more catalyst beds 104 operating under adiabatic conditions. The system 300 further includes one or more thermal input devices 302 for providing a thermal energy input to the methane source 106, one or more thermal input devices 304 for providing a thermal energy input to the oxidant 108.

When operated under substantially adiabatic conditions, the thermal energy released by the OCM reaction occurring in the one or more catalyst beds 104 is removed from the one or more vessels 102 substantially only via the OCM gas 110 removed from the one or more vessels 102. In at least some circumstances, the OCM reaction occurring in the one or more catalyst beds 104 can be adjusted, affected, or otherwise controlled by adjusting the thermal energy content of the methane source 106, the thermal energy content of the oxidant 108, or the thermal energy content of the bulk gas mixture 114. For example, reducing the thermal energy content of the methane source 106, the oxidant 108, or the bulk gas mixture 114 can result in a lower temperature within the one or more catalyst beds 104. Reducing the temperature within the one or more catalyst beds 104 can affect the composition of the resultant OCM gas 110.

In at least some embodiments, a thermal energy input can be provided to the methane source 106 via one or more thermal input devices 302. The one or more thermal input devices 302 can include, but are not limited to, one or more non-contact combustion heaters, one or more non-contact heat transfer devices such as a shell-and-tube, or plate-and-frame heat exchanger making use of a heat transfer fluid having available thermal energy, or combinations thereof.

The one or more thermal input devices 302 can include a non-contact combustion heater to provide a thermal energy input to the methane source 106. The non-contact combustion heater can use any fuel source to provide the thermal energy input including methane, natural gas, one or more refined petroleum products or the like. The amount of thermal energy input provided by the combustion heater to the methane source can, in some instances, be adjusted by automatically or manually controlling the flow of fuel to the combustion heater. In some instances, the amount of thermal energy input provided by the combustion heater to the methane source 106 can be adjusted by automatically or manually bypassing all or a portion of the methane source 106 around the combustion heater.

The one or more thermal input devices 302 can include one or more non-contact heat transfer devices to provide a thermal energy input to the methane source 106. The one or more non-contact heat transfer devices can use any heat transfer fluid having available thermal energy, for example saturated or superheated steam, or one or more process streams, such as the OCM product gas 110, at an elevated temperature to provide the thermal energy input to the methane source 106. The amount of thermal energy input provided by the one or more non-contact heat transfer devices to the methane source can, in some instances, be adjusted by automatically or manually controlling the flow of the heat transfer fluid having available thermal energy through the one or more non-contact heat transfer devices. In some instances, the amount of thermal energy input provided by the one or more non-contact heat transfer devices to the methane source 106 can be adjusted by automatically or manually bypassing all or a portion of the methane source 106 around the one or more non-contact heat transfer devices.

In at least some embodiments, a thermal energy input can be provided to the oxidant 108 via one or more thermal input devices 304. The one or more thermal input devices 304 can include, but are not limited to, one or more non-contact combustion heaters, one or more non-contact heat transfer devices such as a shell-and-tube, or plate-and-frame heat exchanger making use of a heat transfer fluid having available thermal energy, or any combination thereof.

The one or more thermal input devices 304 can include a non-contact combustion heater to provide a thermal energy input to the oxidant 108. The non-contact combustion heater can use any fuel source to provide the thermal energy input including methane, natural gas, one or more refined petroleum products or the like. The amount of thermal energy input provided by the combustion heater to the oxidant 108 may, in some instances, be adjusted by automatically or manually controlling the flow of fuel to the combustion heater. In some instances, the amount of thermal energy input provided by the combustion heater to the oxidant 108 may be adjusted by automatically or manually bypassing all or a portion of the oxidant 108 around the combustion heater.

The one or more thermal input devices 304 can include one or more non-contact heat transfer devices to provide a thermal energy input to the oxidant 108. The one or more non-contact heat transfer devices can use any heat transfer fluid having available thermal energy, for example saturated or superheated steam, or one or more process streams, such as the OCM gas 110, at an elevated temperature to provide the thermal energy input to the oxidant 108. The amount of thermal energy input provided by the one or more non-contact heat transfer devices to the oxidant 108 can, in some instances, be adjusted by automatically or manually controlling the flow of the heat transfer fluid having available thermal energy through the one or more non-contact heat transfer devices. In some instances, the amount of thermal energy input provided by the one or more non-contact heat transfer devices to the oxidant 108 can be adjusted by automatically or manually bypassing all or a portion of the oxidant 108 around the one or more non-contact heat transfer devices.

Thermal energy can be removed from the OCM gas 110 using one or more thermal transfer devices 112. In at least some embodiments, boiler feed water 306 can provide all or a portion of the heat transfer fluid used to remove thermal energy from the OCM gas 110. In at least some situations, the one or more thermal transfer devices 112 can be a heat exchanger used in conjunction with one or more final control elements 308 controlling the flow of boiler feed water 306 through the one or more thermal transfer devices 112 such that the temperature of the boiler feed water 306 is increased to a point just below boiling to provide a heated boiler feed water 310. In at least some situations, the one or more thermal transfer devices 112 can be a fire tube boiler used in conjunction with one or more final control elements 308 controlling the flow of boiler feed water 306 to the one or more thermal transfer devices 112 to vaporize at least a portion of the boiler feed water 306 and to provide a saturated or superheated steam 310. In at least some situations, the saturated steam 310 produced by the one or more thermal transfer devices 112 is saturated at a pressure of less than about 2000 psig; less than about 1500 psig; less than about 900 psig; less than about 600 psig; less than about 300 psig; less than about 150 psig; less than about 75 psig; or less than about 50 psig.

In some instances, the temperature of the OCM gas 110 may be adjusted or otherwise controlled by preventing at least a portion of the OCM gas 110 from passing through the one or more thermal transfer devices 112. Preventing the passage of at least a portion of the OCM gas 110 removed from the at least one vessel 102 from passing through the one or more thermal transfer devices 112 can be accomplished, for example, by bypassing at least a portion of the OCM gas 110 around the one or more thermal transfer devices 112 using a bypass that is either internal to or external from the one or more thermal transfer devices 112.

In at least some instances, at least a portion of the thermal energy removed from the OCM gas 110 may be introduced to at least one of either the methane source 106 or the oxidant 108. The transfer of thermal energy may be direct, for example by passing at least a portion of the OCM gas 110 and at least a portion of at least one of either the methane source 106 or the oxidant 108 through a non-contact thermal transfer device. In other instances, the transfer of thermal energy may be indirect, for example as shown in FIG. 3 where thermal energy removed from the OCM gas 110 is used to produce steam which can then be used to transfer thermal energy to at least one of either the methane source 106 or the oxidant 108.

Operating under substantially adiabatic conditions and for a given catalyst bed composition, temperature increase or gradient across each catalyst bed 104, the outlet temperature of each catalyst bed 104, and the temperature profile of each catalyst bed 104 may be controlled based upon the temperature, pressure, flow, and composition of the methane source 106, the oxidant 108, and the bulk gas mixture 114. The catalyst bed 104 inlet, outlet, and intermediate temperatures can be measured using one or more temperature sensors and transmitters (not shown in FIG. 3). All or a portion of the measured catalyst bed 104 temperature data may be used to provide one or more process variable inputs to one or more temperature, pressure, flow, or composition controllers coupled to final control elements capable of directly or indirectly acting on at least one of either the methane source 106 or the oxidant 108. For example, responsive to at least one of the measured catalyst bed 104 inlet temperature, outlet temperature, maximum temperature, temperature gradient or increase, or temperature profile, one or more of the temperature, pressure, flow, or composition of the methane source 106 or oxidant 108 may be adjusted using one or more final control elements such as one or more control valves or the like.

As depicted in FIG. 3, at least a portion of the thermal energy contained in the OCM gas 110 may be removed using boiler feed water 306 which, upon receipt of the thermal energy from the OCM gas, can provide heated boiler feed water or steam 310. In at least some instances, the temperature of the OCM gas can be measured using one or more temperature sensors and transmitters providing a process variable input to one or more flow controllers providing a control output to one or more final control elements such as a flow control valve configured to control the flow of boiler feed water through the one or more thermal transfer devices 112.

Figure 4:
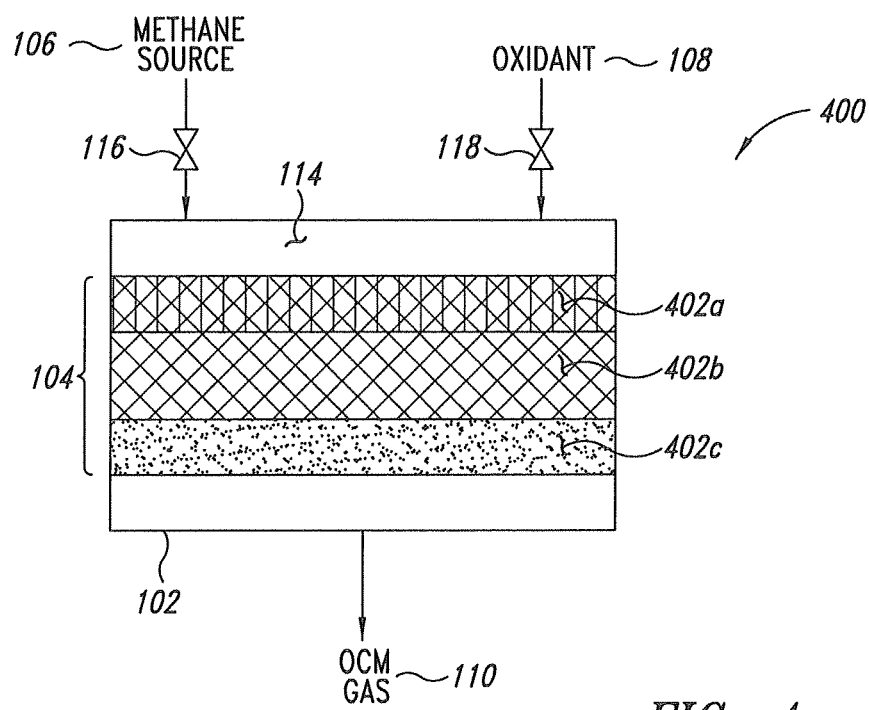
FIG. 4 shows a sectional view of an illustrative vessel containing multiple catalyst beds for the adiabatic, exothermic, reaction of a methane source and an oxidant over at least one catalyst to provide an oxidative coupling of methane ("OCM") gas.

FIG. 4 shows schematically a system 400 for the production of one or more alkene hydrocarbons via oxidative coupling of methane ("OCM") using one or more vessels 102 having a single, three-layer, catalyst bed 104 operating under adiabatic conditions. For illustrative purposes and for clarity and conciseness, a single vessel 102 having a single, three layer, catalyst bed 104 will be discussed in detail, however one of ordinary skill in the art will readily appreciate that any number of beds 104 having any number of layers may be similarly disposed in any number of vessels 102.

In some instances, each of the one or more catalyst beds 104 may contain multiple layers, for example three layers 402a, 402b, and 402c (collectively "layers 402") as shown in FIG. 4. Each of the layers 402 forming the catalyst bed 104 may contain one or more catalysts, one or more inert materials, or combinations thereof. The individual catalysts or inerts selected for inclusion in each of the layers 402 may be selected for one or more properties or characteristics that include, but are not limited to, catalyst activity, catalyst end product selectivity, catalyst or inert gas phase pressure drop, catalyst or inert effect on thermal profile through the individual layer or through the entire bed, or combinations thereof.

Each of the layers 402 may be homogeneous, containing a catalyst having a single chemical composition, a catalyst having a single physical configuration, an inert having a single chemical composition, or an inert having a single physical configuration. Alternatively, all or a portion of the layers 402 may be heterogeneous, containing two or more catalysts having differing chemical compositions or physical configurations, or containing two or more inert materials having differing chemical compositions or physical configurations.

For example, a first catalyst having a chemical composition "A" may be selectively doped with a dopant "B1" to provide a catalyst having a very high activity. A second catalyst, physically identical to the first catalyst, having chemical composition "A" may be selectively doped with a dopant "B2" to provide a catalyst having lower activity but greater selectivity in providing one or more desired products such as ethylene. Within example vessel 102 operating under adiabatic (i.e. no internal heat transfer) conditions, an example catalyst bed 104 may contain the following three layers: (a) layer 402a—a 12" layer containing the first catalyst disposed on a structured inert substrate, for example a ceramic honeycomb substrate; (b) layer 402b—a 12" layer containing a mixture of the first and the second catalysts also disposed on a structured inert substrate such as the ceramic honeycomb substrate; and (c) layer 402c—a 6" layer containing the second catalyst formed into physical shapes having low gas phase pressure drop characteristics such as rings or saddles, in a randomly poured layer.

As described above, the high activity of the first catalyst will generally result in a large quantity of thermal energy being released by the OCM reaction occurring proximate the catalyst. Placing the first layer 402a on a honeycomb substrate will permit limited dispersion of the thermal energy within the layer, serving to limit the overall heat buildup within layer 402a. The second layer, 402b, contains both the first catalyst and the second catalyst. The activity of the first catalyst will continue to release a significant quantity of thermal energy, hence the repeated use of the honeycomb substrate to assist in dispersing the thermal energy throughout the layer.

It may have been determined that the placement of the second catalyst in the second layer 402b advantageously resulted in a slight increase in the production of preferred products such as ethylene within the layer 402b. In fact, it may have been determined that the thermal energy released in layer 402a increased the production of ethylene in layer 402b. Thus, layer 402a may have been included in the catalyst bed 104 to provide a thermal profile favorable for the production of ethylene through at least the second layer 402b and perhaps throughout the entire catalyst bed 104.

The third layer 402c contains a random poured layer of the second catalyst. The lower activity of the second catalyst may limit the release of thermal energy within the third layer 402c, thereby permitting the use of a random poured catalyst without the risk of overheating the third layer 402c or the entire catalyst bed 104. The higher selectivity of the third layer 402c, particularly when combined with the relatively high exit temperature exiting the second layer 402b, may result in the third layer 402c acting as a "polishing" step, providing additional preferred products while not substantially increasing the exit temperature from the catalyst bed 104.

Catalysts may be combined or blended with one or more inert materials such as ceramics or other refractory type, chemically inert, materials to adjust or otherwise affect the activity or selectivity of the catalyst. Such blending or mixing can be used to adjust the thermal profile through or across of all or a portion of the one or more beds 104 within each of the one or more vessels 102. In some instances, a pure inert layer may be used within some or all of the catalyst beds 104 to provide a preferred thermal profile through or across the catalyst bed 104 or to maintain a desired maximum or minimum temperature rise across the catalyst bed 104.

In at least some instances, the catalyst bed 104 inlet temperature, the catalyst bed 104 outlet temperature, and one or more intermediate catalyst bed 104 temperatures may be measured using temperature sensors and transmitters to provide one or more signals indicative of the respective temperature. Operating under substantially adiabatic conditions, temperature increase or gradient across the catalyst bed 104 or each of the layers 402, the outlet temperature of each catalyst bed 104 or each of the layers 402, and the temperature profile of each catalyst bed 104 or each of the layers 402 may be controlled based upon the temperature, pressure, flow, and composition of the methane source 106, the oxidant 108, and the bulk gas mixture 114. The catalyst bed 104 or layer 402 inlet, outlet, and intermediate temperatures may be measured using one or more temperature sensors and transmitters (not shown in FIG. 4). All or a portion of the measured catalyst bed 104 or layer 402 temperature data may be used to provide one or more process variable inputs to one or more temperature, pressure, flow, or composition controllers coupled to final control elements capable of directly or indirectly acting on at least one of either the methane source 106 or the oxidant 108. For example, responsive to at least one of the measured catalyst bed 104 or layer 402 inlet temperature, outlet temperature, maximum temperature, temperature gradient or increase, or temperature profile, one or more of the temperature, pressure, flow, or composition of the methane source 106 or oxidant 108 may be adjusted using one or more final control elements such as one or more control valves or the like.

With layers 402 present, the catalyst bed 104 can be controlled or operated in a variety of manners. In some instances, a desired temperature rise or linear or non-linear temperature profile across one or more layers 402 within the catalyst bed 104 may be used to establish a target temperature or a target composition for the bulk gas mixture 114. In some instances, a desired linear or non-linear temperature rise rate (i.e., degrees of temperature per unit depth or length of catalyst) across one or more layers 402 within the catalyst bed 104 may be used to establish a target temperature or a target composition for the bulk gas mixture 114. In other instances, a desired linear or non-linear temperature profile across all three layers of the catalyst bed 104 may be used to establish a target temperature or a target composition for the bulk gas mixture 114.

In at least some embodiments, a target temperature or a target composition for the bulk gas mixture 114 can be based on maintaining a temperature rise across any one layer 402 of the catalyst bed 104 of less than about 200° C.; less than about 150° C.; less than about 100° C.; less than about 50° C.; less than about 40° C.; less than about 30° C.; less than about 20° C.; or less than about 10° C. In at least some embodiments, a target temperature or a target composition for the bulk gas mixture 114 can be based on maintaining a temperature rise across the catalyst bed 104 of less than about 300° C.; less than about 250° C.; less than about 225° C.; less than about 200° C.; less than about 175° C.; less than about 150° C.; less than about 125° C.; less than about 100° C.; less than about 75° C.; or less than about 50° C.

In at least some embodiments, a target temperature or a target composition for the bulk gas mixture 114 can be based on maintaining a maximum temperature rise rate across any one layer 402 of the catalyst bed 104 of less than about 50° C./cm; less than about 40° C./cm; less than about 30° C./cm; less than about 25° C./cm; less than about 20° C./cm; less than about 15° C./cm; less than about 10° C./cm; less than about 5° C./cm; less than about 1° C./cm; or less than about 0.5° C./cm. In at least some embodiments, a target temperature or a target composition for the bulk gas mixture 114 can be based on maintaining a maximum temperature rise rate across the catalyst bed 104 of less than about 50° C./cm; less than about 40° C./cm; less than about 30° C./cm; less than about 25° C./cm; less than about 20° C./cm; less than about 15° C./cm; less than about 10° C./cm; less than about 5° C./cm; less than about 1° C./cm; or less than about 0.5° C./cm.

In at least some embodiments, a target temperature or a target composition for the bulk gas mixture 114 can be based on maintaining a maximum temperature within any one layer 402 of the catalyst bed 104 of less than about 1000° C.; less than about 950° C.; less than about 900° C.; less than about 850° C.; less than about 800° C.; less than about 750° C.; less than about 700° C.; less than about 650° C.; or less than about 600° C. Under substantially adiabatic conditions, the operating temperature range within the catalyst bed 104 can be about 400° C. to about 950° C.; about 500° C. to about 900° C.; about 500° C. to about 850° C.; about 500°

C. to about 800° C.; or about 500° C. to about 750° C. In at least some embodiments, a target temperature or a target composition for the bulk gas mixture 114 can be based on maintaining a maximum temperature within the catalyst bed 104 of less than about 1100° C.; less than about 1050° C.; less than about 1000° C.; less than about 950° C.; less than about 900° C.; less than about 850° C.; less than about 800° C.; less than about 750° C.; less than about 700° C.; less than about 650° C.; or less than about 600° C.

Figure 5:
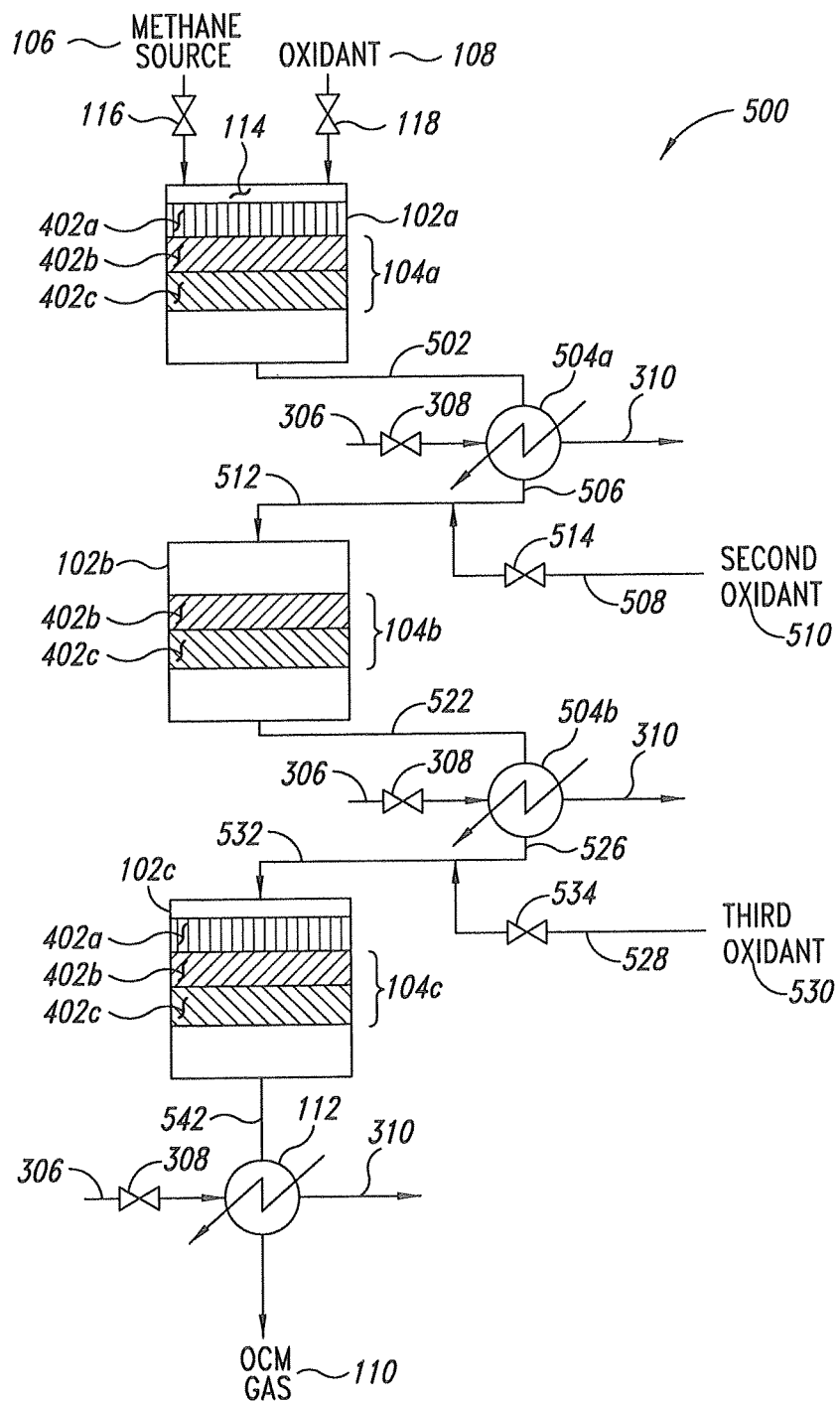
FIG. 5 shows a sectional view of an illustrative multistage vessel train including interstage cooling between the vessels for the adiabatic, exothermic, reaction of a methane source and an oxidant over at least one catalyst to provide an oxidative coupling of methane ("OCM") gas.

FIG. 5 shows a process flow diagram of a system 500 for the production of one or more alkene hydrocarbons via oxidative coupling of methane ("OCM") using a plurality of serial, fluidly coupled, vessels 102a, 102b, 102c (collectively "plurality of vessels 102"). Each of the plurality of vessels 102 may have the same or a differing number of catalyst beds 104, each containing the same or a differing number of layers 402. The first vessel 102a and the third vessel 102c each contain a single catalyst bed 104a and 104c, respectively, each having three layers 402a, 402b, and 402c. The second vessel 102b contains a single catalyst bed 104b having two layers 402b and 402c. Each of the plurality of vessels 102 operates under substantially adiabatic conditions. Thermal energy is removed from the OCM gas 110 removed from the first and second vessels 102a and 102b using one or more interstage thermal transfer devices 504a, 504b (collectively "thermal transfer devices 504"). Thermal energy is removed from the OCM gas removed from the third vessel 102c using one or more thermal transfer devices 112. Supplemental oxidants 510 and 530 may be added between some or all of the plurality of vessels 102.

In at least some situations, more than one thermal transfer device 504 may be disposed between some or all of the vessels 102. Such an arrangement may advantageously allow selective cooling and heating of the OCM gas removed from the preceding vessel 102. The operational flexibility afforded by such selective cooling and heating can permit the addition of the supplemental oxidants 510, 530 to the OCM gas at a first temperature, for example to avoid the degradation of one or more targeted products or to avoid the formation of one or more non-targeted products in the OCM gas removed from the preceding vessel 102. Such selective cooling and heating can permit the subsequent adjustment of the OCM gas temperature after the addition of the supplemental oxidant 510, 530 in preparation for introduction of the OCM gas and supplemental oxidant to a subsequent vessel 102.

Although not depicted in FIG. 5, thermal economization, for example exchanging thermal energy between one or more reactants or products having a thermal energy excess with one or more reactants or products having a thermal energy deficit, may be integrated into the serially arranged plurality of vessels 102 shown in FIG. 5.

The individual layers 402 or the entire catalyst bed 104 in each of the plurality of vessels 102 may be individually or jointly controlled or operated. In some instances the maximum temperature, temperature rise, thermal profile, or maximum temperature rise rate within a particular layer 402 or catalyst bed 104 may be controlled across one of the plurality of vessels 102, across several of the plurality of vessels 102, or across the entire plurality of vessels 102. For example, the one or more catalyst beds 104 or even one or more layers 402 forming a catalyst bed 104 within each of the plurality of vessels 102 may be operated similarly or differently based at least in part on the composition and temperature of the bulk gas mixture 114, 512, 532 introduced to the catalyst bed 104, the concentration of one or more desired hydrocarbons in the OCM gas removed from the vessel 102, the concentration of one or more non-targeted hydrocarbons in the OCM gas removed from the vessel 102, the type and number of catalyst layers 402 in the vessel 102, or the type and number of catalyst beds 104 in the vessel 102.

In some instances, a desired temperature rise or linear or non-linear temperature profile across one or more layers 402 within the catalyst bed 104 may be used to establish a target temperature or a target composition for the bulk gas mixture within a vessel 102. In some instances, a desired linear or non-linear temperature rise rate (i.e., degrees of temperature per unit depth or length of catalyst) across one or more layers 402 within the catalyst bed 104 may be used to establish a target temperature or a target composition for the bulk gas mixture within a vessel 102. In other instances, a desired linear or non-linear temperature profile across all layers 402 of the catalyst bed 104 in a vessel 102 may be used to establish a target temperature or a target composition for the bulk gas mixture within the vessel 102.

In at least some instances, at least one of the temperature, the pressure, the flow, or the composition of the bulk gas mixture 114, 512, 532 within one or more of the plurality of vessels 102 may be individually or collectively adjusted or otherwise controlled to maintain a temperature rise across any one layer 402 of the catalyst bed 104 within one or more of the plurality of vessels 102 of less than about 200° C.; less than about 150° C.; less than about 100° C.; less than about 50° C.; less than about 40° C.; less than about 30° C.; less than about 20° C.; or less than about 10° C. In at least some embodiments, at least one of the temperature, the pressure, the flow, or the composition of the bulk gas mixture 114, 512, 532 within one or more of the plurality of vessels 102 may be individually or collectively adjusted or otherwise controlled to maintain a temperature rise across the catalyst bed 104 within one or more of the plurality of vessels 102 of less than about 300° C.; less than about 250° C.; less than about 225° C.; less than about 200° C.; less than about 175° C.; less than about 150° C.; less than about 125° C.; less than about 100° C.; less than about 75° C.; or less than about 50° C.

In at least some embodiments, at least one of the temperature, the pressure, the flow, or the composition of the bulk gas mixture 114, 512, 532 within one or more of the plurality of vessels 102 may be individually or collectively adjusted or otherwise controlled to maintain a maximum temperature rise rate across any one layer 402 of the catalyst bed 104 within one or more of the plurality of vessels 102 of less than about 50° C./cm; less than about 40° C./cm; less than about 30° C./cm; less than about 25° C./cm; less than about 20° C./cm; less than about 15° C./cm; less than about 10° C./cm; less than about 5° C./cm; less than about 1° C./cm; or less than about 0.5° C./cm. In at least some embodiments, at least one of the temperature, the pressure, the flow, or the composition of the bulk gas mixture 114, 512, 532 within one or more of the plurality of vessels 102 may be individually or collectively adjusted or otherwise controlled to maintain a maximum temperature rise rate across the catalyst bed 104 within one or more of the plurality of vessels 102 of less than about 50° C./cm; less than about 40° C./cm; less than about 30° C./cm; less than about 25° C./cm; less than about 20° C./cm; less than about 15° C./cm; less than about 10° C./cm; less than about 5° C./cm; less than about 1° C./cm; or less than about 0.5° C./cm.

The temperature gradient or rise rate within the catalyst bed 104 is a function of the linear velocity, temperature, pressure, and composition of the bulk gas mixture 114, 512, 532 as well as the composition of the catalyst bed 104. The temperature gradient or rise rate within the catalyst bed 104 is also a function of the linear velocity of the bulk gas mixture 114, 512, 532 through the catalyst bed 104. The linear velocity of the bulk gas mixture 114, 512, 532 through the catalyst bed 104 can be less than about 50 meters/sec (m/s); less than about 25 m/s; less than about 20 m/s; less than about 15 m/s; less than about 10 m/s; less than about 5 m/s; less than about 2.5 m/s; less than about 1 m/s; less than about 0.5 m/s; less than about 0.1 m/s.

In at least some embodiments, at least one of the temperature, the pressure, the flow, or the composition of the bulk gas mixture 114, 512, 532 within one or more of the plurality of vessels 102 may be individually or collectively adjusted or otherwise controlled to maintain a maximum temperature within any one layer 402 of the catalyst bed 104 within one or more of the plurality of vessels 102 of less than about 1100° C.; less than about 1050° C.; less than about 1000° C.; less than about 950° C.; less than about 900° C.; less than about 850° C.; less than about 800° C.; less than about 750° C.; less than about 700° C.; less than about 650° C.; or less than about 600° C. In at least some embodiments, at least one of the temperature, the pressure, the flow, or the composition of the bulk gas mixture 114, 512, 532 within one or more of the plurality of vessels 102 may be individually or collectively adjusted or otherwise controlled to maintain a maximum temperature within the catalyst bed 104 within one or more of the plurality of vessels 102 of less than about 1100° C.; less than about 1050° C.; less than about 1000° C.; less than about 950° C.; less than about 900° C.; less than about 850° C.; less than about 800° C.; less than about 750° C. less than about 700° C.; less than about 650° C.; or less than about 600° C.

As shown in FIG. 5, the methane source 106 and the oxidant 108 are introduced to the first vessel 102a. Within the first vessel 102a, the methane source 106 and the oxidant 108 combine to form the bulk gas mixture 114 that passes through a single catalyst bed 104a containing three layers 402a, 402b, and 402c. Within the catalyst bed 104a, at least a portion of the methane present in the methane source 106 is converted to form OCM gas 502 containing one or more hydrocarbons and at least a portion of the oxygen is consumed to form water and carbon dioxide. Where oxygen is maintained as the limiting reagent in the bulk gas mixture 114, the first intermediate OCM gas 502 removed from the first vessel 102a will contain a quantity of unreacted methane. The oxygen concentration in the first intermediate OCM gas 502 can be less than about 20 mol %; less than about 15 mol %; less than about 10 mol %; less than about 5 mol %; less than about 2 mol %; less than o about 1 mol %; less than about 0.5 mol %; or less than about 0.1 mol %. The methane concentration in the first intermediate OCM gas 502 can be greater than about 1 mol %; greater than about 2 mol %; greater than about 5 mol %; greater than about 10 mol %; greater than about 20 mol %; greater than about 25 mol %; greater than about 30 mol %; greater than about 35 mol %; greater than about 40 mol %; greater than about 45 mol %; or greater than about 50 mol %. The temperature of the first intermediate OCM gas 502 can be greater than about 600° C.; greater than about 650° C.; greater than about 700° C.; greater than about 750° C.; greater than about 800° C.; greater than about 900° C.; or greater than about 950° C.

At least a portion of the thermal energy is removed from the first intermediate OCM gas 502 using one or more thermal transfer devices 504a. As shown in FIG. 5, in at least some instances, boiler feed water 306 may be used to remove at least a portion of the thermal energy present in the first intermediate OCM gas 502 to provide heated boiler feed water, saturated steam or superheated steam 310. Because of the unreacted methane present in the first cooled intermediate OCM gas 506, at least a portion of the first cooled intermediate OCM gas 506 removed from the one or more thermal transfer devices 504a may be used to provide at least a portion of the methane source for the second vessel 102b. The temperature of the first cooled intermediate OCM gas 506 can be less than about 600° C.; less than about 550° C.; less than about 500° C.; less than about 450° C.; or less than about 400° C. Although not shown in FIG. 5, in at least some situations, additional methane or other $C_{2+}$ hydrocarbons may be added to the second bulk gas mixture 512. The $C_{2+}$ alkane, alkene, alkyne, or aromatic hydrocarbon concentration within the second bulk gas mixture 512 can be less than about 10 mol %; less than about 5 mol %; less than about 3 mol %; less than about 2 mol %; less than about 1 mol %; less than about 0.5 mol %; or less than about 0.05 mol %.

In certain preferred aspects, oxygen may be maintained as the limiting reagent in the bulk gas mixture 114 in the first vessel, therefore the first intermediate cooled OCM gas 506 may have little, if any, residual oxygen content. In at least some embodiments, a second oxidant 510 can be added to the first intermediate cooled OCM gas 506 to provide a second bulk gas mixture 512 for introduction to the second vessel 102b. In some instances, the second oxidant 510 can be added as a cooled, condensed liquid or as a cooled gas to further reduce the temperature of the second bulk gas mixture 512. By adjusting the quantity of second oxidant 510 added to the first intermediate cooled OCM gas 506 and by adjusting the quantity of thermal energy removed from the first intermediate OCM gas 502 by the one or more thermal transfer devices 504a, the at least one of the temperature, the pressure, or the composition of the second bulk gas mixture 512 can be adjusted or otherwise controlled using one or more final control elements such as one or more flow control valves to adjust the boiler feed water 306 flow to the one or more thermal transfer devices 504a or one or more flow control valves to adjust the flow of the second oxidant 510 to the intermediate cooled OCM gas 506.

The methane concentration within the second bulk gas mixture 512 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %. The oxygen concentration within the bulk gas mixture 114 in the one or more vessels 102 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %.

In one or more instances, the oxygen concentration in the second bulk gas mixture 512 can be advantageously adjusted by controlling or otherwise limiting the quantity of oxygen added via the second oxidant 510 to selectively control the OCM reaction within the second vessel 102b. For example, the quantity of oxygen added via the second oxidant 510 may be controlled or otherwise adjusted to or provide a targeted thermal profile through at least one of the layers 402 forming catalyst bed 104b or to provide a targeted thermal profile through the entire catalyst bed 104b. In some embodiments, the oxygen concentration within the second bulk gas mixture 512 can be measured and adjusted via one or more feedback controllers communicably coupled to a final control element 514 on the second oxidant 510. The oxygen concentration within the second bulk gas mixture

512 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %.

In addition to the composition, the methane-to-oxygen stoichiometric ratio in the second bulk gas mixture 512 may also be measured and adjusted to selectively control the OCM reaction within the second vessel 102b. For example, the methane-to-oxygen stoichiometric ratio in the second bulk gas mixture 510 may be controlled or otherwise adjusted to provide a targeted thermal profile through at least one of the layers 402 forming catalyst bed 104b or to provide a targeted thermal profile through the entire catalyst bed 104b. Establishing the stoichiometric ratio within the gas mixture such that oxygen is the limiting reagent (i.e., maintaining a stoichiometric ratio of greater than 2:1) may advantageously minimize the likelihood of a detonation or deflagration occurring within the second vessel 102b. One or more analyzers may be used to determine either or both the methane and the oxygen concentration in second bulk gas mixture 512 and provide a input signal indicative of the concentration(s) to one or more flow or composition controllers. In at least some embodiments, one or more flow controllers can provide a control signal output to one or more final control elements, for example one or more flow control valves used to adjust the flow the second oxidant 510 to the second bulk gas mixture 512. In at least some embodiments, the stoichiometric ratio (expressed as methane molar concentration to oxygen molar concentration) in the second bulk gas mixture 512 can be greater than about 2:1; greater than about 2.25:1; greater than about 2.5:1; greater than about 2.75:1; greater than about 3:1; greater than about 3.5:1; greater than about 4:1; greater than about 4.5:1; greater than about 5:1; greater than about 7.5:1; greater than about 10:1; or greater than about 12:1.

Within the second vessel 102b, the second bulk gas mixture 512 is introduced to the single catalyst bed 104b containing two layers 402b, and 402c. Within the catalyst bed 104b, at least a portion of the methane present in the second bulk gas mixture 512 is converted to form a second intermediate OCM gas 522 containing one or more $C_{2+}$ hydrocarbons and at least a portion of the oxygen is consumed to form water and carbon dioxide. Where oxygen is maintained as the limiting reagent in the second bulk gas mixture 512, the second intermediate OCM gas 522 removed from the second vessel 102b may contain unreacted methane originally added with the methane source 106 to the first vessel 102a or unreacted methane added to the second vessel 102b. The oxygen concentration in the second intermediate OCM gas 522 can less than about 20 mol %; less than about 15 mol %; less than about 10 mol %; less than about 5 mol %; less than about 2 mol %; less than about 1 mol %; less than about 0.5 mol %; or less than about 0.1 mol %. The methane concentration in the second intermediate OCM gas 522 can be greater than about 1 mol %; greater than about 2 mol %; greater than about 5 mol %; greater than about 10 mol %; greater than about 20 mol %; greater than about 25 mol %; greater than about 30 mol %; greater than about 35 mol %; greater than about 40 mol %; greater than about 45 mol %; or greater than about 50 mol %. The temperature of the second intermediate OCM gas 522 can be greater than about 700° C.; greater than about 750° C.; greater than about 800° C.; greater than about 850° C.; greater than about 900° C.; greater than about 950° C.; greater than about 1000° C.

At least a portion of the thermal energy in the second intermediate OCM gas 522 is removed using one or more thermal transfer devices 504b. As shown in FIG. 5, in at least some instances, boiler feed water 306 may be used to remove at least a portion of the thermal energy present in the second intermediate OCM gas 522 to provide heated boiler feed water, saturated steam or superheated steam 310. One or more temperature sensors and transmitters can be used to provide a process signal indicative of the temperature of the second cooled intermediate gas 526 to at least one temperature controller. A control signal output from the at least one temperature controller may be fed to a final control element that controls the flow of boiler feed water 306 to the one or more thermal transfer devices 504b. Because of the unreacted methane present in the second cooled intermediate OCM gas 526, at least a portion of the second cooled intermediate OCM gas 526 removed from the one or more thermal transfer devices 504b may be used to provide at least a portion of the methane source for the third vessel 102c. The temperature of the second cooled intermediate OCM gas 526 can be less than about 600° C.; less than about 550° C.; less than about 500° C.; less than about 450° C.; or less than about 400° C. Although not shown in FIG. 5, in at least some situations, additional methane or other $C_{2+}$ hydrocarbons may be added to the third bulk gas mixture 532. The $C_{2+}$ alkane, alkene, alkyne, or aromatic hydrocarbon concentration within the third bulk gas mixture 532 can be less than about 10 mol %; less than about 5 mol %; less than about 3 mol %; less than about 2 mol %; less than about 1 mol %; less than about 0.5 mol %; or less than about 0.05 mol %.

Oxygen may be maintained as the limiting reagent in the second bulk gas mixture 512 introduced to the second vessel 102b, therefore the second intermediate cooled OCM gas 526 will have little, if any, residual oxygen content. In at least some embodiments, a third oxidant 530 can be added to the second intermediate cooled OCM gas 526 to provide a third bulk gas mixture 532 for introduction to the third vessel 102c. In some instances, the third oxidant 530 can be added as a cooled, condensed liquid or as a cooled gas to further lower the temperature of the third bulk gas mixture 532. By adjusting the quantity of third oxidant 530 added to the second intermediate cooled OCM gas 526 and by adjusting the quantity of thermal energy removed from the second intermediate OCM gas 522 by the one or more thermal transfer devices 504b, at least one of the temperature, the pressure, or the composition of the third bulk gas mixture 532 can be adjusted or otherwise controlled using one or more final control elements such as one or more flow control valves to adjust the boiler feed water 306 flow to the one or more thermal transfer devices 504b or one or more flow control valves to adjust the flow of the third oxidant 530 to the intermediate cooled OCM gas 526.

The methane concentration within the third bulk gas mixture 532 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %. The oxygen concentration within the bulk gas mixture 114 in the one or more vessels 102 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %.

In one or more embodiments, the oxygen concentration in the third bulk gas mixture 532 can be advantageously adjusted by controlling or otherwise limiting the quantity of oxygen added via the third oxidant 530 to selectively control the OCM reaction within the third vessel 102c. For example, the quantity of oxygen added via the third oxidant 530 may be controlled to otherwise adjusted to or provide a targeted thermal profile through at least one of the layers 402 forming catalyst bed 104c or to provide a targeted thermal profile through the entire catalyst bed 104c. In some embodiments, the oxygen concentration within the third bulk gas mixture 532 can be measured and adjusted via one or more feedback controllers communicably coupled to a final control element 534 on the third oxidant 530. The oxygen concentration within the third bulk gas mixture 532 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %.

In addition to the composition, the methane-to-oxygen stoichiometric ratio in the third bulk gas mixture 532 may also be measured and adjusted to selectively control the OCM reaction within the third vessel 102c. For example, the methane-to-oxygen stoichiometric ratio in the third bulk gas mixture 530 may be controlled or otherwise adjusted or provide a targeted thermal profile through at least one of the layers 402 forming catalyst bed 104c or to provide a targeted thermal profile through the entire catalyst bed 104c. Establishing the stoichiometric ratio within the gas mixture such that oxygen is the limiting reagent (i.e., maintaining a stoichiometric ratio of greater than 2:1) may advantageously minimize the likelihood of a detonation or deflagration occurring within the third vessel 102c. One or more analyzers may be used to determine either or both the methane and the oxygen concentration(s) in third bulk gas mixture 532 and provide a process signal input indicative of the concentration(s) to one or more controllers. In at least some embodiments the one or more controllers can provide a control signal output to one or more final control elements, for example one or more flow control valves used to adjust the flow of the third oxidant 530 to the third bulk gas mixture 532. In at least some embodiments, the stoichiometric ratio (expressed as methane molar concentration to oxygen molar concentration) in the third bulk gas mixture 532 can be greater than about 2:1; greater than about 2.25:1; greater than about 2.5:1; greater than about 2.75:1; greater than about 3:1; greater than about 3.5:1; greater than about 4:1; greater than about 4.5:1; greater than about 5:1; greater than about 7.5:1; or greater than about 10:1.

Within the third vessel 102c, the third bulk gas mixture 532 is introduced to the single catalyst bed 104c containing three layers 402a, 402b, and 402c. Within the catalyst bed 104c, at least a portion of the methane present in the third bulk gas mixture 532 is converted to form a third intermediate OCM gas 542 containing one or more $C_{2+}$ hydrocarbons and at least a portion of the oxygen is consumed to form water and carbon dioxide. Where oxygen is maintained as the limiting reagent in the third bulk gas mixture 532, the third intermediate OCM gas 542 removed from the third vessel 102c may continue to contain unreacted methane originally added with the methane source 106 to the first vessel 102a. The oxygen concentration in the third intermediate OCM gas 542 can be less than about 20 mol %; less than about 15 mol %; less than about 10 mol %; less than about 5 mol %; less than about 2 mol %; less than about 1 mol %; less than about 0.5 mol %; or less than about 0.1 mol %. The methane concentration in the third intermediate OCM gas 542 can be greater than about 1 mol %; greater than about 2 mol %; greater than about 5 mol %; greater than about 10 mol %; greater than about 20 mol %; greater than about 25 mol %; greater than about 30 mol %; greater than about 35 mol %; greater than about 40 mol %; greater than about 45 mol %; or greater than about 50 mol %. The temperature of the third intermediate OCM gas 542 can be greater than about 700° C.; greater than about 750° C.; greater than about 800° C.; greater than about 850° C.; greater than about 900° C.; greater than about 950° C.; or greater than about 1000° C.

In at least some embodiments, one or more higher hydrocarbons may be introduced to the third intermediate OCM gas 542 upstream of the thermal transfer device 112. In such instances, the heat of the OCM gas 542 may advantageously crack the higher hydrocarbons to increase the concentration of one or more desirable products (e.g., ethylene) in the OCM gas 110.

At least a portion of the thermal energy in the third intermediate OCM gas 542 is removed using one or more thermal transfer devices 112. As shown in FIG. 5, in at least some instances, boiler feed water 306 may be used to remove at least a portion of the thermal energy present in the third intermediate OCM gas 542 to provide heated boiler feed water, saturated steam or superheated steam 310. One or more temperature sensors and transmitters can be used to provide an input signal indicative of the temperature of the OCM gas 110 to at least one temperature controller. A control signal output from the at least one temperature controller may be fed to a final control element that controls the flow of boiler feed water 306 to the one or more thermal transfer devices 112.

In at least some instances, the catalyst bed 104 inlet temperature, the catalyst bed 104 outlet temperature, and one or more intermediate catalyst bed 104 temperatures in any or all of the plurality of vessels 102 may be measured using temperature sensors and transmitters to provide one or more input signals indicative of the temperature at the respective catalyst bed 104 location to one or more controllers. The ability to individually measure and control the catalyst thermal conditions in all or a portion of the plurality of vessels 102, including without limitation the inlet and outlet temperatures, temperature increase or gradient, maximum temperature, and thermal profile across a single catalyst layer, a single catalyst bed, a multi-layer catalyst bed, and a multi-catalyst bed arrangement advantageously provides the ability to individually tailor the process to achieve a desired conversion, selectivity, and yield while operating at moderate temperatures.

While operating under substantially adiabatic conditions within each of the plurality of vessels 102, the temperature increase or gradient across the catalyst bed 104 or each of the layers 402, the outlet temperature of each catalyst bed 104 or each of the layers 402, and the temperature profile of each catalyst bed 104 or each of the layers 402 may be controlled based upon the temperature, pressure, flow, and composition of the methane source 106, the oxidant 108, and the bulk gas mixture 114. Within some or all of the plurality of vessels, the catalyst bed 104 or layer 402 inlet, outlet, and intermediate temperatures may be measured using one or more temperature sensors and transmitters (not shown in FIG. 5). All or a portion of the measured catalyst bed 104 or layer 402 temperature data may be used to provide one or more process variable inputs to one or more temperature, pressure, flow, or composition controllers coupled to final control elements capable of directly or indirectly acting on at least one of either the methane source 106, the oxidant 108, the second oxidant 510, the third oxidant 530. For example, responsive to at least one of the measured catalyst bed 104 or layer 402 inlet temperature, outlet temperature, maximum temperature, temperature gradient or increase, or temperature profile, one or more of the temperature, pressure, flow, or composition of the methane source 106 or oxidant 108 may be adjusted using one or more final control elements such as one or more control valves or the like.

In addition to individually controlling the catalyst thermal conditions within each individual vessel 102, the catalyst temperature increase or gradient across all or a portion of the plurality of vessels 102, the catalyst outlet temperature across all or a portion of the plurality of vessels 102, and the catalyst temperature profile across all or a portion of the plurality of vessels 102 may be controlled based upon the temperature, pressure, flow, and composition of the methane source 106, the oxidant 108, the second oxidant 510, the third oxidant 530, the bulk gas mixture 114, the second bulk gas mixture 512, or the third bulk gas mixture 532.

Figure 6:
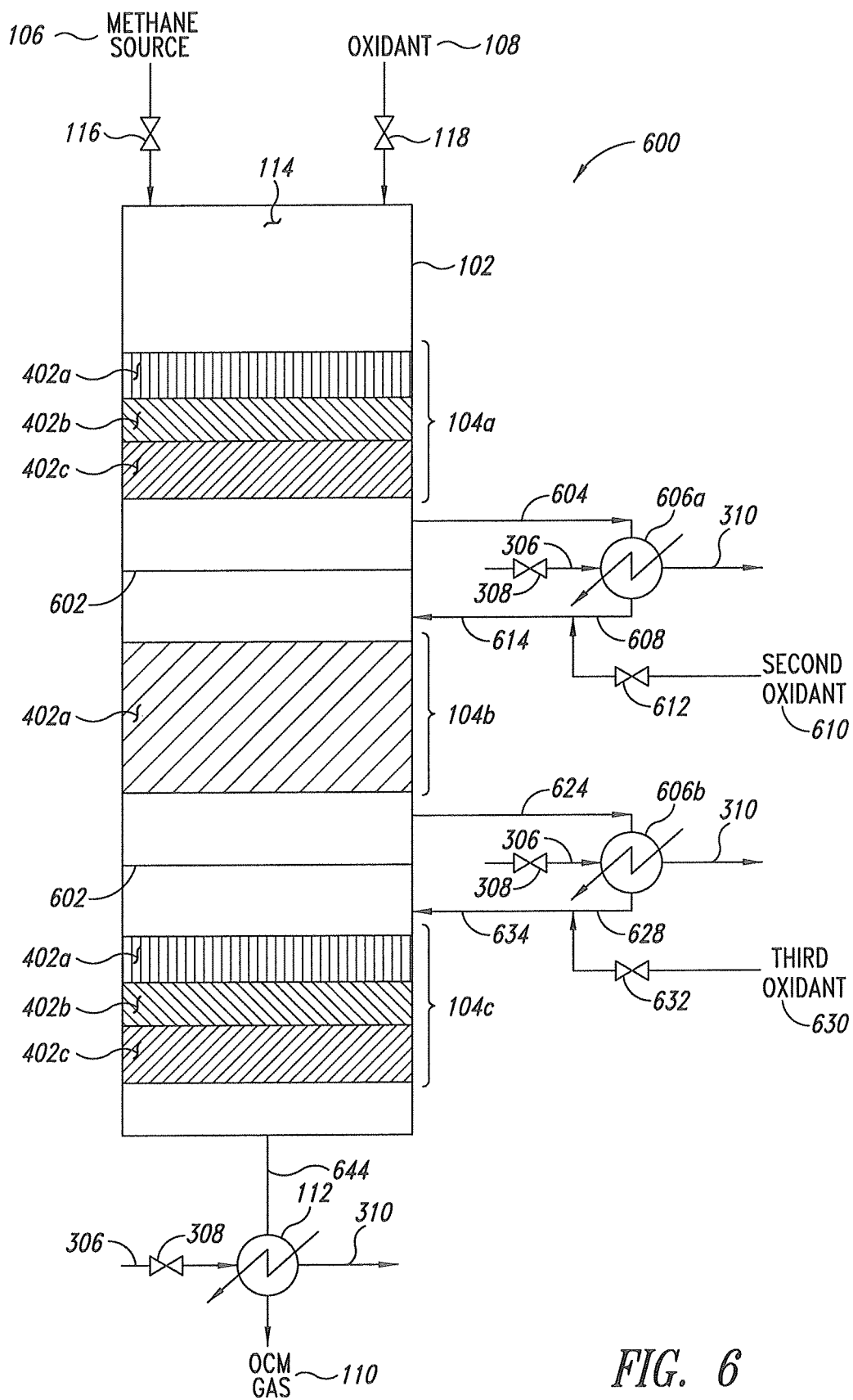
FIG. 6 shows a sectional view of an illustrative vessel containing multiple catalyst beds and including interstage cooling between the beds for the adiabatic, exothermic, reaction of a methane source and an oxidant over at least one catalyst to provide an oxidative coupling of methane ("OCM") gas.

FIG. 6 shows a process flow diagram of a system 600 for the production of one or more alkene hydrocarbons via oxidative coupling of methane ("OCM") using three catalyst beds 104a, 104b, and 104c (collectively "catalyst beds 104") disposed within a single vessel 102. Baffles 602a, 602b divide the single vessel 102 into three zones, each containing a single catalyst bed 104. The first catalyst bed 104a has three layers 402a, 402b, and 402c, the second catalyst bed 104b has a single layer 402a, and the third catalyst bed 104c has three layers 402a, 402b, and 402c. Each of the catalyst beds 104 operates under substantially adiabatic conditions. Thermal energy is removed from the OCM gas 604, 624 removed from the first and second catalyst beds 104a and 104b using one or more interstage thermal transfer devices 606a and 606b (collectively "thermal transfer devices 606"). Thermal energy is removed from the OCM gas 110 removed from the vessel 102 using one or more thermal transfer devices 112. Additional oxidant 610, 630 may be added between some or all of the plurality of beds 104.

One or more individual layers 402 in any one or more catalyst beds 104 or any one or more of the plurality catalyst beds 104 within the vessel 102 may be individually, separately, or jointly controlled or operated. For example, at least one of the inlet temperature, the outlet temperature, the temperature increase, the maximum temperature, or the temperature profile in the one or more catalyst beds 104 or even one or more layers 402 in the one or more catalyst beds 104 may be operated similarly or differently. In at least some instances, the one or more layers 402 or one or more catalyst beds 104 may be controlled based on at least one of: the temperature or composition of the bulk gas mixture 114, 614, 634 introduced to the respective catalyst bed 104; the temperature or concentration of one or more targeted hydrocarbons in the OCM gas 604, 634, 110 removed from a particular catalyst bed 104; the concentration of one or more non-targeted hydrocarbons in the OCM gas 604, 634, 110 removed from a particular catalyst bed 104; the concentration of one or more targeted hydrocarbons in the OCM gas 110 removed from the vessel 102; the concentration of one or more non-targeted hydrocarbons in the OCM gas 110 removed from the vessel 102; the type and number of catalyst layers 402 in the catalyst beds 104; or the type and number of catalyst beds 104.

Operating under substantially adiabatic conditions within each of the plurality of catalyst beds 104, the temperature increase across the catalyst bed 104 or each of the layers 402, the outlet temperature of each catalyst bed 104 or each of the layers 402, and the temperature profile of each catalyst bed 104 or each of the layers 402 may be controlled based upon the temperature, pressure, flow, and composition of the bulk gas mixture 114, 614, 634 introduced to the respective layer 402 or bed 104. Within some or all of the plurality beds 104, the catalyst bed 104 or layer 402 inlet, outlet, and intermediate temperatures may be measured using one or more temperature sensors and transmitters (not shown in FIG. 6). All or a portion of the measured catalyst bed 104 or layer 402 temperature data may be used to provide one or more process inputs to one or more temperature, pressure, flow, or composition controllers coupled to final control elements capable of directly or indirectly acting on at least one of either the methane source 106, the oxidant 108, the second oxidant 610, the third oxidant 630. For example, responsive to at least one of: the measured catalyst bed 104 or layer 402 inlet temperature; outlet temperature; maximum temperature; temperature gradient or increase; or temperature profile; one or more of the temperature, pressure, flow, or composition of the methane source 106, oxidant 108, second oxidant 610, or third oxidant 630 may be adjusted using one or more communicably coupled final control elements such as one or more control valves or the like.

In addition to individually controlling the catalyst thermal conditions within each individual catalyst bed 104, the temperature increase across all or a portion of the plurality of catalyst beds 104, the outlet temperature from all or a portion of the plurality of catalyst beds 104, and the temperature profile across all or a portion of the plurality of catalyst beds 104 may be controlled based upon the temperature, pressure, flow, and composition of the methane source 106, the oxidant 108, the second oxidant 610, the third oxidant 630, the bulk gas mixture 114, the second bulk gas mixture 614, or the third bulk gas mixture 634.

In some instances, a desired temperature rise or linear or non-linear temperature profile across one or more layers 402 within at least one catalyst bed 104 may be used to establish a target temperature or a target composition for the bulk gas mixture 114, 614, 634 introduced to the respective catalyst bed 104. In some instances, a desired linear or non-linear temperature rise rate (i.e., degrees of temperature per unit depth or length of catalyst) across one or more layers 402 within the catalyst bed 104 may be used to establish a target temperature or a target composition for the bulk gas mixture introduced to the catalyst bed 104. In other instances, a desired linear or non-linear temperature profile across all layers 402 of a catalyst bed 104 may be used to establish a target temperature or a target composition for the bulk gas mixture 114, 614, 634 introduced to the respective catalyst bed 104.

In at least some embodiments, a target temperature or a target composition for the bulk gas mixture 114, 614, 634 introduced to the respective catalyst bed 104 can maintain a maximum temperature rise across any one layer 402 of the respective catalyst bed 104 of less than about 200° C.; less than about 150° C.; less than about 100° C.; less than about 50° C.; less than about 40° C.; less than about 30° C.; less than about 20° C.; or less than about 10° C. In at least some embodiments, a target temperature or a target composition for the bulk gas mixture 114, 614, 634 introduced to the respective catalyst bed 104 can maintain a maximum temperature rise across the catalyst bed 104 of less than about 350° C.; less than about 300° C.; less than about 250° C.; less than about 225° C.; less than about 200° C.; less than about 175° C.; less than about 150° C.; less than about 125° C.; less than about 100° C.; less than about 75° C.; or less than about 50° C.

In at least some embodiments, a target temperature or a target composition for the bulk gas mixture 114, 614, 634 introduced to the respective catalyst bed 104 can maintain a maximum temperature rise rate across any one layer 402 of the respective catalyst bed 104 of less than about 50° C./cm; less than about 40° C./cm; less than about 30° C./cm; less than about 25° C./cm; less than about 20° C./cm; less than about 15° C./cm; less than about 10° C./cm; less than about 5° C./cm; less than about 1° C./cm; or less than about 0.5° C./cm. In at least some embodiments, a target temperature or a target composition for the bulk gas mixture 114, 614, 634 introduced to the respective catalyst bed 104 can maintain a maximum temperature rise rate across the respective catalyst bed 104 of less than about 50° C./cm; less than about 40° C./cm; less than about 30° C./cm; less than about 25° C./cm; less than about 20° C./cm; less than about 15° C./cm; less than about 10° C./cm; less than about 5° C./cm; less than about 1° C./cm; or less than about 0.5° C./cm.

In at least some embodiments, a target temperature or a target composition for the bulk gas mixture 114, 614, 634 introduced to the respective catalyst bed 104 can maintain a maximum temperature at any point in any one layer 402 of the respective catalyst bed 104 of less than about 1100° C.; less than about 1050° C.; less than about 1000° C.; less than about 950° C.; less than about 900° C.; less than about 850° C.; less than about 800° C.; less than about 750° C.; less than about 700° C.; less than about 650° C.; or less than about 600° C. In at least some embodiments, a target temperature or a target composition for the bulk gas mixture 114, 614, 634 introduced to the respective catalyst bed 104 can maintain a maximum temperature at any point in the at least one catalyst bed 104 of less than about 1100° C.; less than about 1050° C.; less than about 1000° C.; less than about 950° C.; less than about 900° C.; less than about 850° C.; less than about 800° C.; less than about 750° C.; less than about 700° C.; less than about 650° C.; or less than about 600° C.

As shown in FIG. 6, the methane source 106 and the oxidant 108 are introduced to the first catalyst bed 104a within the vessel 102. The methane source 106 and the oxidant 108 are combined to form the bulk gas mixture 114 that passes through the first catalyst bed 104a containing three layers 402a, 402b, and 402c. Within the first catalyst bed 104a, at least a portion of the methane present in the methane source 106 is converted to form an first intermediate OCM gas 604 containing one or more hydrocarbons. Additionally, at least a portion of the oxygen is consumed to form water and carbon dioxide within the first bed 104a.

Where oxygen is maintained as the limiting reagent in the bulk gas mixture 114 introduced to the first catalyst bed 104a, the first intermediate OCM gas 604 removed from the vessel 102 will contain a quantity of unreacted methane. The oxygen concentration in the first intermediate OCM gas 604 can be less than about 20 mol %; less than about 15 mol %; less than about 10 mol %; less than about 5 mol %; less than about 2 mol %; less than about 1 mol %; less than about 0.5 mol %; or less than about 0.1 mol %. The methane concentration in the first intermediate OCM gas 604 can be greater than about 1 mol %; greater than about 2 mol %; greater than about 5 mol %; greater than about 10 mol %; greater than about 20 mol %; greater than about 25 mol %; greater than about 30 mol %; greater than about 35 mol %; greater than about 40 mol %; greater than about 45 mol %; or greater than about 50 mol %. The temperature of the first intermediate OCM gas 604 can be less than about 1100° C.; less than about 1000° C.; less than about 900° C.; less than about 800° C.; less than about 750° C.; less than about 700° C.; or less than about 650° C.

At least a portion of the thermal energy in the first intermediate OCM gas 604 is removed using one or more thermal transfer devices 606a to provide a first cooled intermediate OCM gas 608. As shown in FIG. 6, in at least some instances, boiler feed water 306 may be used to remove at least a portion of the thermal energy present in the first intermediate OCM gas 604 to provide heated boiler feed water, saturated steam or superheated steam 310. One or more temperature sensors and transmitters can be used to provide a process signal input indicative of the temperature of the first cooled intermediate OCM gas 608 to one or more temperature, pressure, or flow controllers (not shown in FIG. 6). In at least some instances, one or more flow controllers can be used to provide a control signal output to one or more final control elements, for example one or more flow control valves used to adjust the flow of the boiler feed water 306. Because of the unreacted methane present in the first cooled intermediate OCM gas 608, at least a portion of the first cooled intermediate OCM gas 608 removed from the one or more thermal transfer devices 606a can be used to provide at least a portion of the methane source for the second catalyst bed 104b. In some instances, the temperature of the first cooled intermediate OCM gas 608 may be adjusted by bypassing all or a portion of the first intermediate OCM gas 604 around the one or more thermal transfer devices 606a. The temperature of the first cooled intermediate OCM gas 608 can be less than about 600° C.; less than about 550° C.; less than about 500° C.; less than about 450° C.; or less than about 400° C. Although not shown in FIG. 6, in at least some situations, additional methane or other $C_{2+}$ hydrocarbons may be added to the second bulk gas mixture 614. The $C_{2+}$ alkane, alkene, alkyne, or aromatic hydrocarbon concentration within the second bulk gas mixture 614 can be less than about 10 mol %; less than about 5 mol %; less than about 3 mol %; less than about 2 mol %; less than about 1 mol %; less than about 0.5 mol %; or less than about 0.05 mol %.

Oxygen is maintained as the limiting reagent in the bulk gas mixture 114 introduced to the first catalyst bed 104a, the first intermediate cooled OCM gas 608 will have little, if any, residual oxygen content. In at least some embodiments, a second oxidant 610 can be added to the first intermediate cooled OCM gas 608 to provide a second bulk gas mixture 614 for introduction to the second catalyst bed 104b. In some instances, the second oxidant 610 can be added as a cooled, condensed liquid or as a cooled gas to further lower the temperature of the second bulk gas mixture 614. By adjusting the quantity of second oxidant 610 added to the first intermediate cooled OCM gas 608 and by adjusting the quantity of thermal energy removed from the first intermediate OCM gas 604 by the one or more thermal transfer devices 606a, the methane concentration, oxygen concentration, and temperature of the second bulk gas mixture 614 can be adjusted or otherwise controlled. In at least some instances, the second oxidant 610 may be at a temperature less than the temperature of the first intermediate cooled OCM gas 608, in such instances the second oxidant provides additional cooling to the second bulk gas mixture 614. One or more temperature transmitters may be used to provide a process signal input indicative of the temperature of the second bulk gas mixture 614 to one or more temperature, pressure, or flow controllers (not shown in FIG. 6). In at least some instances, one or more temperature controllers can be used to provide a control signal output to one or more final control elements, for example one or more temperature control valves used to adjust the temperature of the second oxidant 610.

The methane concentration within the second bulk gas mixture 614 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %. The oxygen concentration within the second bulk gas mixture 614 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %.

In one or more embodiments, the oxygen concentration in the second bulk gas mixture 614 can be advantageously adjusted by controlling or otherwise limiting the quantity of oxygen added via the second oxidant 610 to control the OCM reaction within the second catalyst bed 104b. In some embodiments, one or more analyzers can measure the oxygen concentration within the second bulk gas mixture 614 and provide one or more process signal inputs indicative of the second bulk gas mixture oxygen concentration to one or more flow controllers. The one or more flow controllers can provide a control signal output to one or more final control elements, for example one or more flow control valves used to adjust the flow of the second oxidant 610 to the first intermediate cooled OCM gas 608. The oxygen concentration within the second bulk gas mixture 614 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %.

In addition to the composition, the methane-to-oxygen stoichiometric ratio in the second bulk gas mixture 614 will also affect the overall conversion of raw materials to one or more preferred products such as ethylene within the second catalyst bed 104b. Establishing the stoichiometric ratio within the gas mixture such that oxygen is the limiting reagent (i.e., maintaining a stoichiometric ratio of greater than 2:1) may advantageously minimize the likelihood of a detonation or deflagration occurring within the second catalyst bed 104b. One or more analyzers may be used to determine either or both the methane or the oxygen concentration in second bulk gas mixture 614 and provide a process signal input indicative of the concentration(s) to one or more flow controllers. In at least some embodiments the one or more flow controllers can provide a control signal output to one or more final control elements, for example one or more flow control valves used to adjust the flow of the second oxidant 610 to the second bulk gas mixture 614. In at least some embodiments, the stoichiometric ratio (expressed as methane molar concentration to oxygen molar concentration) in the second bulk gas mixture 614 can be greater than about 2:1; greater than about 2.25:1; greater than about 2.5:1; greater than about 2.75:1; greater than about 3:1; greater than about 3.5:1; greater than about 4:1; greater than about 4.5:1; greater than about 5:1; greater than about 7.5:1; or greater than about 10:1.

In the second catalyst bed 104b, the second bulk gas mixture 614 passes through a single catalyst layer 402a. Within the second catalyst bed 104b, at least a portion of the methane present in the second bulk gas mixture 614 is converted to form a second intermediate OCM gas 624 containing one or more hydrocarbons. At least a portion of the oxygen present in the second bulk gas mixture 614 is consumed within the second catalyst bed 104b to form water and carbon dioxide. Where oxygen is maintained as the limiting reagent in the second bulk gas mixture 614, the second intermediate OCM gas 624 removed from the second catalyst bed 104b will continue to contain unreacted methane originally added with the methane source 106 to the first catalyst bed 104a. The oxygen concentration in the second intermediate OCM gas 624 can be less than about 20 mol %; less than about 15 mol %; less than about 10 mol %; less than about 5 mol %; less than about 2 mol %; less than about 1 mol %; less than about 0.5 mol %; or less than about 0.1 mol %. The methane concentration in the second intermediate OCM gas 624 can be greater than about 1 mol %; greater than about 2 mol %; greater than about 5 mol %; greater than about 10 mol %; greater than about 20 mol %; greater than about 25 mol %; greater than about 30 mol %; greater than about 35 mol %; greater than about 40 mol %; greater than about 45 mol %; or greater than about 50 mol %. The temperature of the second intermediate OCM gas 624 can be less than about 1100° C.; less than about 1050° C.; less than about 1000° C.; less than about 900° C.; less than about 800° C.; less than about 700° C.; less than t about 650° C.

At least a portion of the thermal energy in the second intermediate OCM gas 624 is removed using one or more thermal transfer devices 606b to provide a second cooled intermediate OCM gas 628. As shown in FIG. 6, in at least some instances, boiler feed water 306 may be used to remove at least a portion of the thermal energy present in the second intermediate OCM gas 624 to provide heated boiler feed water, saturated steam or superheated steam 310. One or more temperature sensors and transmitters can be used to provide a process signal input indicative of the temperature of the second cooled intermediate OCM gas 628 to one or more temperature, pressure, or flow controllers (not shown in FIG. 6). In at least some instances, one or more flow controllers can be used to provide a control signal output to one or more final control elements, for example one or more flow control valves used to adjust the flow of the boiler feed water 306 to the one or more thermal transfer devices 606b. Because of the unreacted methane present in the second cooled intermediate OCM gas 628, at least a portion of the second cooled intermediate OCM gas 628 removed from the one or more thermal transfer devices 606b can be used to provide at least a portion of the methane source for the third catalyst bed 104c. In some instances, the temperature of the second cooled intermediate OCM gas 628 a portion of the second intermediate OCM gas 624 may be bypassed around the one or more thermal transfer devices 606b. The temperature of the second cooled intermediate OCM gas 628 can be less than about 600° C.; less than about 550° C.; less than about 500° C.; less than about 450° C.; or less than about 400° C. Although not shown in FIG. 6, in at least some situations, additional methane or other $C_{2+}$ hydrocarbons may be added to the third bulk gas mixture 634. The $C_{2+}$ alkane, alkene, alkyne, or aromatic hydrocarbon concentration within the third bulk gas mixture 634 can be less than about 10 mol %; less than about 5 mol %; less than about 3 mol %; less than about 2 mol %; less than about 1 mol %; less than about 0.5 mol %; or less than about 0.05 mol %.

Oxygen is maintained as the limiting reagent in the second bulk gas mixture 614 introduced to the second catalyst bed 104b, therefore the second intermediate cooled OCM gas 624 will have little, if any, residual oxygen content. In at least some embodiments, a third oxidant 630 may be added to the second intermediate cooled OCM gas 628 to provide a third bulk gas mixture 634 for introduction to the third catalyst bed 104c. In some instances, the third oxidant 630 may be added as a cooled, condensed liquid or as a cooled gas to further lower the temperature of the third bulk gas mixture 634. By adjusting the quantity of third oxidant 630 added to the second intermediate cooled OCM gas 628 and by adjusting the quantity of thermal energy removed from the second intermediate OCM gas 624 by the one or more thermal transfer devices 606b, the methane concentration, oxygen concentration, and temperature of the third bulk gas mixture 634 may be adjusted or otherwise controlled. In at least some instances, the third oxidant 630 may be at a temperature less than the temperature of the second intermediate cooled OCM gas 628, in such instances the third oxidant 630 may provide additional cooling for the third bulk gas mixture 634. One or more temperature transmitters may be used to provide a process signal input indicative of the temperature of the third bulk gas mixture 634 to one or more temperature, pressure, or flow controllers (not shown in FIG. 6). In at least some instances, one or more temperature controllers can be used to provide a control signal output to one or more final control elements, for example one or more temperature control valves used to adjust the temperature of the third oxidant 630.

The methane concentration within the third bulk gas mixture 634 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %. The oxygen concentration within the third bulk gas mixture 634 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %.

In one or more embodiments, the oxygen concentration in the third bulk gas mixture 634 can be advantageously adjusted by controlling or otherwise limiting the quantity of oxygen added via the third oxidant 630 to control the OCM reaction or to maintain a desired temperature profile or temperature rise across the third catalyst bed 104c. In some embodiments, one or more analyzers can measure the oxygen concentration within the third bulk gas mixture 634 and provide one or more process signal inputs indicative of the second bulk gas mixture oxygen concentration to one or more flow controllers. The one or more flow controllers can provide a control signal output to one or more final control elements, for example one or more flow control valves used to adjust the flow of the second oxidant 610 to the first intermediate cooled OCM gas 608. The oxygen concentration within the third bulk gas mixture 634 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %.

In addition to the composition, the methane-to-oxygen stoichiometric ratio in the third bulk gas mixture 634 will also affect the overall conversion of methane within the third catalyst bed 104c or the temperature profile or temperature rise across the third catalyst bed 104c. Establishing the stoichiometric ratio within the gas mixture such that oxygen is the limiting reagent (i.e., maintaining a stoichiometric ratio of greater than 2:1) may advantageously minimize the likelihood of a detonation or deflagration occurring within the vessel 102. One or more analyzers may be used to determine either or both the methane or the oxygen concentration in third bulk gas mixture 634 and provide a process signal input indicative of the concentration(s) to one or more flow controllers. In at least some embodiments the one or more flow controllers can provide a control signal output to one or more final control elements, for example one or more flow control valves used to adjust the flow of the third oxidant 630 to the third bulk gas mixture 634. In at least some embodiments, the stoichiometric ratio (expressed as methane molar concentration to oxygen molar concentration) in the third bulk gas mixture 634 can be greater than about 2:1; greater than about 2.25:1; greater than about 2.5:1; greater than about 2.75:1; greater than about 3:1; greater than about 3.5:1; greater than about 4:1; greater than about 4.5:1; greater than about 5:1; greater than about 7.5:1; or greater than about 10:1.

In the third catalyst bed 104c, the third bulk gas mixture 634 passes through the third catalyst bed 104c which contains three layers 402a, 402b, and 402c. Within the third catalyst bed 104c, at least a portion of the methane present in the third bulk gas mixture 634 is converted to form a third intermediate OCM gas 644 containing one or more hydrocarbons. At least a portion of the oxygen present in the third bulk gas mixture 634 is consumed to form water and carbon dioxide. If oxygen is maintained as the limiting reagent in the third bulk gas mixture 634, the third intermediate OCM gas 644 removed from the third catalyst bed 104c may continue to contain unreacted methane originally added with the methane source 106. The oxygen concentration in the third intermediate OCM gas 644 can be less than about 20 mol %; less than about 15 mol %; less than about 10 mol %; less than about 5 mol %; less than about 2 mol %; less than about 1 mol %; less than about 0.5 mol %; or less than about 0.1 mol %. The methane concentration in the third intermediate OCM gas 644 can be less than about 50 mol %; less than about 45 mol %; less than about 40 mol %; less than about 35 mol %; less than about 30 mol %; less than about 25 mol %; less than about 20 mol %; less than about 10 mol %; less than about 5 mol %; less than about 2 mol %; or less than about 1 mol %. The temperature of the third intermediate OCM gas 644 can be less than about 1100° C.; less than about 1050° C.; less than about 1000° C.; less than about 900° C.; less than about 800° C.; less than about 700° C.; less than about 650° C.

At least a portion of the thermal energy in the third intermediate OCM gas 644 is removed using one or more thermal transfer devices 112 to provide the OCM gas 110. As shown in FIG. 6, in at least some instances, boiler feed water 306 may be used to remove at least a portion of the thermal energy present in the third intermediate OCM gas 644 to provide heated boiler feed water, saturated steam or superheated steam 310. One or more temperature sensors and transmitters can be used to provide a process signal input indicative of the temperature of the third intermediate OCM gas 644 to one or more temperature, pressure, or flow controllers (not shown in FIG. 6). In at least some instances, one or more flow controllers can be used to provide a control signal output to one or more final control elements, for example one or more flow control valves used to adjust the flow of the boiler feed water 306 to the one or more thermal transfer devices 112.

Figure 7:
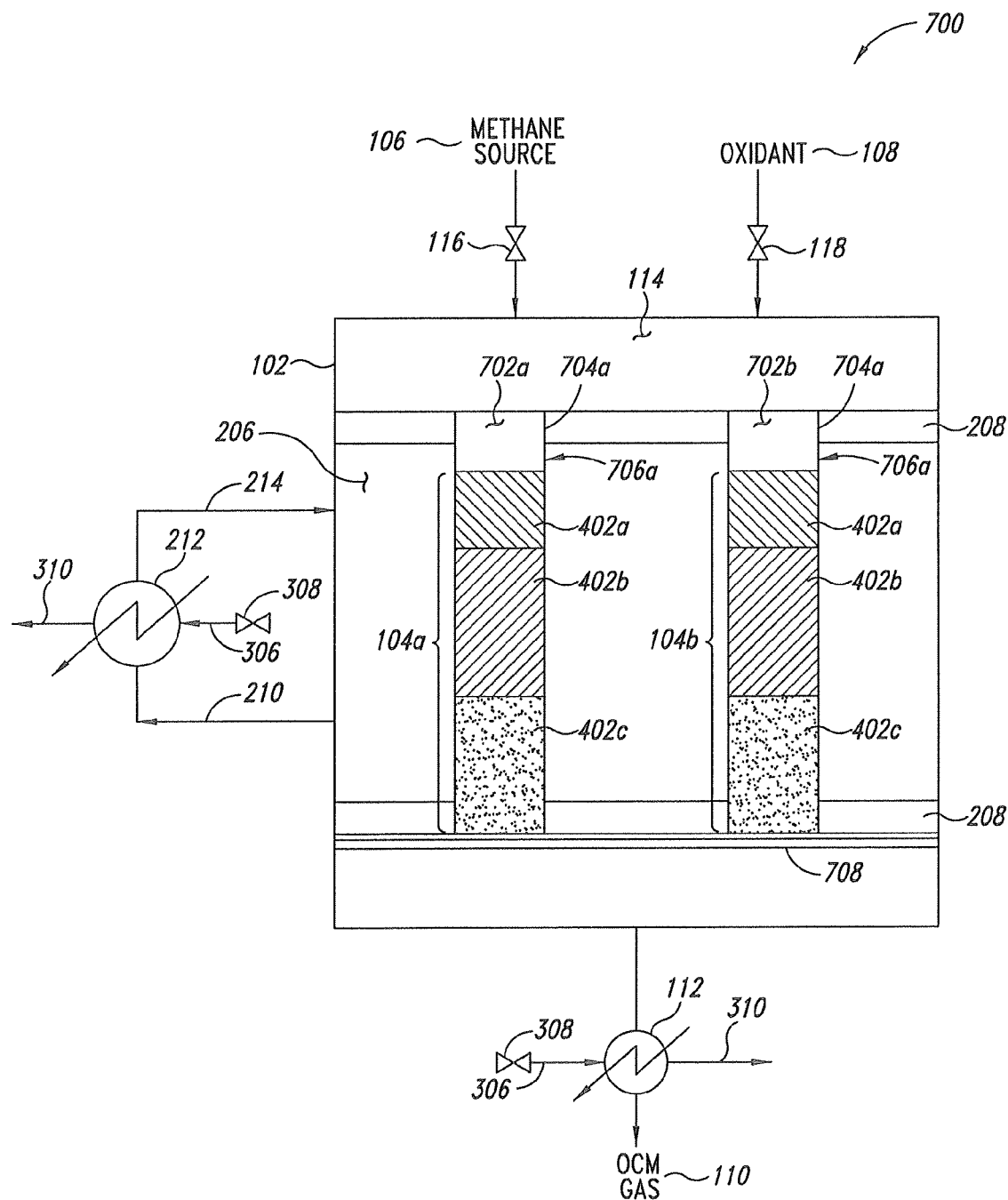
FIG. 7 shows a sectional view of an illustrative vessel containing multiple tubes at least partially filled with at least one catalyst, with the tubes surrounded by a cooling medium to support the isothermal, exothermic, reaction of a methane source and an oxidant over at least one catalyst to provide an oxidative coupling of methane ("OCM") gas.

FIG. 7 shows a process flow diagram of a system 700 for the production of one or more alkene hydrocarbons via oxidative coupling of methane ("OCM") using two illustrative catalyst beds 104a and 104b (collectively "catalyst beds 104") disposed within a single vessel 102. The catalyst beds 104 are disposed in interior spaces 702a, 702b, respectively (collectively "interior spaces 702") formed by one or more hollow members 704a, 704b (collectively "hollow members 704"). Each of the hollow members 704 includes an exterior surface 706a, 706b, respectively (collectively "exterior surface 706"). The first and second catalyst beds 104a, 104b each have three layers 402a, 402b, and 402c surrounded by one or more coolant filled voids 206 and thus operating under substantially isothermal conditions. The catalyst beds 104 provide parallel flow paths for the bulk gas mixture 114, therefore to maintain relatively equal flow through all of the catalyst beds 104, the pressure drop through each bed should be substantially similar. To achieve a substantially similar pressure drop through each of the catalyst beds, the number and composition of the layers 402 within each catalyst bed 104 may be substantially similar.

In one example, each catalyst bed 104 can include a first layer 402a, for example containing a catalyst having a composition, structure, or composition and structure providing a relatively high activity, for example a catalyst that will convert the methane present in the bulk gas 114 to one or more hydrocarbons. Each catalyst bed 104 can also include a second layer 402b, for example containing a catalyst having a composition, structure, or composition and structure providing a high selectivity for one or more targeted hydrocarbons such as ethylene. Each catalyst bed 104 can also include a third layer 402c, for example containing one or more inert materials useful in providing a support for first and second layers 402a, 402b. A support structure, for example a screen or grid is disposed proximate the hollow members 704 to retain the catalyst beds 104 within the hollow members 704.

Within each of the hollow members 704, thermal energy is liberated as the OCM reaction occurs within the catalyst bed 104. In contrast to adiabatic conditions where thermal energy is not removed from the catalyst bed 104, in an isothermal condition such as that shown in FIG. 7, the thermal energy liberated by the OCM reaction occurring inside each of the hollow members 704 flows through the hollow member 704 to a coolant in the void space 206 surrounding the hollow members 704. Structurally, the vessel 102 resembles a vertically oriented shell and tube heat exchanger with the catalyst bed 104 disposed inside the tube portion of the exchanger and the coolant disposed insider the shell of the exchanger. The thermal energy is removed from the coolant using one or more thermal transfer devices 212 fluidly coupled 210, 214 to the void space 206. In at least some situations, all or a portion of the thermal energy removed from the coolant via the one or more thermal transfer devices 212 may be transferred to one or more coolants which may be subsequently used heat boiler feed water 306 to provide heated boiler feed water, low pressure steam or superheated steam 310 as depicted in FIG. 7.

The presence of the coolant surrounding each of the hollow members 704 permits the OCM reaction to occur under substantially isothermal conditions within the hollow member 704 at a temperature substantially determined by the temperature of the coolant. Thermal energy is removed from the OCM gas 110 using one or more thermal transfer devices 112. One or more temperature transmitters can be used to provide a process signal input indicative of the temperature of the coolant in the void 206 to one or more temperature, pressure, or flow controllers (not shown in FIG. 7). In at least some instances, one or more temperature or flow controllers can be used to provide a control signal output to one or more final control elements, for example one or more flow control valves used to adjust the flow of the boiler feed water 306 to the one or more thermal transfer devices 112, or one or more temperature control devices, such as a finned air cooler, used to remove thermal energy from the coolant (not shown in FIG. 7).

Since all of the catalyst beds 104 operate under substantially similar conditions, all of the catalyst beds 104 are similarly affected by changes to the temperature, pressure, flow or composition of the bulk gas mixture 114. In a like manner, all of the catalyst beds 104 will be similarly affected by changes in the coolant temperature. At least one of the inlet temperature, the outlet temperature, the temperature increase, or the temperature profile across one or more individual layers 402 or across the catalyst beds 104 may controlled. For example, the one or more catalyst beds 104 or even one or more layers 402 in one or more catalyst beds 104 within the vessel 102 may be operated similarly or differently based on at least one of: the temperature, the pressure, the flow or the composition of the bulk gas mixture 114; the concentration of one or more targeted hydrocarbons in the OCM gas 110; the concentration of one or more non-targeted hydrocarbons in the OCM gas 110; or the type and number of catalyst layers 402 in the catalyst beds 104.

The temperature increase across the catalyst bed 104 or each of the layers 402, the outlet temperature of each catalyst bed 104 or each of the layers 402, or the temperature profile of each catalyst bed 104 or each of the layers 402 may be controlled based upon the temperature, pressure, flow, and composition of the bulk gas mixture 114. Within some or all of the plurality beds 104, the catalyst bed 104 or layer 402 inlet, outlet, and intermediate temperatures may be measured using one or more temperature sensors and transmitters (not shown in FIG. 7). All or a portion of the measured catalyst bed 104 or layer 402 temperature data may be used to provide one or more process input signals indicative of the respective temperature(s) to one or more temperature, pressure, flow, or composition controllers. The one or more controllers can provide one or more control signal outputs to one or more final control elements capable of directly or indirectly acting on at least one of: the methane source 106 temperature, pressure, flow or composition; or the oxidant 108 temperature pressure, flow, or composition.

In some instances, a desired temperature rise or linear or non-linear temperature profile across any one or more layers 402 of catalyst may be used to establish a target temperature or a target composition for the bulk gas mixture 114. In some instances, a desired linear or non-linear temperature rise rate (i.e., degrees of temperature per unit depth or length of catalyst) across one or more layers 402 within the catalyst beds 104 may be used to establish a target temperature or a target composition for the bulk gas mixture 114. In other instances, a desired linear or non-linear temperature profile across all layers 402 of a catalyst bed 104 may be used to establish a target temperature or a target composition for the bulk gas mixture 114.

In at least some embodiments, a target temperature or a target composition for the bulk gas mixture 114 introduced to the catalyst beds 104 can be selected to maintain a temperature increase across any one or more layers 402 of catalyst of less than about 200° C.; less than about 150° C.; less than about 100° C.; less than about 50° C.; less than about 40° C.; less than about 30° C.; less than about 20° C.; or less than about 10° C. In at least some embodiments, at least one of the temperature, pressure, flow or composition of the bulk gas mixture 114 may be controlled or otherwise adjusted using one or more transmitters, controllers, and final control elements to maintain a temperature rise across the catalyst beds 104 of less than about 250° C.; less than about 225° C.; less than about 200° C.; less than about 175° C.; less than about 150° C.; less than about 125° C.; less than about 100° C.; less than about 75° C.; or less than about 50° C.

In at least some embodiments, at least one of the temperature, pressure, flow or composition of the bulk gas mixture 114 may be controlled or otherwise adjusted using one or more transmitters, controllers, and final control elements to maintain a maximum temperature rise rate across any one or more layers 402 of catalyst of less than about 50° C./cm; less than about 40° C./cm; less than about 30° C./cm; less than about 25° C./cm; less than about 20° C./cm; less than about 15° C./cm; less than about 10° C./cm; less than about 5° C./cm; less than about 1° C./cm; or less than about 0.5° C./cm. In at least some embodiments, at least one of the temperature, pressure, flow or composition of the bulk gas mixture 114 may be controlled or otherwise adjusted using one or more transmitters, controllers, and final control elements to maintain a maximum temperature rise rate across the catalyst beds 104 of less than about 50° C./cm; less than about 40° C./cm; less than about 30° C./cm; less than about 25° C./cm; less than about 20° C./cm; less than about 15° C./cm; less than about 10° C./cm; less than about 5° C./cm; less than about 1° C./cm; or less than about 0.5° C./cm.

In at least some embodiments, at least one of the temperature, pressure, flow or composition of the bulk gas mixture 114 may be controlled or otherwise adjusted using one or more transmitters, controllers, and final control elements to maintain a maximum temperature within any one or more layers 402 of catalyst of less than about 1100° C.; less than about 1050° C.; less than about 1000° C.; less than about 950° C.; less than about 900° C.; less than about 850° C.; less than about 800° C.; less than about 750° C.; less than about 700° C.; less than about 650° C.; or less than about 600° C. In at least some embodiments, at least one of the temperature, pressure, flow or composition of the bulk gas mixture 114 may be controlled or otherwise adjusted using one or more transmitters, controllers, and final control elements to maintain a maximum temperature within the catalyst beds 104 of less than about 1200° C.; less than about 1100° C.; less than about 1000° C.; less than about 950° C.; less than about 900° C.; less than about 850° C.; less than about 800° C.; less than about 750° C.; less than about 700° C.; less than about 650° C.; or less than about 600° C.

In at least some embodiments, at least one of the temperature, pressure, flow or composition of the bulk gas mixture 114 may be controlled or otherwise adjusted using one or more transmitters, controllers, and final control elements to maintain a temperature range within any one or more layers 402 of catalyst of from about 400° C. to about 950° C.; about 500° C. to about 900° C.; or about 500° C. to about 850° C. In at least some embodiments, at least one of the temperature, pressure, flow or composition of the bulk gas mixture 114 may be controlled or otherwise adjusted using one or more transmitters, controllers, and final control elements to maintain a temperature range within the catalyst beds 104 of from about 400° C. to about 950° C.; about 500° C. to about 900° C.; or about 500° C. to about 850° C.

As shown in FIG. 7, the methane source 106 and the oxidant 108 are combined to form the bulk gas mixture 114 which then divides and passes through all of the catalyst beds 104. Within the catalyst beds 104, at least a portion of the methane present in the bulk gas mixture 114 is converted to form the OCM gas 110 containing one or more hydrocarbons. Additionally, at least a portion of the oxygen in the bulk gas mixture 114 is consumed to form water and carbon dioxide.

Where oxygen is maintained as the limiting reagent in the bulk gas mixture 114, the OCM gas 110 removed from the vessel 102 will contain a quantity of unreacted methane. The oxygen concentration in the OCM gas 110 can be less than about 20 mol %; less than about 15 mol %; less than about 10 mol %; less than about 5 mol %; less than about 2 mol %; less than about 1 mol %; less than about 0.5 mol %; or less than about 0.1 mol %. The methane concentration in the OCM gas 110 can be less than about 50 mol %; less than about 45 mol %; less than about 40 mol %; less than about 35 mol %; less than about 30 mol %; less than about 25 mol %; less than about 20 mol %; less than about 10 mol %; less than about 5 mol %; less than about 2 mol %; or less than about 1 mol %. The temperature of the OCM gas after exiting the vessel 102 and prior to passing through the at least one thermal transfer device 112 can be less than about 1100° C.; less than about 1050° C.; less than about 1000° C.; less than about 900° C.; less than about 800° C.; less than about 700° C.; less than about 650° C.

Figure 8:
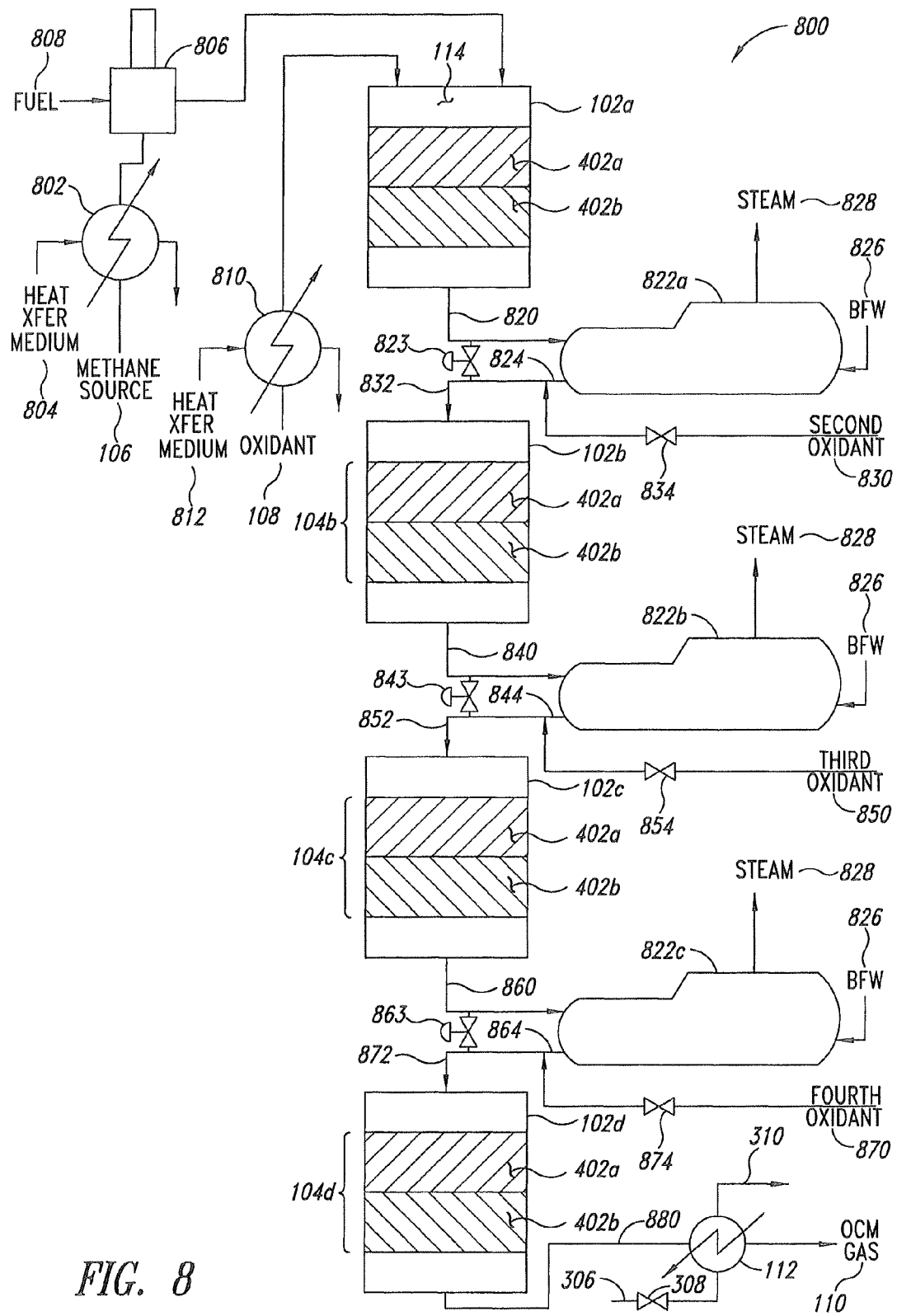
FIG. 8 shows a sectional view of an illustrative multistage vessel train, with each vessel including one or more catalyst beds, and including interstage cooling between the vessels using steam generators for the adiabatic, exothermic, reaction of a methane source and an oxidant over at least one catalyst to provide an oxidative coupling of methane ("OCM") gas.

FIG. 8 shows a process flow diagram of a system 800 for the production of one or more alkene hydrocarbons via oxidative coupling of methane ("OCM") using a plurality of serial, fluidly coupled, vessels 102a, 102b, 102c, 102d (collectively "plurality of vessels 102"). Although each of the vessels 102 are illustrated as having a single catalyst bed 104 containing two layers 402a and 402b, each of the vessels 102 may have more than one catalyst bed 104 and each catalyst bed 104 may have a greater or lesser number of layers 402. Each of the plurality of vessels 102 operates under substantially adiabatic conditions. Thermal energy is removed from the OCM gas 820, 840, 860, removed, respectively, from the first, second, and third vessels 102a, 102b, 102c using one or more interstage thermal transfer devices 822a, 822b, 822c (collectively "thermal transfer devices 822"). Thermal energy is removed from the OCM gas 110 removed from the fourth vessel 102d using one or more thermal transfer devices 112. One or more supplemental oxidants 830, 850, 870 may be added between some or all of the plurality of vessels 102.

Although not depicted in FIG. 8, exchanging thermal energy between one or more reactants or products having a thermal energy excess with one or more reactants or products having a thermal energy deficit, may be integrated into the serially arranged plurality of vessels 102 shown in FIG. 8.

In at least some instances, the catalyst bed 104 inlet temperature, the catalyst bed 104 outlet temperature, and one or more intermediate catalyst bed 104 temperatures in any or all of the plurality of vessels 102 may be measured using temperature sensors and transmitters to provide one or more input signals indicative of the temperature at the respective catalyst bed 104 location to one or more controllers. The ability to individually measure and control the catalyst thermal conditions in all or a portion of the plurality of vessels 102, including without limitation the inlet and outlet temperatures, temperature increase or gradient, maximum temperature, and thermal profile across a single catalyst layer, a single catalyst bed, a multi-layer catalyst bed, and a multi-catalyst bed arrangement advantageously provides the ability to individually control the process 800 to achieve a targeted conversion, selectivity, and yield while operating at moderate temperatures.

Operating under substantially adiabatic conditions within each of the plurality of vessels 102, the temperature increase or gradient across the catalyst bed 104 or each of the layers 402, the outlet temperature of each catalyst bed 104 or each of the layers 402, and the temperature profile of each catalyst bed 104 or each of the layers 402 may be controlled based upon the temperature, pressure, flow, and composition of the bulk gas mixture 114, 832, 852, 872 that is introduced to the catalyst beds 104 in each of the plurality of vessels 102. Within some or all of the plurality of vessels 102, the catalyst bed 104 or layer 402 inlet, outlet, and intermediate temperatures may be measured using one or more temperature sensors and transmitters (not shown in FIG. 8). All or a portion of the measured catalyst bed 104 or layer 402 temperature data within each of the respective plurality of vessels 102 may be used to provide one or more process variable inputs to one or more temperature, pressure, flow, or composition controllers. The one or more controllers can provide one or more control signal outputs to final control elements capable of directly or indirectly acting on at least one of: the methane source 106, the oxidant 108, the second oxidant 830, the third oxidant 850, or the fourth oxidant 870. For example, responsive to at least one of the measured catalyst bed 104 or layer 402 inlet temperature, outlet temperature, maximum temperature, temperature gradient or increase, or temperature profile in at least one of the plurality of vessels 102, one or more of the temperature, pressure, flow, or composition of the bulk gas mixture 114, 832, 852, 872 introduced to the respective vessel 102 may be adjusted using one or more final control elements such as one or more control valves or the like.

In addition to individually controlling the catalyst thermal conditions within each individual vessel 102, the catalyst temperature increase or gradient across all or a portion of the plurality of vessels 102, the catalyst outlet temperature across all or a portion of the plurality of vessels 102, and the catalyst temperature profile across all or a portion of the plurality of vessels 102 may be controlled based upon the temperature, pressure, flow, and composition of the methane source 106, the oxidant 108, the second oxidant 830, the third oxidant 850, or the fourth oxidant 870, the bulk gas mixture 114, the second bulk gas mixture 824, the third bulk gas mixture 844, or the fourth bulk gas mixture 864. Such flexibility in control permits the operation of the process 800 at a wide variety of process conditions and compositions to enable the efficient production of one or more targeted hydrocarbons at moderate operating temperatures.

One or more individual layers 402 in a catalyst bed 104 in each of the plurality of vessels 102 or the entire catalyst bed 104 in each of the plurality of vessels 102 may be individually or jointly controlled or operated. In some instances the inlet temperature, outlet temperature, maximum temperature, temperature increase, or thermal profile in a particular layer 402 or a particular catalyst bed 104 may be controlled across one of the plurality of vessels 102, across several of the plurality of vessels 102, or across the entire plurality of vessels 102. For example, the one or more catalyst beds 104 or even one or more layers 402 forming a catalyst bed 104 within each of the plurality of vessels 102 may be operated similarly or differently between vessels 102 based at least in part on the composition and temperature of the bulk gas mixture introduced to the vessel 102, the concentration of one or more targeted hydrocarbons in the OCM gas 820, 840, 860, 110 removed from the vessel 102, the concentration of one or more non-targeted hydrocarbons in the OCM gas removed from the vessel 102, the type and number of catalyst layers 402 in one or more catalyst beds 104 in the respective vessel 102, or the type and number of catalyst beds 104 in the respective vessel 102.

In some instances, at least one of: the inlet temperature, the outlet temperature, the maximum temperature, the temperature rise, or the thermal profile across one or more layers 402 within the catalyst bed 104 may be used to control or otherwise adjust at least one of the temperature, pressure, flow, or composition of the bulk gas mixture 114, 832, 852, 872 introduced to the vessel 102. In some instances, at least one of: the inlet temperature, the outlet temperature, the maximum temperature, the temperature rise, or the thermal profile across the catalyst bed 104 in one vessel 102 may be used to control or otherwise adjust at least one of the temperature, pressure, flow, or composition of the bulk gas mixture 114, 832, 852, 872 introduced to the vessel 102. In other instances, at least one of: the inlet temperature, the outlet temperature, the maximum temperature, the temperature rise, or the thermal profile across the catalyst beds 104 in two or more vessels 102 may be used to control or otherwise adjust at least one of the temperature, pressure, flow, or composition of the bulk gas mixture 114, 832, 852, 872 introduced to the respective two or more vessels 102.

In at least some embodiments, at least one of: the temperature; the pressure; the flow; or the composition of the bulk gas mixture 114, 832, 852, 872 introduced to one or more of the plurality of vessels 102 may be controlled or otherwise adjusted to maintain a temperature increase across any one layer 402 of the catalyst bed 104 within one or more of the plurality of vessels 102 of less than about 200° C.; less than about 150° C.; less than about 100° C.; less than about 50° C.; less than about 40° C.; less than about 30° C.; less than about 20° C.; or less than about 10° C. In at least some embodiments, at least one of: the temperature; the pressure; the flow; or the composition of the bulk gas mixture 114, 832, 852, 872 within one or more of the plurality of vessels 102 can be controlled or otherwise adjusted to maintain a temperature increase across the catalyst bed 104 within one or more of the plurality of vessels 102 of less than about 250° C.; less than about 225° C.; less than about 200° C.; less than about 175° C.; less than about 150° C.; less than about 125° C.; less than about 100° C.; less than about 75° C.; or less than about 50° C.

In at least some embodiments, at least one of: the temperature; the pressure; the flow; or the composition of the bulk gas mixture 114, 832, 852, 872 within one or more of the plurality of vessels 102 can be controlled or otherwise adjusted to maintain a maximum temperature rise rate across any one layer 402 of the catalyst bed 104 within one or more of the plurality of vessels 102 of less than about 50° C./cm; less than about 40° C./cm; less than about 30° C./cm; less than about 25° C./cm; less than about 20° C./cm; less than about 15° C./cm; less than about 10° C./cm; less than about 5° C./cm; less than about 1° C./cm; or less than about 0.5° C./cm. In at least some embodiments, at least one of: the temperature; the pressure; the flow; or the composition of the bulk gas mixture 114, 832, 852, 872 within one or more of the plurality of vessels 102 can be controlled or otherwise adjusted to maintain a maximum temperature rise rate across the catalyst bed 104 within one or more of the plurality of vessels 102 of less than about 50° C./cm; less than about 40° C./cm; less than about 30° C./cm; less than about 25° C./cm; less than about 20° C./cm; less than about 15° C./cm; less than about 10° C./cm; less than about 5° C./cm; less than about 1° C./cm; or less than about 0.5° C./cm.

In at least some embodiments, at least one of: the temperature; the pressure; the flow; or the composition of the bulk gas mixture 114, 832, 852, 872 within one or more of the plurality of vessels 102 can be controlled or otherwise adjusted to maintain a maximum temperature within any one layer 402 of the catalyst bed 104 within one or more of the plurality of vessels 102 of less than about 1100° C.; less than about 1050° C.; less than about 1000° C.; less than about 950° C.; less than about 900° C.; less than about 850° C.; less than about 800° C.; less than about 750° C.; less than about 700° C.; less than about 650° C.; or less than about 600° C. In at least some embodiments, at least one of: the temperature; the pressure; the flow; or the composition of the bulk gas mixture 114, 832, 852, 872 within one or more of the plurality of vessels 102 can be controlled or otherwise adjusted to maintain a maximum temperature within the catalyst bed 104 within one or more of the plurality of vessels 102 of less than about 1100° C.; less than about 1050° C.; less than about 1000° C.; less than about 950° C.; less than about 900° C.; less than about 850° C.; less than about 800° C.; less than about 750° C.; less than about 700° C.; less than about 650° C.; or less than about 600° C.

As shown in FIG. 8, a variable quantity of thermal energy may be added to variably increase the temperature of either or both the methane source 106 and the oxidant 108 prior to their introduction to the first vessel 102a. Thermal energy may be added to increase the temperature of the methane source 106 using one or more thermal transfer devices 802, one or more combustion heaters 806, or combinations thereof. In at least some instances, the one or more thermal transfer devices 802 can include one or more non-contact heat exchangers where a heat transfer medium 804 releases thermal energy to the methane source 106. In at least some instances, at least a portion of the heat transfer medium can include the OCM gas 110 removed from the fourth vessel 102d. In at least some embodiments, a one or more combustion heaters 806 using one or more fuels 808 may be used to provide all or a portion of the thermal energy to the methane source 106. One or more temperature transmitters can provide a process signal input indicative of the temperature of the methane source 106 to one or more temperature controllers. The one or more temperature controllers can provide a control output signal to one or more final control elements, for example one or more flow control valves used to control the flow of heat transfer medium 804 to the one or more thermal transfer devices 802 or to control the flow of the one or more fuels 808 to the one or more combustion heaters 806.

A variable quantity of thermal energy may also be added to variably increase the temperature of the oxidant 108 using one or more thermal transfer devices 810, one or more combustion heaters (not shown in FIG. 8), or combinations thereof. In at least some instances, the one or more thermal transfer devices 810 can include one or more non-contact heat exchangers where a heat transfer medium 812 is used to provide thermal energy to the oxidant 108. In at least some instances, at least a portion of the heat transfer medium can include the OCM gas 110 removed from the fourth vessel 102d. One or more temperature transmitters can provide a process signal input indicative of the temperature of the oxidant 108 to one or more temperature controllers. The one or more temperature controllers can provide a control output signal to one or more final control elements, for example one or more flow control valves used to control the flow of heat transfer medium 812 to the one or more thermal transfer devices 810 or to control the flow of the one or more fuels to the one or more combustion heaters.

The methane source 106 and the oxidant 108 combine to form the bulk gas mixture 114 prior to passing through a single catalyst bed 104 containing two layers 402a and 402b. Within the catalyst bed 104, at least a portion of the methane present in the bulk gas mixture 114 is converted to form a first intermediate OCM gas 820 containing one or more hydrocarbons and at least a portion of the oxygen is consumed to form water and carbon dioxide. Where oxygen is maintained as the limiting reagent in the bulk gas mixture 114, the first intermediate OCM gas 820 removed from the first vessel 102a will contain unreacted methane. The oxygen concentration in the first intermediate OCM gas 820 can be less than about 20 mol %; at most about 15 mol %; at most about 10 mol %; at most about 5 mol %; less than about 2 mol %; less than about 1 mol %; less than about 0.5 mol %; or less than about 0.1 mol %. The methane concentration in the first intermediate OCM gas 820 can be greater than about 1 mol %; greater than about 2 mol %; greater than about 5 mol %; greater than about 10 mol %; greater than about 20 mol %; greater than about 25 mol %; greater than about 30 mol %; greater than about 35 mol %; greater than about 40 mol %; greater than about 45 mol %; or greater than about 50 mol %. The temperature of the first intermediate OCM gas 820 can be less than about 1100° C.; less than about 1050° C.; less than about 1000° C.; less than about 900° C.; less than about 800° C.; less than about 700° C.; or less than about 650° C.

At least a portion of the thermal energy carried with the first intermediate OCM gas 820 is removed using one or more thermal transfer devices 822a to provide a first cooled intermediate OCM gas 824. As shown in FIG. 8, in at least some instances, boiler feed water 826 may be used to remove at least a portion of the thermal energy present in the first intermediate OCM gas 820 to provide steam 828. One or more temperature sensors and transmitters can be used to provide a process signal indicative of the temperature of the first cooled intermediate gas 824 to at least one temperature controller. A control signal output provided by the at least one temperature controller may be fed to a final control element, for example a flow control valve, that controls or otherwise adjusts the flow of boiler feed water 306 to the one or more thermal transfer devices 822a. Because of the unreacted methane present in the first cooled intermediate OCM gas 824, at least a portion of the first cooled intermediate OCM gas 824 removed from the one or more thermal transfer devices 822a may be used to provide at least a portion of the methane source for the second vessel 102b. In some instances, the temperature of the first cooled intermediate OCM gas 824 may be adjusted by bypassing all or a portion of the first intermediate OCM gas 820 around the one or more thermal transfer devices 822a using one or more bypass control devices 823. The temperature of the first cooled intermediate OCM gas 824 can be less than about 600° C.; less than about 550° C.; less than about 500° C.; less than about 450° C.; less than about 400° C. Although not shown in FIG. 8, in at least some situations, additional methane or other $C_{2+}$ hydrocarbons may be added to the second bulk gas mixture 832. The $C_{2+}$ alkane, alkene, alkyne, or aromatic hydrocarbon concentration within the second bulk gas mixture 832 can be less than about 10 mol %; less than about 5 mol %; less than about 3 mol %; less than about 2 mol %; less than about 1 mol %; less than about 0.5 mol %; or less than about 0.05 mol %.

Oxygen may be maintained as the limiting reagent in the bulk gas mixture 114 in the first vessel 102a, therefore the first intermediate cooled OCM gas 824 will have little, if any, residual oxygen content. In at least some embodiments, a second oxidant 830 can be added to the first intermediate cooled OCM gas 824 to provide a second bulk gas mixture 832 for introduction to the second vessel 102b. In some instances, the second oxidant 830 can be added as a cooled, condensed liquid or as a cooled gas to further lower the temperature of the second bulk gas mixture 832. In some situations, the composition of the second bulk gas mixture 832 can be controlled or otherwise adjusted using one of more analyzers to provide a process signal input indicative of the composition of the second bulk gas mixture 832 to one or more flow or composition controllers. The one or more controllers can provide a control signal output to one or more final control elements, for example one or more flow control valves capable of controlling or otherwise adjusting the flow of the second oxidant 830. In some situations the temperature of the second bulk gas mixture 832 can be controlled or otherwise adjusted using one of more temperature transmitters to provide a process signal input indicative of the temperature of the second bulk gas mixture 832 to one or more temperature controllers. The one or more controllers can provide a control signal output to one or more final control elements, for example one or more flow control valves capable of controlling or otherwise adjusting the flow of the boiler feed water 306 to the one or more thermal transfer devices 822a.

The methane concentration within the second bulk gas mixture 832 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %. The oxygen concentration within the second bulk gas mixture 832 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %.

In one or more embodiments, the oxygen concentration in the second bulk gas mixture 832 can be advantageously adjusted by controlling or otherwise limiting the quantity of oxygen added via the second oxidant 530 to at least one of: selectively control the OCM reaction within the second vessel 102b, or to provide a thermal profile through at least one of the catalyst bed 104b, or one of the plurality of layers 402 forming the catalyst bed 104b. In some embodiments, the oxygen concentration within the second bulk gas mixture 832 can be measured and adjusted via one or more feedback controllers communicably coupled to a final control element 834 on the second oxidant 830. The oxygen concentration within the second bulk gas mixture 832 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %. Although not shown in FIG. 8, in at least some instances, one or more hydrocarbons, including methane or $C_{2+}$ hydrocarbons, may be introduced to the second bulk gas mixture 832.

In addition to the composition, the methane-to-oxygen stoichiometric ratio in the second bulk gas mixture 832 may also be measured and adjusted to selectively control the OCM reaction within the second vessel 102b. For example, the methane-to-oxygen stoichiometric ratio in the second bulk gas mixture 832 may be controlled or otherwise adjusted or provide a targeted thermal profile through at least one of the layers 402 forming catalyst bed 104b or to provide a targeted thermal profile through the entire catalyst bed 104b. Maintaining the stoichiometric ratio within the second bulk gas mixture 832 such that oxygen is the limiting reagent (i.e., maintaining a stoichiometric ratio of greater than 2:1) may advantageously minimize the likelihood of a detonation or deflagration occurring within the second vessel 102b. One or more analyzers may be used to determine either or both the methane and the oxygen concentration in second bulk gas mixture 832 and provide a process signal input that is indicative of the concentration(s) to one or more flow or composition controllers. The one or more controllers can provide a control output signal to one or more final control elements configured, for example, to adjust the flow of either or both the methane source and the oxidant to the second bulk gas mixture 832. In at least some embodiments, the stoichiometric ratio (expressed as methane molar concentration to oxygen molar concentration) in the second bulk gas mixture 832 can be greater than about 2:1; greater than about 2.25:1; greater than about 2.5:1; greater than about 2.75:1; greater than about 3:1; greater than about 3.5:1; greater than about 4:1; greater than about 4.5:1; greater than about 5:1; greater than about 7.5:1; or greater than about 10:1.

Within the second vessel 102b, the second bulk gas mixture 832 is introduced to a single catalyst bed 104 having two layers 402a and 402b. Within the catalyst bed 104, at least a portion of the methane present in the second bulk gas mixture 832 is converted to form a second intermediate OCM gas 840 containing one or more $C_{2+}$ hydrocarbons and at least a portion of the oxygen is consumed to form water and carbon dioxide. Where oxygen is maintained as the limiting reagent in the second bulk gas mixture 832, the second intermediate OCM gas 840 removed from the second vessel 102b may contain unreacted methane originally added with the methane source 106 to the first vessel 102a or unreacted methane added to the second vessel 102b (not shown in FIG. 8). The oxygen concentration in the second intermediate OCM gas 840 can be less than about 20 mol %; less than about 15 mol %; less than about 10 mol %; less than about 5 mol %; less than about 2 mol %; less than about 1 mol %; less than about 0.5 mol %; or less than about 0.1 mol %. The methane concentration in the second intermediate OCM gas 840 can be greater than about 1 mol %; greater than about 2 mol %; greater than about 5 mol %; greater than about 10 mol %; greater than about 20 mol %; greater than about 25 mol %; greater than about 30 mol %; greater than about 35 mol %; greater than about 40 mol %; greater than about 45 mol %; or greater than about 50 mol %. The temperature of the second intermediate OCM gas 840 can be less than about 1100° C.; less than about 1050° C.; less than about 1000° C.; less than about 900° C.; less than about 800° C.; less than about 700° C.; less than about 650° C.

At least a portion of the thermal energy in the second intermediate OCM gas 840 is removed using one or more thermal transfer devices 822b to provide a second cooled intermediate OCM gas 844. As shown in FIG. 8, in at least some instances, boiler feed water 826 may be used to remove at least a portion of the thermal energy present in the second intermediate OCM gas 840 to provide steam 828. One or more temperature transmitters can be used to provide a process signal input indicative of the second cooled intermediate OCM gas 844 to one or more temperature or flow controllers. A control signal output from the at least one controller may be provided to a final control element, for example a flow control valve used to control or otherwise adjust the flow of boiler feed water 306 to the one or more thermal transfer devices 822b. Because of the unreacted methane present in the second cooled intermediate OCM gas 844, at least a portion of the second cooled intermediate OCM gas 844 removed from the one or more thermal transfer devices 822b may be used to provide at least a portion of the methane source in the third bulk gas mixture 852. In some instances, the temperature of the second cooled intermediate OCM gas 844 may be adjusted by bypassing all or a portion of the second intermediate OCM gas 840 around the one or more thermal transfer devices 822b using one or more bypass control devices 843. The temperature of the second cooled intermediate OCM gas 844 can be less than about 600° C.; less than about 550° C.; less than about 500° C.; less than about 450° C.; or less than about 400° C. Although not shown in FIG. 8, in at least some situations, additional methane or other $C_{2+}$ hydrocarbons may be added to the third bulk gas mixture 852. The $C_{2+}$ alkane, alkene, alkyne, or aromatic hydrocarbon concentration within the third bulk gas mixture 852 can be less than about 10 mol %; less than about 5 mol %; less than about 3 mol %; less than about 2 mol %; less than about 1 mol %; less than about 0.5 mol %; or less than about 0.05 mol %.

Oxygen may be maintained as the limiting reagent in the second bulk gas mixture 832 introduced to the second vessel 102*b*, therefore the second intermediate cooled OCM gas 844 will have little, if any, residual oxygen content. In at least some embodiments, a third oxidant 850 can be added to the second intermediate cooled OCM gas 844 to provide a third bulk gas mixture 852 for introduction to the third vessel 102*c*. In some instances, the third oxidant 850 can be added as a cooled, condensed liquid or as a cooled gas to further lower the temperature of the third bulk gas mixture 852. In some situations, the composition of the third bulk gas mixture 852 can be controlled or otherwise adjusted using one of more analyzers to provide a process signal input indicative of the composition of the third bulk gas mixture 852 to one or more flow or composition controllers. The one or more controllers can provide a control signal output to one or more final control elements, for example one or more flow control valves capable of controlling or otherwise adjusting the flow of the third oxidant 850. In some situations the temperature of the third bulk gas mixture 852 can be controlled or otherwise adjusted using one of more temperature transmitters to provide a process signal input indicative of the temperature of the third bulk gas mixture 852 to one or more temperature controllers. The one or more controllers can provide a control signal output to one or more final control elements, for example one or more flow control valves capable of controlling or otherwise adjusting the flow of the boiler feed water 306 to the one or more thermal transfer devices 822*b*.

The methane concentration within the third bulk gas mixture 852 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %. The oxygen concentration within the third bulk gas mixture 852 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %.

In one or more embodiments, the oxygen concentration in the third bulk gas mixture 852 may also be measured and adjusted to selectively control the OCM reaction within the third vessel 102*c*. For example, the oxygen concentration in the third bulk gas mixture 852 may be controlled or otherwise adjusted or provide a targeted thermal profile through at least one of the layers 402 forming catalyst bed 104*c* or to provide a targeted thermal profile through the entire catalyst bed 104*c*. In some embodiments, the oxygen concentration within the third bulk gas mixture 852 can be measured and adjusted via one or more feedback controllers communicably coupled to a final control element 854 on the third oxidant 850. The oxygen concentration within the third bulk gas mixture 852 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %.

In addition to the composition, the methane-to-oxygen stoichiometric ratio in the third bulk gas mixture 852 may also be measured and adjusted to selectively control the OCM reaction within the third vessel 102*c*. For example, the methane-to-oxygen stoichiometric ratio in the third bulk gas mixture 852 may be controlled or otherwise adjusted or provide a targeted thermal profile through at least one of the layers 402 forming catalyst bed 104*c* or to provide a targeted thermal profile through the entire catalyst bed 104*c*. Establishing the stoichiometric ratio within the third bulk gas mixture 852 such that oxygen is the limiting reagent (i.e., maintaining a stoichiometric ratio of greater than 2:1) may advantageously minimize the likelihood of a detonation or deflagration occurring within the third vessel 102*c*. One or more analyzers may be used to determine either or both the methane or the oxygen concentration(s) in third bulk gas mixture 852 and provide a input signal indicative of the concentration(s) to one or more flow or composition controllers. The one or more controllers can provide a control signal output to one or more final control elements configured, for example, to adjust the flow of the third oxidant 850 to the third bulk gas mixture 852. In at least some embodiments, the stoichiometric ratio (expressed as methane molar concentration to oxygen molar concentration) in the third bulk gas mixture 852 can be greater than about 2:1; greater than about 2.25:1; greater than about 2.5:1; greater than about 2.75:1; greater than about 3:1; greater than about 3.5:1; greater than about 4:1; greater than about 4.5:1; greater than about 5:1; greater than about 7.5:1; or greater than about 10:1.

Within the third vessel 102*c*, the third bulk gas mixture 852 is introduced to a single catalyst bed 104*c* having two layers 402*a* and 402*b*. Within the catalyst bed 104*c*, at least a portion of the methane present in the third bulk gas mixture 852 is converted to form a third intermediate OCM gas 860 containing one or more $C_{2+}$ hydrocarbons and at least a portion of the oxygen is consumed to form water and carbon dioxide.

Where oxygen is maintained as the limiting reagent in the third bulk gas mixture 852, the third intermediate OCM gas 860 removed from the third vessel 102*c* may continue to contain unreacted methane added to the third vessel 102*c*, or originally added with the methane source 106 to the first vessel 102*a*. The oxygen concentration in the third intermediate OCM gas 860 can be less than about 20 mol %; less than about 15 mol %; less than about 10 mol %; less than about 5 mol %; less than about 2 mol %; less than about 1 mol %; less than about 0.5 mol %; or less than about 0.1 mol %. The methane concentration in the third intermediate OCM gas 860 can be greater than about 1 mol %; greater than about 2 mol %; greater than about 5 mol %; greater than about 10 mol %; greater than about 20 mol %; greater than about 25 mol %; greater than about 30 mol %; greater than about 35 mol %; greater than about 40 mol %; greater than about 45 mol %; or greater than about 50 mol %. The temperature of the third intermediate OCM gas 860 can be less than about 1100° C.; less than about 1050° C.; less than about 1000° C.; less than about 900° C.; less than about 800° C.; less than about 700° C.; or less than about 650° C.

At least a portion of the thermal energy in the third intermediate OCM gas 860 is removed using one or more thermal transfer devices 822*c* to provide a third cooled intermediate OCM gas 864. As shown in FIG. 8, in at least some instances, boiler feed water 826 may be used to remove at least a portion of the thermal energy present in the third intermediate OCM gas 860 to provide steam 828. One or more temperature transmitters can be used to provide a process signal input indicative of the third cooled intermediate OCM gas 864 to one or more temperature or flow controllers. A control signal output from the at least one controller may be provided to a final control element, for example a flow control valve used to control or otherwise adjust the flow of boiler feed water 306 to the one or more thermal transfer devices 822c. Because of the unreacted methane present in the third cooled intermediate OCM gas 864, at least a portion of the third cooled intermediate OCM gas 864 removed from the one or more thermal transfer devices 822c may be used to provide at least a portion of the methane source in the fourth bulk gas mixture 872. In some instances, the temperature of the third cooled intermediate OCM gas 864 may be adjusted by bypassing all or a portion of the third intermediate OCM gas 860 around the one or more thermal transfer devices 822c using one or more bypass control devices 863. The temperature of the third cooled intermediate OCM gas 864 can be less than about 600° C.; less than about 550° C.; less than about 500° C.; less than about 450° C.; or less than about 400° C. Although not shown in FIG. 8, in at least some situations, additional methane or other $C_{2+}$ hydrocarbons may be added to the fourth bulk gas mixture 872. The $C_{2+}$ alkane, alkene, alkyne, or aromatic hydrocarbon concentration within the fourth bulk gas mixture 872 can be less than about 10 mol %; less than about 5 mol %; less than about 3 mol %; less than about 2 mol %; less than about 1 mol %; less than about 0.5 mol %; or less than about 0.05 mol %.

Oxygen may be maintained as the limiting reagent in the third bulk gas mixture 852 introduced to the third vessel 102c, therefore the third intermediate cooled OCM gas 864 will have little, if any, residual oxygen content. In at least some embodiments, a fourth oxidant 870 can be added to the third intermediate cooled OCM gas 864 to provide a fourth bulk gas mixture 872 for introduction to the fourth vessel 102d. In some instances, the fourth oxidant 870 can be added as a cooled, condensed liquid or as a cooled gas to further lower the temperature of the fourth bulk gas mixture 872. In some situations, the composition of the fourth bulk gas mixture 872 can be controlled or otherwise adjusted using one of more analyzers to provide a process signal input indicative of the composition of the fourth bulk gas mixture 872 to one or more flow or composition controllers. The one or more controllers can provide a control signal output to one or more final control elements, for example one or more flow control valves capable of controlling or otherwise adjusting the flow of the fourth oxidant 870. In some situations the temperature of the fourth bulk gas mixture 872 can be controlled or otherwise adjusted using one of more temperature transmitters to provide a process signal input indicative of the temperature of the fourth bulk gas mixture 872 to one or more temperature controllers. The one or more controllers can provide a control signal output to one or more final control elements, for example one or more flow control valves capable of controlling or otherwise adjusting the flow of the boiler feed water 306 to the one or more thermal transfer devices 822c.

The methane concentration within the fourth bulk gas mixture 872 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %. The oxygen concentration within the fourth bulk gas mixture 872 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %.

In one or more embodiments, the oxygen concentration in the fourth bulk gas mixture 872 may also be measured and adjusted to selectively control the OCM reaction within the fourth vessel 102d. For example, the oxygen concentration in the fourth bulk gas mixture 872 may be controlled or otherwise adjusted or provide a targeted thermal profile through at least one of the layers 402 forming catalyst bed 104d or to provide a targeted thermal profile through the entire catalyst bed 104d. In some embodiments, the oxygen concentration within the fourth bulk gas mixture 872 can be measured and adjusted via one or more feedback controllers communicably coupled to a final control element 874 on the fourth oxidant 870. The oxygen concentration within the fourth bulk gas mixture 872 can be less than about 5 mol %; less than about 10 mol %; less than about 15 mol %; less than about 20 mol %; less than about 25 mol %; less than about 30 mol %; less than about 40 mol %; less than about 50 mol %; less than about 60 mol %; less than about 70 mol %.

In addition to the composition, the methane-to-oxygen stoichiometric ratio in the fourth bulk gas mixture 872 may also be measured and adjusted to selectively control the OCM reaction within the fourth vessel 102d. For example, the methane-to-oxygen stoichiometric ratio in the fourth bulk gas mixture 872 may be controlled or otherwise adjusted or provide a targeted thermal profile through at least one of the layers 402 forming catalyst bed 104d or to provide a targeted thermal profile through the entire catalyst bed 104d. Establishing the stoichiometric ratio within the fourth bulk gas mixture 872 such that oxygen is the limiting reagent (i.e., maintaining a stoichiometric ratio of greater than 2:1) may advantageously minimize the likelihood of a detonation or deflagration occurring within the third vessel 102c. One or more analyzers may be used to determine either or both the methane and the oxygen concentration(s) in fourth bulk gas mixture 872 and provide a process signal input indicative of the concentration(s) to one or more flow or composition controllers. In at least some embodiments the one or more controllers can provide a control output signal to one or more final control elements, for example one or more flow control valves used to adjust the flow of the fourth oxidant 870 to the fourth bulk gas mixture 872. In at least some embodiments, the stoichiometric ratio (expressed as methane molar concentration to oxygen molar concentration) in the fourth bulk gas mixture 872 can be greater than about 2:1; greater than about 2.25:1; greater than about 2.5:1; greater than about 2.75:1; greater than about 3:1; greater than about 3.5:1; greater than about 4:1; greater than about 4.5:1; greater than about 5:1; greater than about 7.5:1; or greater than about 10:1.

Within the fourth vessel 102d, the fourth bulk gas mixture 872 is introduced to a single catalyst bed 104d having two layers 402a and 402b. Within the catalyst bed 104c, at least a portion of the methane present in the fourth bulk gas mixture 872 is converted to form a fourth intermediate OCM gas 880 containing one or more $C_{2+}$ hydrocarbons and at least a portion of the oxygen is consumed to form water and carbon dioxide. Where oxygen is maintained as the limiting reagent in the fourth bulk gas mixture 872, the fourth intermediate OCM gas 880 will contain unreacted methane originally added with the methane source 106. The oxygen concentration in the fourth intermediate OCM gas 880 can be less than about 20 mol %; less than about 15 mol %; less than about 10 mol %; less than about 5 mol %; less than about 2 mol %; less than about 1 mol %; less than about 0.5 mol %; or less than about 0.1 mol %. The methane concentration in the fourth intermediate OCM gas 880 can be less than about 50 mol %; less than about 45 mol %; less than about 40 mol %; less than about 35 mol %; less than about 30 mol %; less than about 25 mol %; less than about 20 mol %; less than about 10 mol %; less than about 5 mol %; less than about 2 mol %; or less than about 1 mol %. The temperature of the OCM gas 880 after exiting vessel 102d and prior to passing through the at least one thermal transfer device 112 can be less than about 1100° C.; less than about 1050° C.; less than about 1000° C.; less than about 900° C.; less than about 800° C.; less than about 700° C.; less than about 650° C.

At least a portion of the thermal energy in the fourth intermediate OCM gas 880 is removed using one or more thermal transfer devices 112. As shown in FIG. 8, in at least some instances, boiler feed water 306 may be used to remove at least a portion of the thermal energy present in the fourth intermediate OCM gas 880 to provide heated boiler feed water, saturated steam or superheated steam 310. One or more temperature sensors and transmitters can be used to provide an input signal indicative of the temperature of the OCM gas 110 to at least one temperature controller. The at least one temperature controller can provide a control signal output to at least one final control element, for example a flow control valve, used to control or otherwise adjust the flow of boiler feed water 306 to the one or more thermal transfer devices 112.

Figure 9:
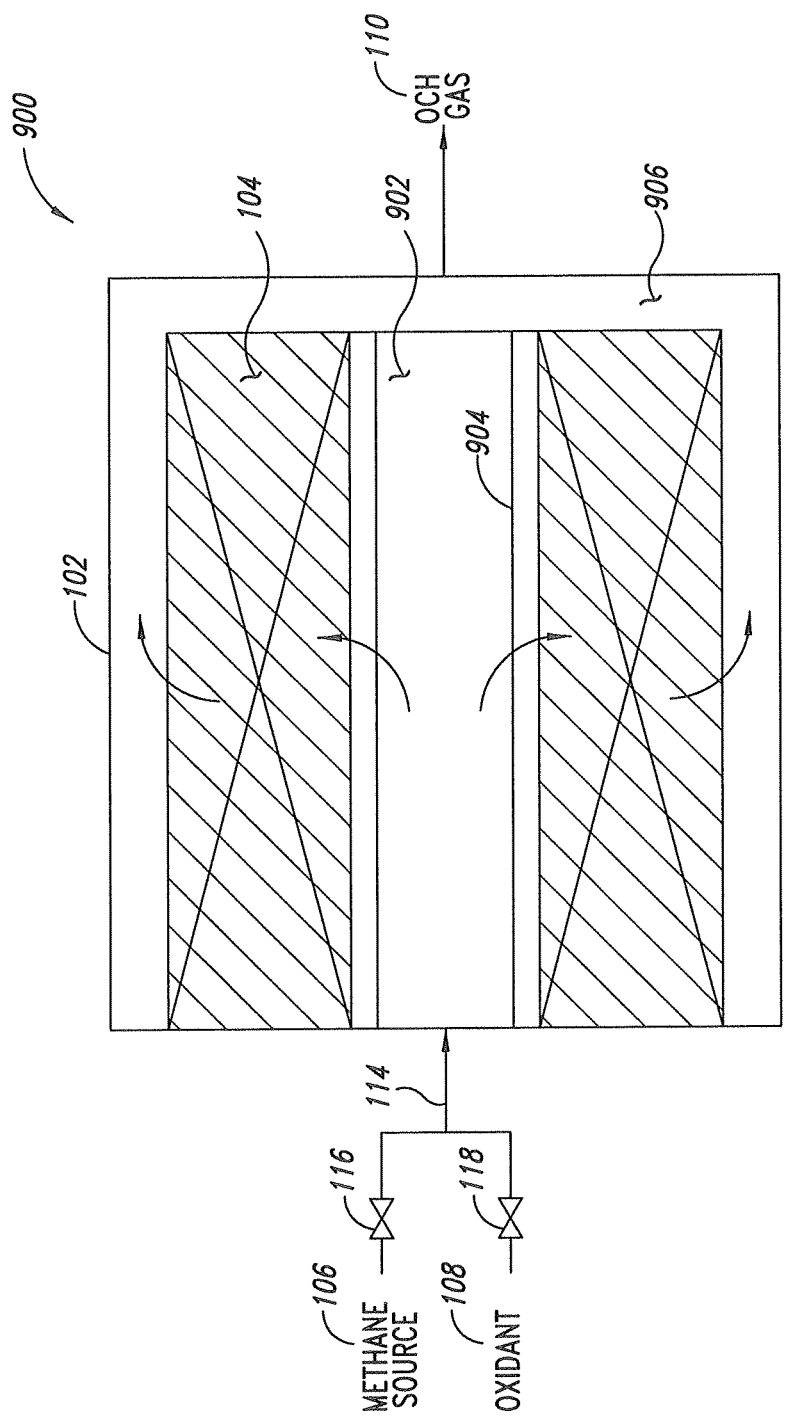
FIG. 9 shows a sectional view of an illustrative vessel for the isothermal, exothermic, reaction of a methane source and an oxidant over at least one catalyst to provide an oxidative coupling of methane ("OCM") gas.

FIG. 9 shows a system 400 for the production of one or more alkene hydrocarbons via oxidative coupling of methane ("OCM") using one or more annular vessels 102 having a single catalyst bed 104 operating under substantially adiabatic conditions. For illustrative purposes and for clarity, brevity, and conciseness, a single vessel 102 having a single catalyst bed 104 will be discussed in detail, however one of ordinary skill in the art will readily appreciate that any number of beds 104 having any number of layers may be similarly disposed in any number of vessels 102.

The methane source 106 and the oxidant 108 are mixed or otherwise combined to provide the bulk gas mixture 114. The bulk gas mixture 114 is introduced to one or more chambers 902 each defined by one or more permeable walls 904. The bulk gas mixture 114 in each of the chambers 902 penetrates through the permeable walls 904 and passes through the catalyst bed 104 arranged annularly about each of the one or more chambers 902.

In some instances, the catalyst bed 104 may contain one or more layers 402. Each layer 402 within the catalyst bed 104 may contain one or more catalysts, one or more inert materials, or combinations thereof. The individual catalysts or inerts selected for inclusion in each layer 402 may be selected for one or more properties or characteristics that include, but are not limited to, catalyst activity, catalyst end product selectivity, catalyst or inert gas phase pressure drop, catalyst or inert effect on thermal profile through the individual layer or through the entire bed, or combinations thereof.

Each of the layers 402 may be homogeneous, containing a catalyst having a single chemical composition, a catalyst having a single physical configuration, an inert having a single chemical composition, or an inert having a single physical configuration. Alternatively, all or a portion of the layers 402 may be heterogeneous, containing two or more catalysts having differing chemical compositions or physical configurations, or containing two or more inert materials having differing chemical compositions or physical configurations.

The catalyst bed 104 can be controlled or operated in a variety of manners. In some instances, a desired temperature increase or linear or non-linear temperature profile across one or more layers 402 within the catalyst bed 104 may be used to establish a target temperature or a target composition for the bulk gas mixture 114. In at least some embodiments, at least one of: the temperature; the pressure; the flow; or the composition of the bulk gas mixture 114 may be adjusted or otherwise controlled to maintain a temperature rise across the catalyst bed 104 of less than about 250° C.; less than about 225° C.; less than about 200° C.; less than about 175° C.; less than about 150° C.; less than about 125° C.; less than about 100° C.; less than about 75° C.; or less than about 50° C.

In at least some embodiments, at least one of: the temperature; the pressure; the flow; or the composition of the bulk gas mixture 114 may be controlled or otherwise adjusted to maintain a maximum temperature rise rate across the catalyst bed 104 of less than about 200° C.; less than about 150° C.; less than about 100° C.; less than about 75° C.; less than about 50° C./cm; less than about 40° C./cm; less than about 30° C./cm; less than about 25° C./cm; less than about 20° C./cm; less than about 15° C./cm; less than about 10° C./cm; less than about 5° C./cm; less than about 1° C./cm; or less than about 0.5° C./cm. In at least some embodiments, at least one of: the temperature; the pressure; the flow; or the composition of the bulk gas mixture 114 may be controlled or otherwise adjusted to maintain a maximum temperature within the catalyst bed 104 of less than about 1100° C.; less than about 1050° C.; less than about 1000° C.; less than about 950° C.; less than about 900° C.; less than about 850° C.; less than about 800° C.; less than about 750° C.; less than about 700° C.; less than about 650° C.; or less than about 600° C.

Operationally, an annular reactor such as that depicted in FIG. 9 may be characterized in some instances based upon the entry surface (i.e., catalyst bed inlet) area formed by the chamber 902 divided by the catalyst bed 104 volume (units of inverse length). In at least some embodiments, the ratio of the inlet area to bed volume can be less than about 1000 $m^{-1}$; less than about 500 $m^{-1}$; less than about 250 $m^{-1}$; less than about 200 $m^{-1}$; less than about 150 $m^{-1}$; less than about 100 $m^{-1}$; less than about 50 $m^{-1}$; less than about 25 $m^{-1}$; less than about 10 $m^{-1}$; less than about 5 $m^{-1}$; less than about 2.5 $m^{-1}$; less than about 1 $m^{-1}$, less than 0.1 $m^{-1}$, less than 0.01 $m^{-1}$, less than 0.001 $m^{-1}$, or even less than 0.0005 $m^{-1}$ The bulk gas mixture 114 is introduced to the catalyst bed 104. Within the catalyst bed 104, at least a portion of the methane present in the bulk gas mixture 114 is converted to form an OCM gas 110 containing one or more hydrocarbons and at least a portion of the oxygen is consumed to form water and carbon dioxide. OCM Gas f110 exits the catalyst bed and is collected in a collection channel disposed about the perimeter of the catalyst bed 104. Where oxygen is maintained as the limiting reagent in the bulk gas mixture 114, the OCM gas 110 removed from the vessel 102 will contain unreacted methane added with the methane source 106.

The foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs) or programmable gate arrays. However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

Various methods and/or algorithms have been described. Some or all of those methods and/or algorithms may omit some of the described acts or steps, include additional acts or steps, combine acts or steps, and/or may perform some acts or steps in a different order than described. Some of the method or algorithms may be implemented in software routines. Some of the software routines may be called from other software routines. Software routines may execute sequentially or concurrently, and may employ a multi-threaded approach.

In addition, those skilled in the art will appreciate that the mechanisms taught herein are capable of being distributed as a program product in a variety of forms, and that an illustrative embodiment applies equally regardless of the particular type of signal bearing media used to actually carry out the distribution. Examples of nontransitory signal bearing media include, but are not limited to, the following: recordable type media such as portable disks and memory, hard disk drives, CD/DVD ROMs, digital tape, computer memory, and other nontransitory computer-readable storage media.

These and other changes can be made to the embodiments in light of the above-detailed description. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to U.S. Provisional Patent Application No. 61/651,485, filed May 24, 2012 and U.S. Provisional Patent Application No. 61/791,312, filed Mar. 15, 2013 are incorporated herein by reference, in their entirety. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for generating hydrocarbons having two or more carbon atoms ($C_{2+}$ hydrocarbons), comprising:
   (a) providing a methane source and an oxidant source;
   (b) directing methane from said methane source and an oxidant from said oxidant source into a reaction unit, wherein said reaction unit comprises a catalyst bed that includes at least one oxidative coupling of methane (OCM) catalyst that facilitates an OCM reaction using said methane and said oxidant, wherein said at least one OCM catalyst is a nanostructured catalyst, and wherein said catalyst bed has an inlet zone that is contacted by a bulk gas mixture formed upon entry of said methane from said methane source and said oxidant from said oxidant source into said reaction unit; and
   (c) in said reaction unit, conducting said OCM reaction using said methane and said oxidant to generate said $C_{2+}$ hydrocarbons under conditions that are selected to:
     a. maintain a thermal profile across said catalyst bed during said OCM reaction, which thermal profile is characterized by (i) a temperature of said inlet zone being less than 550° C., and (ii) a maximum temperature within said catalyst bed being greater than about 800° C.;
     b. maintain a pressure within said reaction unit greater than about 15 pounds per square inch gauge (psig); and
     c. maintain said OCM reaction within said catalyst bed at a methane conversion of at least about 6% and a $C_{2+}$ hydrocarbon selectivity of at least about 40%.

2. The method of claim 1, wherein said conditions are selected to maintain said OCM reaction within said catalyst bed under substantially adiabatic conditions.

3. The method of claim 1, wherein said conditions are selected to maintain said OCM reaction at a $C_{2+}$ hydrocarbon selectivity of at least about 50%.

4. The method of claim 1, further comprising maintaining said methane source at a temperature of at least about 400° C. using at least one heat transfer unit thermally coupled to said methane source.

5. The method of claim 1, further comprising maintaining said oxidant source at a temperature of at least about 400° C. using at least one heat transfer unit thermally coupled to said oxidant source.

6. The method of claim 1, further comprising maintaining said methane source at a temperature of at most about 600° C. using at least one heat transfer unit thermally coupled to said methane source.

7. The method of claim 1, wherein said OCM reaction is maintained at a methane conversion of at least about 10%.

8. The method of claim 1, wherein said reaction unit comprises a plurality of serially coupled vessels, wherein each of said serially coupled vessels includes at least one catalyst bed, and wherein said method further comprises (i) operating said catalyst bed in each of said plurality of serially coupled vessels under substantially adiabatic conditions and (ii) maintaining said OCM reaction at a $C_{2+}$ hydrocarbon selectivity of at least 50% within said catalyst bed in each of said plurality of serially coupled vessels.

9. The method of claim 8, further comprising using a thermal transfer unit located upstream of a given vessel among said plurality of serially coupled vessels to maintain a bulk gas temperature of at most about 700° C. in an inlet zone of said given vessel.

10. The method of claim 8, further comprising, using at least one thermal adjustment unit fluidly coupled between a first vessel and a second vessel of said plurality of serially coupled vessels, said first vessel being upstream of said second vessel, performing at least one of (i) removing a portion of an OCM product stream comprising said $C_{2+}$ hydrocarbons from said first vessel and directing a remainder of said OCM product stream to said second vessel, (ii) directing said methane or said oxidant to said second vessel, and (iii) transferring heat from said OCM product stream to a coolant.

11. The method of claim 1, further comprising conducting said OCM reaction using said methane and said oxidant to generate said $C_{2+}$ hydrocarbons under conditions that are selected to maintain said pressure within said reaction unit greater than about 30 pounds per square inch gauge (psig).

12. The method of claim 1, further comprising conducting said OCM reaction using said methane and said oxidant to generate said $C_{2+}$ hydrocarbons under conditions that are selected to maintain said pressure within said reaction unit greater than about 45 pounds per square inch gauge (psig).

13. The method of claim 1, further comprising adjusting a proportion between a concentration of said methane and a concentration of said oxidant in said inlet zone to provide a ratio between said methane and said oxidant in said inlet zone such that said oxidant acts as a limiting reagent.

14. The method of claim 1, further comprising measuring a temperature of said catalyst bed using a temperature sensor positioned within said catalyst bed.

15. The method of claim 1, wherein said thermal profile across said catalyst bed has a maximum temperature within said catalyst bed of less than about 900° C.

16. The method of claim 2, wherein said thermal profile is further characterized by a temperature increase across said catalyst bed of greater than about 200° C.

17. The method of claim 1, wherein said nanostructured catalyst is selected from the group consisting of a metal oxide, a metal hydroxide, a perovskite, a metal oxyhydroxide, a metal oxycarbonate, a metal carbonate, a metal element from any of Groups 1 through 7, a lanthanide, and an actinide.

18. The method of claim 1, wherein said nanostructured catalyst comprises at least one metal dopant that provides said $C_{2+}$ hydrocarbon selectivity of at least about 40%.

19. The method of claim 1, wherein said methane source has a temperature that is less than about 600° C.

20. The method of claim 1, wherein said temperature of said inlet zone is less than 500° C.

* * * * *